United States Patent
Church et al.

(10) Patent No.: US 12,018,321 B2
(45) Date of Patent: Jun. 25, 2024

(54) RNA-GUIDED SYSTEMS FOR PROBING AND MAPPING OF NUCLEIC ACIDS

(71) Applicant: President and Fellows of Harvard College, Cambridge, MA (US)

(72) Inventors: George M. Church, Brookline, MA (US); Frederic Vigneault, Ashland, MA (US); Kalim U. Mir, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 574 days.

(21) Appl. No.: 17/114,541

(22) Filed: Dec. 8, 2020

(65) Prior Publication Data

US 2021/0102244 A1 Apr. 8, 2021

Related U.S. Application Data

(63) Continuation of application No. 15/504,421, filed as application No. PCT/US2015/045805 on Aug. 19, 2015, now abandoned.

(60) Provisional application No. 62/039,341, filed on Aug. 19, 2014.

(51) Int. Cl.
| | |
|---|---|
| C12Q 1/68 | (2018.01) |
| C12N 9/22 | (2006.01) |
| C12N 15/11 | (2006.01) |
| C12Q 1/6832 | (2018.01) |
| C12Q 1/6874 | (2018.01) |

(52) U.S. Cl.
CPC ............ *C12Q 1/6832* (2013.01); *C12N 9/22* (2013.01); *C12N 15/11* (2013.01); *C12Q 1/6874* (2013.01); *C12N 2310/20* (2017.05); *C12N 2800/80* (2013.01)

(58) Field of Classification Search
CPC ...... C12Q 1/6832; C12Q 1/6874; C12N 9/22; C12N 15/11; C12N 2310/20; C12N 2800/80
See application file for complete search history.

(56) References Cited

U.S. PATENT DOCUMENTS

| | | |
|---|---|---|
| 9,260,752 B1 | 2/2016 | May et al. |
| 2004/0057967 A1 | 3/2004 | Bavari et al. |
| 2009/0093551 A1 | 4/2009 | Bhatia et al. |
| 2009/0099041 A1 | 4/2009 | Church et al. |
| 2009/0105082 A1 | 4/2009 | Chetverin et al. |
| 2011/0045004 A1 | 2/2011 | Radbruch et al. |
| 2014/0068797 A1 | 3/2014 | Doudna et al. |
| 2014/0186958 A1 | 7/2014 | Zhang et al. |
| 2014/0220580 A1 | 8/2014 | Brown et al. |
| 2014/0357523 A1 | 12/2014 | Zeiner et al. |
| 2016/0348169 A1* | 12/2016 | Brown ............... C12Q 1/68 |

FOREIGN PATENT DOCUMENTS

| | | |
|---|---|---|
| JP | 2003-503007 A | 1/2003 |
| JP | 2005-517382 A | 6/2005 |
| WO | 2013176772 A1 | 11/2013 |
| WO | 2013/188522 A2 | 12/2013 |
| WO | 2014/189628 A1 | 11/2014 |
| WO | 2015/048690 A1 | 4/2015 |
| WO | 2015/116686 A1 | 8/2015 |

OTHER PUBLICATIONS

Nallur, G et al. Signal Amplification By Rolling Circle Amplification on DNA Microarrays. Nucleic Acids Res. Dec. 1, 2001, vol. 29, No. 23; E 118; p. 1, second column, second paragraph; p. 6, Figure 5A; DOI: 10.1093/nar/29.23.e118.
Hsu, Pd et al. DNA Targeting Specificity of RNA.Guided CAS9 Nucleases. Nat Biotechnol. Sep. 2013, vol. 31, No. 9; pp. 827-832; p. 827, first column, first paragraph to p. 827, second column, third paragraph; p. 828, first column, first paragraph; p. 833, second column, fourth paragraph; DOI: 10.1038/nbl.2647.
International Search Report issued from corresponding PCT/US2015/045805, dated May 20, 2016.
Chen, Baohui et al., "Dynamic Imaging of Genomic Loci in Living Human Cells by an optimized CRISPR/Cas System". Cell (2013) vol. 155, issue 7, pp. 1479-1491.
Takahashi, Toyozo, "Applied Technologies with DNA Probes", Mar. 2000, CMC Publishing Co., Ltd, pp. 34-42.
Masami Muramatsu et al. Ed., Experimental Medicine, Separate Volume, "New Genetic Engineering Handbook, Revised 3rd Edition", Mar. 1999, Yodosha Co., Ltd, p. 97-96.
Office Action dated Jul. 23, 2019, for Japanese Application No. 2017-510315.
Jinek et al., "A Programmable Dual-RNA-Guided DNA Endonuclease in Adaptive Bacterial Immunity," Science, vol. 337, pp. 816-821 (Aug. 17, 2012).
Fu et al., "Sequencing double-stranded DNA by strand displacement," Nucleic Acids Research, vol. 25, No. 3, pp. 677-679 (1997).

\* cited by examiner

*Primary Examiner* — Catherine S Hibbert
(74) *Attorney, Agent, or Firm* — Banner & Witcoff, Ltd.

(57) ABSTRACT

Methods of detecting, probing, mapping and directed sequencing of target nucleic acids are provided using a guide RNA and a Cas9 protein. Methods for detecting the binding of the guide RNA/Cas9 complex to a target nucleic acid where the guide RNA includes a 3' tail sequence that can hybridize to a probe are provided. Methods for detecting the binding of the guide RNA/Cas9 complex to a target nucleic acid where the complex is physically detected are provided.

19 Claims, 15 Drawing Sheets

Specification includes a Sequence Listing.

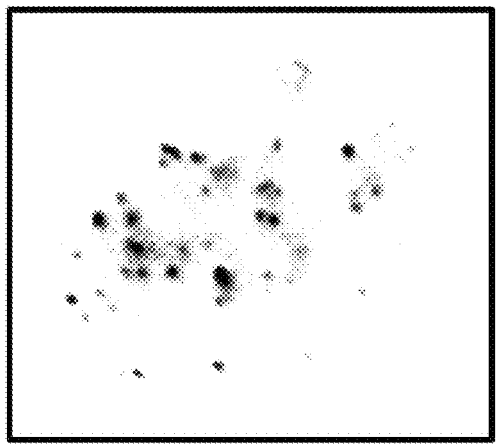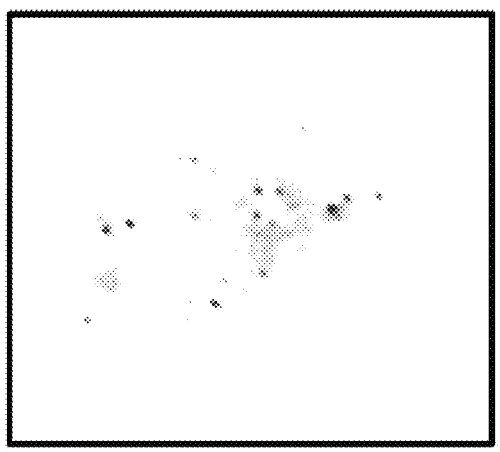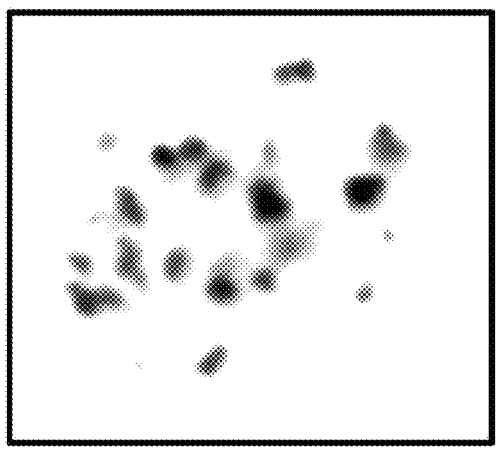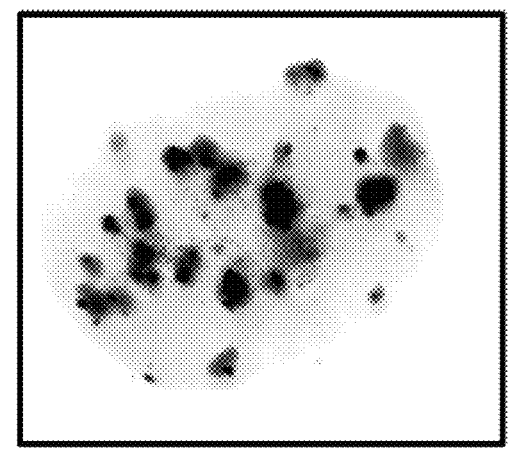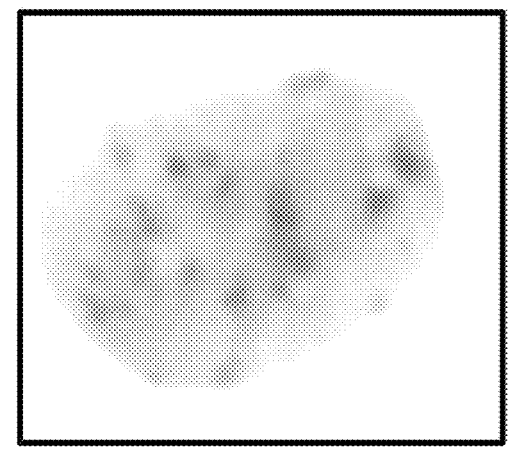

Figure 4E
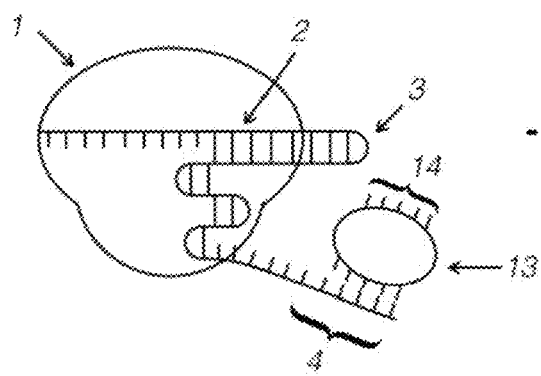
Figure 4F
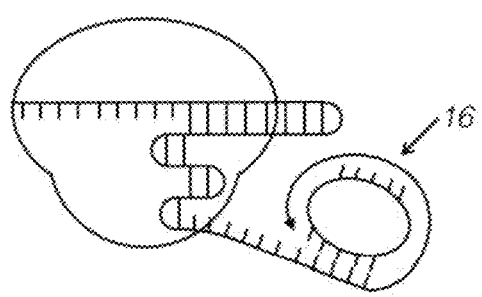
Figure 4H
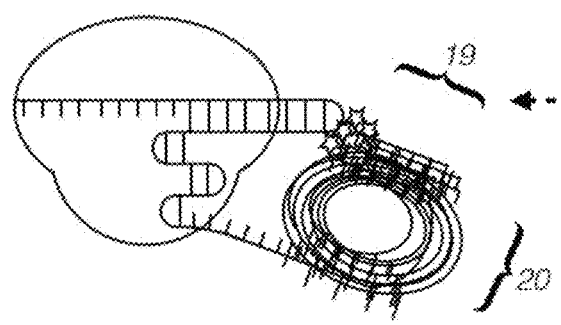
Figure 4G
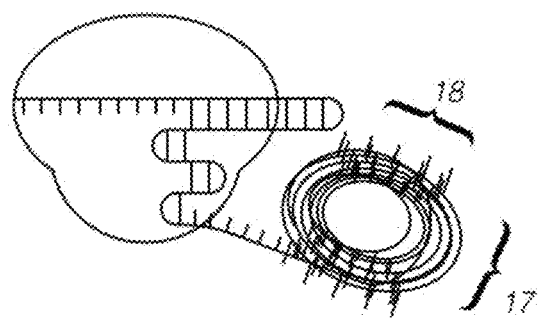

Figure 4I
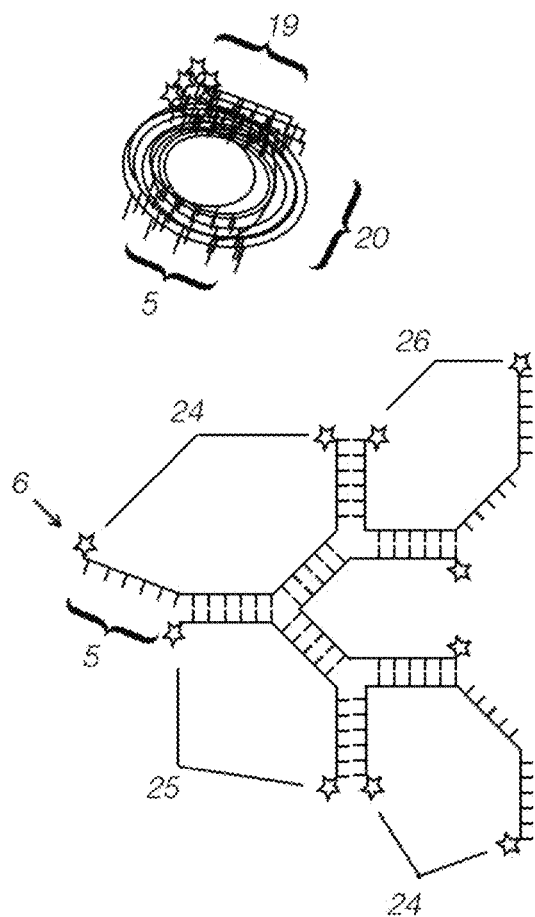
Figure 4J
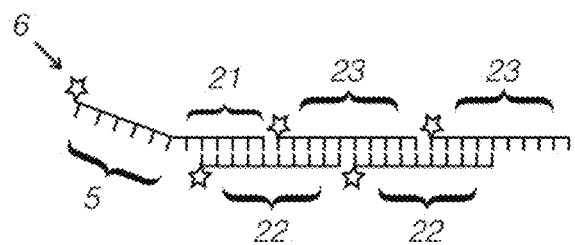
Figure 4K
Figure 4L
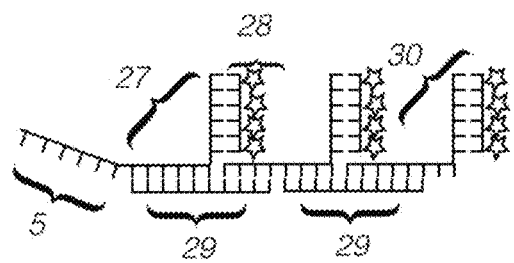

Figure 5A
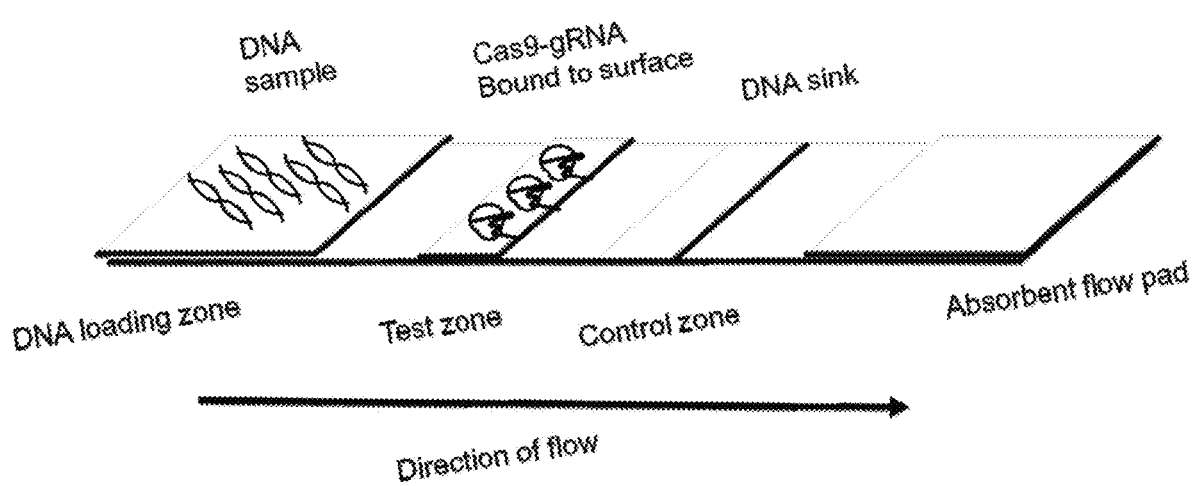
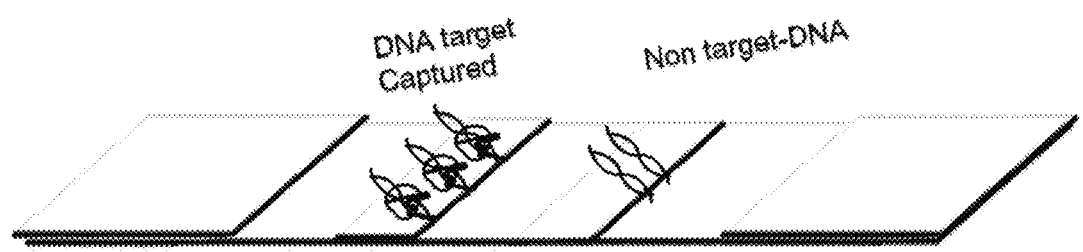

Figure 5C
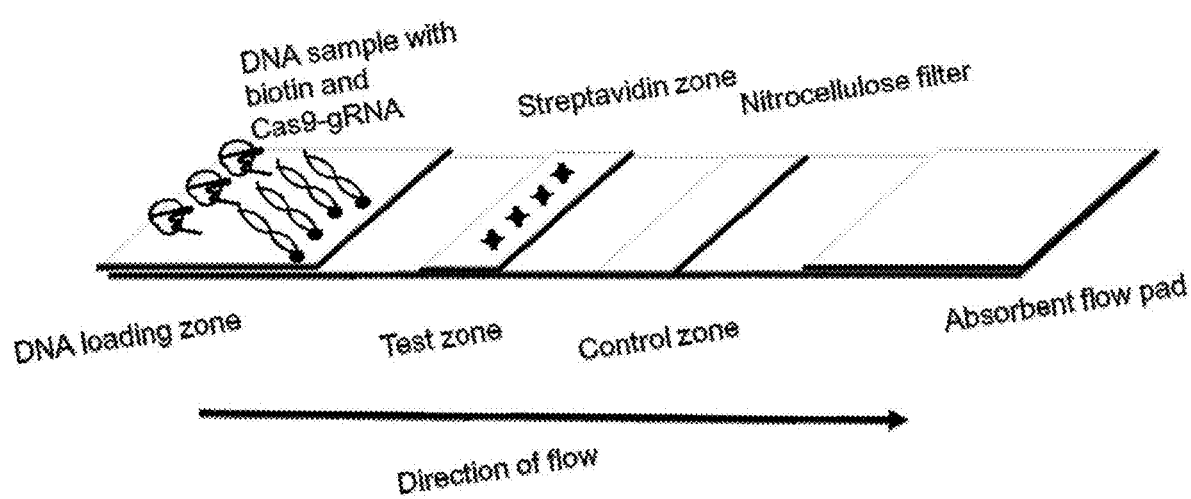
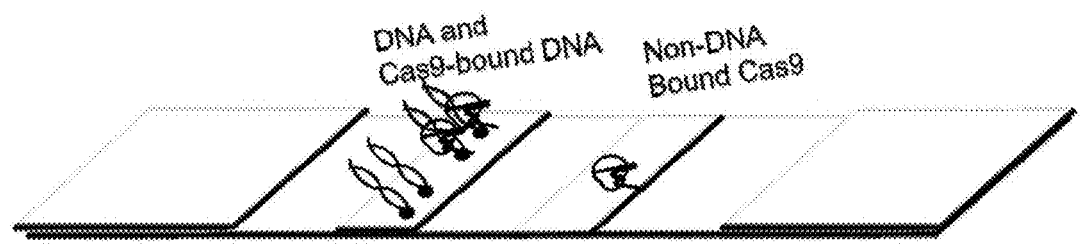

Fwd-t7-gRNA GAAATTAATACGACTCACTATAGG (Tm = 52°C)
Sp.gRNA.split60 TTAATACGACTCACTATAGG................AAGTTTTAGAGCTAGAAATAGCAA (Tm = 55°C)
gRNA.split60 GTTTTAGAGCTAGAAATAGCAAGTTAAAATAAGGCTAGTCCGTTATCAACTTGAAAAAGTGGCACCGAGTCGGTGCTTTT (Tm = 55°C)
Rev=B1-gRNA.18 ACGGACTGGGTGCTTTTTTATACATGTA (Tm = 62°C)

RNA-GUIDED SYSTEMS FOR PROBING AND MAPPING OF NUCLEIC ACIDS

RELATED APPLICATIONS

This application is a continuation application which claims priority to U.S. patent application Ser. No. 15/504,421, filed on Feb. 16, 2017, which application is a National Stage Application under 35 U.S.C. 371 of co-pending PCT application PCT/US15/45805 designating the United States and filed Aug. 19, 2015; which claims the benefit of Provisional application No. 62/039,341 and filed Aug. 19, 2014 each of which are hereby incorporated by reference in their entireties.

BACKGROUND

Bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. *Nature* 471, 602-607 (2011); Gasiunas, G, Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. *Science* 337, 816-821 (2012); Sapranauskas, R. et al. The *Streptococcus thermophilus* CRISPR/Cas system provides immunity in *Escherichia coli*. *Nucleic acids research* 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type II CRISPR system demonstrated that crRNA ("CRISPR RNA") fused to a normally trans-encoded tracrRNA ("transactivating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus thermophilus*. *Journal of Bacteriology* 190, 1390 (February 2008). Various uses of CRISPR/Cas9 systems are known. See WO2014/099744, WO2013176772, U.S. Pat. No. 8,697,359 and Sternberg et al., *Nature*, Vol. 507, pp. 62-67 (2014).

SUMMARY

Aspects of the present disclosure are directed to a method of detecting a target nucleic acid sequence including the steps of contacting the target nucleic acid sequence with a guide RNA sequence having a portion complementary to the target nucleic acid sequence and a Cas9 protein, wherein the guide RNA and the Cas9 protein co-localize to the target nucleic acid sequence to form a complex, and wherein the complex is detected thereby detecting the target nucleic acid sequence. According to one aspect, the method is performed ex vivo, i.e. in vitro, such as within a vessel or on a substrate. According to one aspect, the guide RNA and Cas9 proteins are prepared and isolated to be used as reagents in the in vitro methods of the present disclosure. Aspects of the present methods include the probing, such as analytical probing or preparative probing, detecting, labeling, mapping and sequencing of nucleic acids, such as DNA. For example, the present disclosure is directed to methods of probing DNA, such as at the single molecule level, for the purpose of identifying the presence of the DNA, probing DNA for the purpose of affinity purifying the DNA, mapping the DNA, to mark out specific regions of importance along the DNA, or to create sequencing start sites.

According to methods described herein, a complex is formed including a guide RNA, a DNA binding protein, such as a Cas9 protein, and a double stranded DNA target sequence. According to certain aspects, DNA binding proteins within the scope of the present disclosure include a protein that forms a complex with the guide RNA and with the guide RNA guiding the complex to a double stranded DNA sequence wherein the complex binds to the DNA sequence. This aspect of the present disclosure may be referred to as co-localization of the RNA and DNA binding protein to or with the double stranded DNA. In this manner, a DNA binding protein-guide RNA complex may be used to form a detectable complex at a specific target DNA sequence, thereby detecting the presence of the target DNA sequence. According to certain aspects, the complex may be detected due to the presence of a detectable label. According to certain aspects, the complex may be directly labeled or indirectly labeled. According to certain aspects, the detectable label may be present on the guide RNA, the Cas9 protein or the complex.

According to certain aspects, a colocalization factor for the guide RNA may not be a DNA-binding protein. A reagent may be used to colocalize with the guide RNA at the target nucleic acid sequence. According to certain aspects, the guide RNA need not require the presence of a DNA binding protein to be useful in certain aspects of the present disclosure. The DNA binding protein may be absent. For example, a guide RNA may itself bind to the target nucleic acid sequence and the guide RNA may have a label or other functional moiety attached thereto so as to localize the label or other functional moiety at or near the target nucleic acid sequence.

According to certain aspects, the complex may be detected by detecting the structure of the complex without having a detectable label. The physical structure of the complex is probed as opposed to visualizing a fluorescent or other visually or spectroscopically detectable moiety. According to certain aspects, the complex may be detected by detecting the physic-chemical property of the complex, such as electrostatic charge, without having a detectable label. Such methods include detecting the complex using nanopore detection methods, electron microscopy, optical microscopy, scanning probe microscopy, atomic force microscopy, cantilever detection methods, quartz crystal detection methods, field effect transistor detection methods, all of which are known to those of skill in the art. One of skill will readily envision other methods which are capable of detecting the structure of the complex based on the present disclosure.

According to certain aspects, the term "guide RNA" in the context of a CRISPR Cas9 system is known to those of skill in the art and includes a portion, such as a 20 nucleotide portion, that is complementary to a target nucleic acid. Methods of designing guide RNA are well known to those of skill in the art. Methods described herein include contacting the target nucleic acid sequence with a plurality of guide RNA sequences, each having a portion complementary to the target nucleic acid sequence. Methods described herein include contacting a plurality of target nucleic acid sequences with a plurality of corresponding guide RNA sequences, each having a portion complementary to a corresponding target nucleic acid sequence.

According to certain aspects, guide RNA according to the present disclosure includes a portion complementary to a target nucleic acid and a 3'-tail portion or sequence which is or may be complementary to or otherwise binds to a probe sequence or detectable label. According to one aspect, the 3' tail portion provides a specific functionality. The 3' tail portion may be modular and bear multiple elements, for the same and for multiple functionalities. According to one aspect, the 3' tail portion may be complementary to or otherwise bind (e.g. via an aptamer mechanism) to one or more or multiple probe sequence(s) or detectable label(s). Each probe sequence or detectable label may serve a distinct role (for example the role of one sequence may be to bind to a CY3 labeled oligonucleotide and the role of a second sequence may be to bind to a Cy5 labeled oligonucleotide). For example, the tail sequence can be used to localize a functional protein to a target nucleic acid sequence. For example, the tail sequence can bind the part of the target duplex that is displaced by the guide RNA.

According to one aspect, the probe sequence includes a detectable label, and the probe sequence is bound to the 3' tail sequence. According to one aspect, the probe sequence includes a plurality of detectable labels, and the probe sequence is bound to the 3' tail sequence. According to one aspect, the probe sequence includes a detectable label, and the probe sequence is bound to the 3' tail sequence, and wherein the probe sequence is amplified. According to one aspect, the probe sequence includes is bound to the 3' tail sequence, and wherein the probe sequence is amplified. According to one aspect, the guide RNA includes a 3' tail sequence as a binding pair to a probe or detectable label. According to one aspect, the tail sequence can act as a primer when bound to a template sequence. The tail sequence is then extended to incorporate one or more detectable labels, such as a fluorescent nucleotide, or one or more binding moieties, such as biotin or dig labeled nucleotides to which one or more labels can be bound directly or indirectly. According to one aspect, rolling circle amplification can be used with the tail primer sequence and a rolling circle amplification template to create a rolling circle concatemer product having a plurality of detectable moieties or binding moieties to which detectable moieties can be attached. In this way, rolling circle amplification can be used to amplify signal intensity. Rolling circle amplification methods are known to those of skill in the art and include Drmanac et al., Human genome sequencing using unchained base reads on self-assembling DNA nanoarrays, Science, vol. 327, p. 78-81 (2009).

According to one aspect, the target nucleic acid is a double stranded nucleic acid. According to one aspect, the target nucleic acid is double stranded genomic DNA. According to one aspect, the target nucleic acid is chromosomal DNA.

According to certain aspects, the guide RNA includes a seed region sequence. According to certain aspects, the guide RNA includes degenerate positions or sequences or universal bases at non-seed regions of the guide RNA.

According to one aspect, the target nucleic acid is elongated on a substrate, such as a planar substrate or a pore or a channel, i.e., the target nucleic acid is elongated within a pore or a channel.

According to one aspect, the Cas9 protein is wild type Cas9, a Cas9 nickase or a nuclease null Cas9, as known to those of skill in the art. Methods of isolating wild type Cas9 are known to those of skill in the art. Methods of making a Cas9 nickase are known to those of skill in the art. Methods of making a nuclease null Cas9 are known to those of skill in the art, According to one aspect, the detectable label is directly or indirectly bound to the Cas9 protein. According to one aspect, the detectable label is directly or indirectly bound to the guide RNA. According to one aspect, the detectable label is part of the guide RNA (e.g. where a fluorescently labeled nucleotide is incorporated during the making (e.g. by in vitro transcription) of the guide RNA. According to one aspect, the detectable label is directly or indirectly bound to the complex.

According to one aspect, methods are provided whereby the sequence of the target nucleic acid is determined by sequencing methods. According to one aspect, the Cas9 protein is a Cas9 nickase which nicks a strand of the target nucleic acid and wherein primer extension or chain extension is initiated from the nick, with the complementary strand serving as a template, thereby sequencing the target nucleic acid, such as one of the strands of the target nucleic acid. The advantage over other nicking approaches, such as the use of nicking endonucleases and DNAse 1, is that the location where nicks are created is programmable via the use of the guide RNA and, multiple specific locations can be targeted. One can use computer implemented methods and software to identify the parts of the genome of interest for synthesis, order the DNA templates required to make the gRNA, in vitro transcribe the guide RNA and then implement nicking at the desired locations to carry out targeted sequencing. Methods of sequencing by primer extension along a template are known to those of skill in the art. The use of a nick as a primer is known to those skilled in the art. This feature of the present disclosure can also be used to include a detectable label in an extension product thereby detecting the target nucleic acid, such as instead of or in addition to obtaining sequence information from the target nucleic acid. Accordingly, the Cas9 protein is a Cas9 nickase which nicks a strand of the target nucleic acid and wherein primer extension is initiated from the nick to include a detectable label, with the complementary strand serving as a template, thereby detecting the target nucleic acid. According to this aspect, once the label is incorporated into the extension product, the gRNA/Cas9 complex need not remain with the target DNA, as the label that has been incorporated into the extension product is detected.

According to one aspect, the isolated guide RNA and isolated Cas9 protein are combined under suitable conditions and then contacted with the target nucleic acid in a reaction or complex forming medium in vitro. According to one aspect, the target nucleic acid is within a sample, such as a nucleic acid sample. The nucleic acid sample may include a plurality of nucleic acids and may be referred to as a complex mixture of nucleic acids. According to certain aspects, methods are provided for identifying a target nucleic acid within a complex mixture of nucleic acids with the guide RNA being specific for the target nucleic acid. According to one aspect, methods are provided for identifying one or more or a plurality of target nucleic acids within a complex mixture of nucleic acids with guide RNAs being specific for one or more or a plurality of the target nucleic acids. In this aspect, a multiplex method for detecting a plurality of target nucleic acids is provided. Each of the target nucleic acids in the plurality may be bound by a corresponding guide RNA/Cas 9 protein complex, and thereby being capable of being detected or sequenced as described herein or as known in the art.

According to certain aspects, methods are provided for affinity purifying a target nucleic acid within a complex mixture of nucleic acids with the guide RNA being specific for the target nucleic acid. According to one aspect, methods are provided for affinity purifying one or more or a plurality of target nucleic acids within a complex mixture of nucleic acids with guide RNAs being specific for one or more or a plurality of the target nucleic acids. In this aspect, a multiplex method for affinity purifying a plurality of target nucleic acids is provided. Each of the target nucleic acids in the plurality may be bound by a corresponding guide RNA/Cas 9 protein complex. According to these aspects, an affinity system using binding pairs known to those of skill in the art can be used. A target nucleic acid is purified by depleting other nucleic acids in the complex mixture. A target nucleic acid is purified by depleting it from the complex mixture. The depletion may occur by affinity capture of the target to be depleted. Alternatively, the depletion can occur by cleavage of the target to be depleted. In some cases, nucleic acids with high abundance within the complex mixture may need to be depleted from the mixture in order to analyze targets at lower abundance. For example, it may be desirable to deplete repetitive DNA or other high concentration nucleic acids from a sample.

According to certain aspects, methods are provided for depleting a target nucleic acid within a complex mixture of nucleic acids with the guide RNA being specific for the nucleic acid targeted for depletion. According to one aspect, methods are provided for one or more or a plurality of target nucleic acids within a complex mixture of nucleic acids with guide RNAs being specific for one or more or a plurality of the target nucleic acids. In this aspect, a multiplex method for depleting a plurality of target nucleic acids is provided. Each of the nucleic acids targeted for depletion in the plurality may be bound by a corresponding guide RNA/Cas 9 protein complex.

According to certain aspects, the target nucleic acid is within a solution sample. According to certain aspects, the target nucleic acid is present on a substrate. According to certain aspects, the target nucleic acid is bound to a substrate. According to certain aspects, the target nucleic acid is within a cell. According to one aspect, the cell is a eukaryotic cell. According to one aspect, the cell is a yeast cell, a plant cell or an animal cell. According to one aspect, the cell is a mammalian cell. In certain embodiments, the mammalian cell is a live cell and a guide RNA or a DNA binding protein, such as a Cas9 or other DNA binding protein are delivered by electroporation, carrier-mediated delivery (e.g. lipofectin), microinjection and other methods known to those of skill in the art. In certain embodiments the mammalian cell is a fixed cell which is bathed in a solution containing a guide RNA and a DNA binding protein, such as a Cas9 or other DNA binding protein that is to be delivered. In a similar manner, methods described herein using a gRNA and DNA binding protein to colocalize at a target nucleic acid sequence can be conducted on a metaphase chromosome spread.

According to one aspect, the guide RNA is between about 10 to about 500 nucleotides. According to one aspect, the guide RNA is between about 20 to about 100 nucleotides. According to one aspect, the guide RNA is a tracrRNA-crRNA fusion. According to one aspect, the tracrRNA and crRNA are separate species and are fused.

According to one aspect, the DNA is genomic DNA, mitochondrial DNA, viral DNA, or exogenous DNA.

According to one aspect, a method is provided for probing a sample including a mixture of two or more different polynucleotide species or cells, such as are characterized by their DNA content, by selecting one or more sequences complementary to one or more polynucleotide species in the sample, producing one or more gRNAs including the complementary sequence, combining the one or more gRNAs with Cas9, exposing the sample to the gRNA and Cas9, detecting gRNA/Cas9 binding to one or more polynucleotide species in the sample; determining the identity of the cell or the polynucleotide constituents of the sample based on the detection. According to one aspect, the gRNA and Cas9 are produced in vitro or are present in vitro. According to one aspect, the gRNA and Cas9 are combined in vitro. According to one aspect the gRNA is produced or is present in vitro whereas the Cas 9 protein is produced in vivo. According to an additional aspect, the sample includes a plurality of different polynucleotide species, such as may be present in a complex mixture of 10s or 100s or 1000s or 10,000s of different polynucleotide species.

Other applications include a method for assessing the identity of a target organism comprising using guide RNAs and a Cas9; a method for assessing the state of a target organism comprising using guide RNAs and a Cas9; a method for mapping DNA molecules comprising resolving a plurality of Cas9 and guide RNA complexes bound on a DNA molecule; or a method for resolving allelic variants in a DNA molecule comprising using a plurality of Cas9 and guide RNA complexes and a plurality of probes. Each of these specific applications is based on the method of probing DNA using a gRNA/Cas9 system described herein to form a complex at a target DNA site and detecting the gRNA/Cas9 complex.

The DNA molecule can be chromosomal or extra-chromosomal. The Cas9 endonuclease can be active, or be inactive or be partially-inactive. The Cas9 can be in fusion with a fluorescent protein (such as GFP, Luciferase and the like) and/or one or multiple affinity tag. The affinity tag can be recognized by one or multiple fluorescent probes. The affinity tag can be recognized by one or multiple tags, adding a measurable attribute to Cas9 (e.g. charge or shape). The Cas9 can contain one or multiple orthogonal amino acids. Orthogonal amino acids can provide affinity to other molecules, such as a probe, a tag, a linker.

The guide RNA can be probed directly using one or multiple fluorescent probes. The guide RNA can be probed directly by one or multiple tags adding a measurable attribute to Cas9 (e.g. charge or shape). The guide RNA can contain one or multiple modified bases. Modified bases can provide affinity to other molecules, such as a probe, a tag, a linker.

The organism may be a prokaryote or an eukaryote, unicellular or multicellular. The DNA is extracted from the organism. The DNA can be in its native form, or the DNA can be stretched on a surface or in a device. The DNA can translocate through a channel or a nanopore. The organism is fixed and made permeable to an in vitro synthesized Cas9 and guide RNA complex.

In certain embodiments, the Cas9 and guide RNA are complexed before being used to target the DNA. The guide RNA is complementary to the target DNA. The complex bound to DNA is detected by measuring fluorescent signal (s). The complex bound to DNA is detected by measuring the current signal while translocating through a nanopore sensor or in proximity to a nanopore or nanogap sensor.

One or multiple complexes on a DNA can be detected at once. The resolution between any two complexes on a DNA can be as low as 1 nanometer or 5 nanometers or 10 nanometers and as high as 1000 millimeters (and any number in between). The detection of specific complexes indicates the presence of specific alleles. A pattern of the complexes bound to DNA can be created and used to provide a map of the DNA molecule. A pattern of the complexes bound to DNA can be created and used to provide the identity and/or the state of the organism. According to one aspect, the guide RNA or Cas9 or guideRNA/Cas9 complex can be provided to either live or nonviable (i.e., dead) cells.

A method for using the Cas9 and guide RNA complex to create sequence specific start sites on a DNA molecule is provided. Single molecule sequencing can be performed using a polymerase or a ligase. The start site could be proximal to a genomic variant, a repeat sequence, a highly variable region.

A method for using the Cas9 and guide RNA complex to pulldown DNA molecules, i.e affinity purification, is provided. An affinity tag allowing for pulldown is bound to the Cas9 and guide RNA complex. The affinity tag is bound to the complex before or after the complex bind to the DNA. A specific or multiple specific target DNA molecule(s) bound to one or multiple Cas9 and guide RNA complex can be extracted from a pool. The extracted target DNA molecules can be submitted to sequencing, such as deep sequencing.

In certain embodiments, the guide RNA is used without Cas9 (or other DNA binding protein), under certain conditions and when targeted against certain types of sequences, the guide RNA is sufficient to form a stable or a transient attachment to the DNA target.

In certain embodiments, the gRNA/Cas9 colocalization complex provides double stranded cleavage, but the gRNA/Cas9 colocalization complex remains bound to the target nucleic acid. Such a gRNA/Cas9 colocalization may be removed from the target nucleic acid using conditions such as addition of 7 M Urea to begin to break up the complex (see Sternberg et al Nature 507:62 (2014) hereby incorporated by reference in its entirety.)

In some embodiments, a complex of gRNA and Cas9 is formed before binding to a target nucleic acid sequence, such as DNA. In some embodiments, the complex is formed after Cas9 interacts with the target nucleic acid first, i.e. Cas9 interacts with the target nucleic acid and then a colocalization complex is formed with the guide RNA.

Further features and advantages of certain embodiments of the present invention will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which:

FIG. 1A-1E present images of a fixed mouse cell probed by labeled gRNA/Cas9.

FIG. 4A-4L present various schematics for probing the gRNA tail.

FIG. 5A-5C present diagrams of lateral flow assays.

DETAILED DESCRIPTION

Figure 2C:
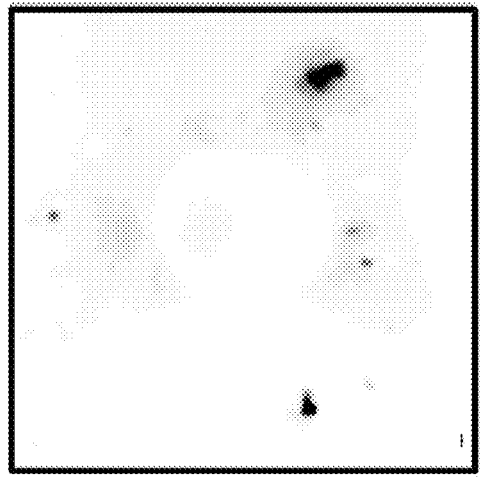
FIG. 2A-2E present images of a fixed mouse cell probed by labeled oligonucleotides following the Cas9 probing protocol as in FIG. 1A-1E.
Figure 2B:
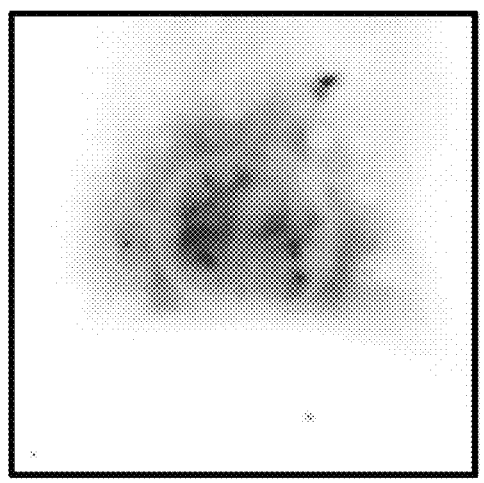
Figure 2A:
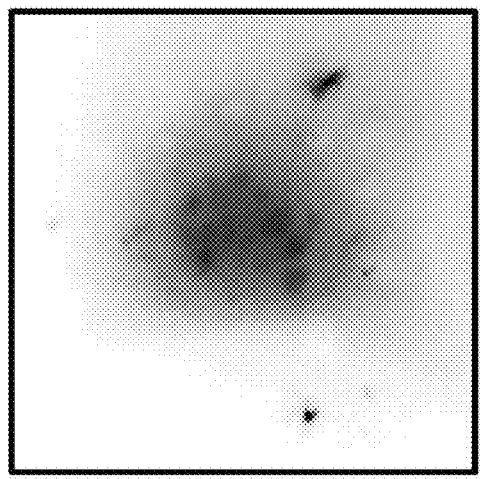
Figure 2E:
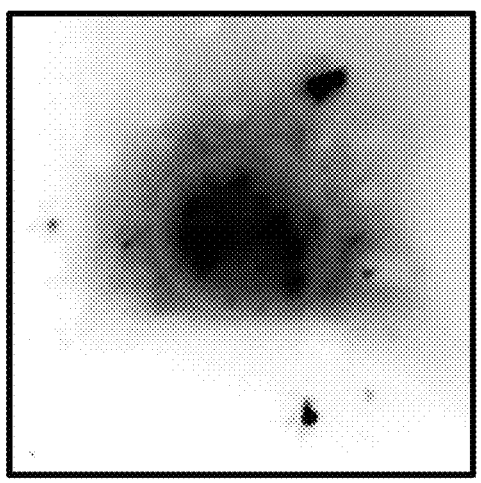
Figure 2D:
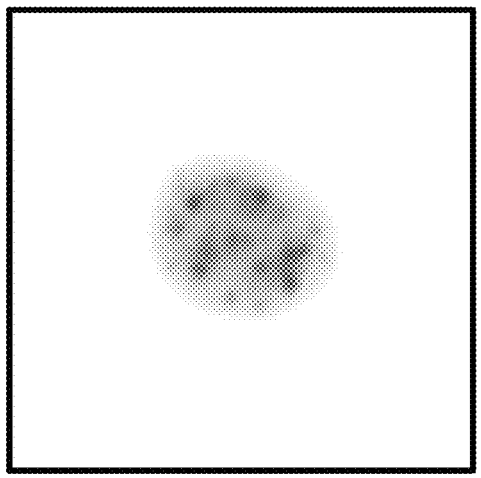

Embodiments of the present disclosure are based on the use of DNA binding proteins and guide RNA to co-localize at or complex at a target nucleic acid and then detect the target nucleic acid, by detection of a detectable moiety associated with or attached to the complex or by physically probing the complex itself. Such DNA binding proteins include RNA-guided DNA binding proteins readily known to those of skill in the art to bind to DNA for various purposes. Such DNA binding proteins may be naturally occurring. DNA binding proteins included within the scope of the present disclosure include those which may be guided by RNA, referred to herein as guide RNA. According to this aspect, the guide RNA and the RNA guided DNA binding protein form a co-localization complex at the DNA. According to certain aspects, the DNA binding protein may be a nuclease-null DNA binding protein. According to this aspect, the nuclease-null DNA binding protein may result from the alteration or modification of a DNA binding protein having nuclease activity. Such DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al., *Nature Reviews, Microbiology*, Vol. 9, June 2011, pp. 467-477 including all supplementary information hereby incorporated by reference in its entirety.

Exemplary DNA binding proteins having nuclease activity function to nick or cut double stranded DNA. Such nuclease activity may result from the DNA binding protein having one or more polypeptide sequences exhibiting nuclease activity. Such exemplary DNA binding proteins may have two separate nuclease domains with each domain responsible for cutting or nicking a particular strand of the double stranded DNA. Exemplary polypeptide sequences having nuclease activity known to those of skill in the art include the McrA-HNH nuclease related domain and the RuvC-like nuclease domain. Accordingly, exemplary DNA binding proteins are those that in nature contain one or more of the McrA-HNH nuclease related domain and the RuvC-like nuclease domain. According to certain aspects, the DNA binding protein is altered or otherwise modified to inactivate the nuclease activity. Such alteration or modification includes altering one or more amino acids to inactivate the nuclease activity or the nuclease domain. Such modification includes removing the polypeptide sequence or polypeptide sequences exhibiting nuclease activity, i.e. the nuclease domain, such that the polypeptide sequence or polypeptide sequences exhibiting nuclease activity, i.e. nuclease domain, are absent from the DNA binding protein. Other modifications to inactivate nuclease activity will be readily apparent to one of skill in the art based on the present disclosure. Accordingly, a nuclease-null DNA binding protein includes polypeptide sequences modified to inactivate nuclease activity or removal of a polypeptide sequence or sequences to inactivate nuclease activity. The nuclease-null DNA binding protein retains the ability to bind to DNA even though the nuclease activity has been inactivated. Accordingly, the DNA binding protein includes the polypeptide sequence or sequences required for DNA binding but may lack the one or more or all of the nuclease sequences exhibiting nuclease activity. Accordingly, the DNA binding protein includes the polypeptide sequence or sequences required for DNA binding but may have one or more or all of the nuclease sequences exhibiting nuclease activity inactivated.

According to one aspect, a DNA binding protein having two or more nuclease domains may be modified or altered to inactivate all but one of the nuclease domains. Such a modified or altered DNA binding protein is referred to as a DNA binding protein nickase, to the extent that the DNA binding protein cuts or nicks only one strand of double stranded DNA. When guided by RNA to DNA, the DNA binding protein nickase is referred to as an RNA guided DNA binding protein nickase. Accordingly, useful Cas9 proteins may be a wild type Cas9, a Cas9 nickase or a nuclease null Cas9 and homologs and orthologs thereof. See Jinek et al., Science 337, 816-821 (2012) hereby incorporated by reference in its entirety.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinek et al., Science 337, 816-821 (2012) hereby incorporated by reference in its entirety. Cas9 proteins are known to exist in many Type II CRISPR systems including the following as identified in the supplementary information to Makarova et al., Nature Reviews, Microbiology, Vol. 9, June 2011, pp. 467-477: *Methanococcus maripaludis* C7; *Corynebacterium diphtheriae*; *Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua*; *Lactobacillus casei*; *Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans*; *Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus thermophiles* CNRZ1066; *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum*; *Mycoplasma mobile* 163K; *Mycoplasma penetrans*; *Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni doylei* 269 97; *Campylobacter jejuni* 81116; *Campylobacter jejuni*; *Campylobacter lari* RM2100; *Helicobacter hepaticus*; *Wolinella succinogenes*; *Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida*; *Francisella tularensis novicida* U112; *Francisella tularensis holarctica*; *Francisella tularensis* FSC 198; *Francisella tularensis tularensis*; *Francisella tularensis* WY96-3418; and *Treponema denticola* ATCC 35405. Accordingly, aspects of the present disclosure are directed to a Cas9 protein present in a Type II CRISPR system, which has been rendered nuclease null or which has been rendered a nickase as described herein.

The Cas9 protein may be referred by one of skill in the art in the literature as Csn1. The *S. pyogenes* Cas9 protein sequence is shown below. See Deltcheva et al., Nature 471, 602-607 (2011) hereby incorporated by reference in its entirety.

```
                                              (SEQ ID NO: 7)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ
```

-continued

```
LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRK

MIAKSEQEIGKATAKYFFYSNIMNFFKTEITLANGEIRKRPLIETNGETG

EIVWDKGRDFATVRKVLSMPQVNIVKKTEVQTGGFSKESILPKRNSDKLI

ARKKDWDPKKYGGFDSPTVAYSVLVVAKVEKGKSKKLKSVKELLGITIME

RSSFEKNPIDFLEAKGYKEVKKDLIIKLPKYSLFELENGRKRMLASAGEL

QKGNELALPSKYVNFLYLASHYEKLKGSPEDNEQKQLFVEQHKHYLDEII

EQISEFSKRVILADANLDKVLSAYNKHRDKPIREQAENIIHLFTLTNLGA

PAAFKYFDTTIDRKRYTSTKEVLDATLIHQSITGLYETRIDLSQLGGD-
```

Target nucleic acids include any nucleic acid sequence to which a co-localization complex as described herein can be useful to detect. Target nucleic acids include genes. The target nucleic acid may be within DNA extracted from a single cell. The target nucleic acid may be DNA extracted from a single chromosome. For purposes of the present disclosure, DNA, such as double stranded DNA, can include the target nucleic acid and a co-localization complex can bind to or otherwise co-localize with the DNA at or adjacent or near the target nucleic acid and in a manner to detect the target nucleic acid. Such target nucleic acids can include endogenous (or naturally occurring) nucleic acids and exogenous (or foreign) nucleic acids. Such target nucleic acids may be in a mixture of nucleic acids. Such target nucleic acids may be bound to a substrate. Such target nucleic acids may be elongated or stretched using methods known to those of skill in the art. Methods of stretching DNA are described in K H Rasmussen, R Marie, J M Lange, W E Svendsen, A Kristensen, and K U Mir, Lab Chip, 2011, 11:1431-44 and A device for extraction, manipulation and stretching of DNA from single human chromosomes; D L V Bauer, R Marie, K H Rasmussen, A Kristensen, K U Mir, 2012 Nucl Acids Res, 2012, 1-7, DNA catenation maintains structure of human metaphase chromosomes.

Detectable labels or moieties are known to those of skill in the art. As used herein, the term "detectable label" refers to a label that can be used to identify a target nucleic acid. A detectable label is attached to the gRNA or the Cas9 protein using methods known to those of skill in the art. Alternatively, the gRNA or the Cas9 protein may include one half of a binding pair with the other half of the corresponding binding pair being bound to a detectable label. In this manner, the label may be indirectly bound to the gRNA or Cas9 protein due to the binding of the binding pairs. Suitable binding pairs or binding forces are known to those of skill in the art and include complementary nucleic acid sequences, biotin-avidin, biotin-streptavidin, NHS-ester and the like, a thioether linkage, static charge interactions, van der Waals forces and the like (See, e.g., Holtke et al., U.S. Pat. Nos. 5,344,757; 5,702,888; and 5,354,657; Huber et al., U.S. Pat. No. 5,198,537; Miyoshi, U.S. Pat. No. 4,849,336; Misiura and Gait, PCT publication WO 91/17160). Biotin, or a derivative thereof, may be used as an oligonucleotide label (e.g., as a targeting moiety, retrievable moiety and/or a detectable label), and subsequently bound by a avidin/streptavidin derivative (e.g., detectably labelled, e.g., phycoerythrin-conjugated streptavidin), or an anti-biotin antibody (e.g., a detectably labelled antibody). Digoxigenin may be incorporated as a label and subsequently bound by a detectably labelled anti-digoxigenin antibody (e.g., a detectably labelled antibody, e.g., fluoresceinated anti-digoxigenin). An aminoallyl-dUTP residue may be incorporated into an oligonucleotide and subsequently coupled to an N-hydroxy succinimide (NHS) derivatized fluorescent dye. In general, any member of a conjugate pair may be incorporated into a retrievable moiety and/or a detectable label provided that a detectably labelled conjugate partner can be bound to permit detection. As used herein, the term antibody refers to an antibody molecule of any class, or any sub-fragment thereof, such as an Fab.

Detectable labels may vary widely in size and compositions; the following references provide guidance for selecting oligonucleotide tags appropriate for particular embodiments: Brenner, U.S. Pat. No. 5,635,400; Brenner et al., Proc. Natl. Acad. Sci., 97: 1665; Shoemaker et al. (1996) Nature Genetics, 14:450; Morris et al., EP Patent Pub. 0799897A1; Wallace, U.S. Pat. No. 5,981,179; and the like.

Methods for incorporating detectable labels into nucleic acid probes are well known. Typically, detectable labels (e.g., as hapten- or fluorochrome-conjugated deoxyribonucleotides) are incorporated into a nucleic acid, such as a nucleic acid probe during a polymerization or amplification step, e.g., by PCR, nick translation, random primer labeling, terminal transferase tailing (e.g., one or more labels can be added after cleavage of the primer sequence), and others (see Ausubel et al., 1997, Current Protocols In Molecular Biology, Greene Publishing and Wiley-Interscience, New York).

A detectable moiety, label or reporter can be used to detect a target nucleic acid as described herein. Guide RNA or Cas9 proteins can be labeled in a variety of ways, including the direct or indirect attachment of a detectable moiety such as a fluorescent moiety, hapten, colorimetric moiety and the like. A location where a label may be attached is referred to herein as a label addition site or detectable moiety addition site and may include a nucleotide to which the label is capable of being attached. One of skill in the art can consult references directed to labeling of nucleic acids or proteins. Examples of detectable moieties include various radioactive moieties, enzymes, prosthetic groups, fluorescent markers, luminescent markers, bioluminescent markers, metal particles, protein-protein binding pairs, protein-antibody binding pairs and the like. Examples of fluorescent moieties include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, cyanines, dansyl chloride, phycocyanin, phycoerythrin and the like. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorinidases, phosphatases, peroxidases, cholinesterases and the like. Identifiable markers also include radioactive compounds such as 125I, 35S, 14C, or 3H. Identifiable markers are commercially available from a variety of sources.

Fluorescent labels and their attachment to nucleotides and/or oligonucleotides are described in many reviews, including Haugland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991). Particular methodologies applicable to the invention are disclosed in the following sample of references: U.S. Pat. Nos. 4,757,141, 5,151,507 and 5,091,519. In one aspect, one or more fluorescent dyes are used as labels for labeled target sequences, e.g., as disclosed by U.S. Pat. No. 5,188,934 (4,7-dichlorofluorescein dyes); U.S. Pat. No. 5,366,860 (spectrally resolvable rhodamine dyes); U.S. Pat. No. 5,847, 162 (4,7-dichlororhodamine dyes); U.S. Pat. No. 4,318,846 (ether-substituted fluorescein dyes); U.S. Pat. No. 5,800,996 (energy transfer dyes); Lee et al.; U.S. Pat. No. 5,066,580 (xanthine dyes); U.S. Pat. No. 5,688,648 (energy transfer dyes); and the like. Labeling can also be carried out with quantum dots, as disclosed in the following patents and patent publications: U.S. Pat. Nos. 6,322,901, 6,576,291, 6,423,551, 6,251,303, 6,319,426, 6,426,513, 6,444,143, 5,990,479, 6,207,392, 2002/0045045 and 2003/0017264. As used herein, the term "fluorescent label" includes a signaling moiety that conveys information through the fluorescent absorption and/or emission properties of one or more molecules. Such fluorescent properties include fluorescence intensity, fluorescence lifetime, emission spectrum characteristics, energy transfer, and the like.

Commercially available fluorescent nucleotide analogues readily incorporated into nucleotide and/or oligonucleotide sequences include, but are not limited to, Cy3-dCTP, Cy3-dUTP, Cy5-dCTP, Cy5-dUTP (Amersham Biosciences, Piscataway, NJ), fluorescein-12-dUTP, tetramethylrhodamine-6-dUTP, TEXAS RED™-5-dUTP, CASCADE BLUE™-7-dUTP, BODIPY™ FL-14-dUTP, BODIPY™ R-14-dUTP, BODIPY™ TR-14-dUTP, RHODAMINE GREEN™-5-dUTP, OREGON GREEN® 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY™ R-14-UTP, BODIPY™ TR-14-UTP, RHODAMINE GREEN™-5-UTP, ALEXA FLUOR™ 488-5-UTP, LEXA FLUOR™ 546-14-UTP (Molecular Probes, Inc. Eugene, OR) and the like. Alternatively, the above fluorophores and those mentioned herein may be added during oligonucleotide synthesis using for example phosphoroamidite or NHS chemistry. Protocols are known in the art for custom synthesis of nucleotides having other fluorophores (See, Henegariu et al. (2000) Nature Biotechnol. 18:345). 2-Aminopurine is a fluorescent base that can be incorporated directly in the oligonucleotide sequence during its synthesis. Nucleic acid could also be stained, a priori, with an intercalating dye such as DAPI, YOYO-1, ethidium bromide, cyanine dyes (e.g. SYBR Green) and the like.

Other fluorophores available for post-synthetic attachment include, but are not limited to, ALEXA FLUOR™ 350, ALEXA FLUOR™ 405, ALEXA FLUOR™ 430, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY™ R, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, Pacific Orange, rhodamine 6G, rhodamine green, rhodamine red, tetramethyl rhodamine, Texas Red (available from Molecular Probes, Inc., Eugene, OR), Cy2, Cy3, Cy3.5, Cy5, Cy5.5, Cy7 (Amersham Biosciences, Piscataway, NJ) and the like. FRET tandem fluorophores may also be used, including, but not limited to, PerCP-Cy5.5, PE-Cy5, PE-Cy5.5, PE-Cy7, PE-Texas Red, APC-Cy7, PE-Alexa dyes (610, 647, 680), APC-Alexa dyes and the like.

FRET tandem fluorophores may also be used, such as PerCP-Cy5.5, PE-Cy5, PE-Cy5.5, PE-Cy7, PE-Texas Red, and APC-Cy7; also, PE-Alexa dyes (610, 647, 680) and APC-Alexa dyes.

Metallic silver or gold particles may be used to enhance signal from fluorescently labeled nucleotide and/or oligonucleotide sequences (Lakowicz et al. (2003) BioTechniques 34:62).

Biotin, or a derivative thereof, may also be used as a label on a nucleotide and/or an oligonucleotide sequence, and subsequently bound by a detectably labeled avidin/streptavidin derivative (e.g. phycoerythrin-conjugated streptavidin), or a detectably labeled anti-biotin antibody. Biotin/avidin is an example of a ligand-ligand binding pair. An antibody/antigen binding pair may also be used with methods described herein. Other ligand-ligand binding pairs or conjugate binding pairs are well known to those of skill in the art. Digoxigenin may be incorporated as a label and subsequently bound by a detectably labeled anti-digoxigenin antibody (e.g. fluoresceinated anti-digoxigenin). An aminoallyl-dUTP or aminohexylacrylamide-dCTP residue may be incorporated into an oligonucleotide sequence and subsequently coupled to an N-hydroxy succinimide (NHS) derivatized fluorescent dye. In general, any member of a conjugate pair may be incorporated into a detection oligonucleotide provided that a detectably labeled conjugate partner can be bound to permit detection. As used herein, the term antibody refers to an antibody molecule of any class, or any sub-fragment thereof, such as an Fab.

Other suitable labels may include fluorescein (FAM, FITC), digoxigenin, dinitrophenol (DNP), dansyl, biotin, bromodeoxyuridine (BrdU), hexahistidine (6×His), phosphor-amino acids (e.g. P-tyr, P-ser, P-thr) and the like. In one embodiment the following hapten/antibody pairs are used for detection, in which each of the antibodies is derivatized with a detectable label: biotin/α-biotin, digoxigenin/α-digoxigenin, dinitrophenol (DNP)/α-DNP, 5-Carboxyfluorescein (FAM)/α-FAM.

In certain exemplary embodiments, a nucleotide and/or an oligonucleotide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, PCT publication WO 91/17160 and the like. Many different hapten-capture agent pairs are available for use. Exemplary haptens include, but are not limited to, biotin, des-biotin and other derivatives, dinitrophenol, dansyl, fluorescein, CY5, digoxigenin and the like. For biotin, a capture agent may be avidin, streptavidin, or antibodies. Antibodies may be used as capture agents for the other haptens (many dye-antibody pairs being commercially available, e.g., Molecular Probes, Eugene, OR).

According to certain aspects, detectable moieties described herein are spectrally resolvable. "Spectrally resolvable" in reference to a plurality of fluorescent labels means that the fluorescent emission bands of the labels are sufficiently distinct, i.e., sufficiently non-overlapping, that molecular tags to which the respective labels are attached can be distinguished on the basis of the fluorescent signal generated by the respective labels by standard photodetection systems, e.g., employing a system of band pass filters and photomultiplier tubes, or the like, as exemplified by the systems described in U.S. Pat. Nos. 4,230,558; 4,811,218, or the like, or in Wheeless et al., pgs. 21-76, in Flow Cytometry: Instrumentation and Data Analysis (Academic Press, New York, 1985). In one aspect, spectrally resolvable organic dyes, such as fluorescein, rhodamine, and the like, means that wavelength emission maxima are spaced at least 20 nm apart, and in another aspect, at least 40 nm apart. In another aspect, chelated lanthanide compounds, quantum dots, and the like, spectrally resolvable means that wavelength emission maxima are spaced at least 10 nm apart, and in a further aspect, at least 15 nm apart.

In certain embodiments, the detectable moieties can provide higher detectability when used with an electron microscope, compared with common nucleic acids. Moieties with higher detectability are often in the group of metals and organometals, such as mercuric acetate, platinum dimethylsulfoxide, several metal-bipyridyl complexes (e.g. osmium-bipy, ruthenium-bipy, platinum-bipy). While some of these moieties can readily stain nucleic acids specifically, linkers can also be used to attach these moieties to a nucleic acid. Such linkers added to nucleotides during synthesis are acrydite- and a thiol-modified entities, amine reactive groups, and azide and alkyne groups for performing click chemistry. Some nucleic acid analogs are also more detectable such as gamma-adenosine-thiotriphosphate, iodode-oxycytidine-triphosphate, and metallonucleosides in general (see Dale et al., Proc. Nat. Acad. Sci. USA, Vol. 70, No. 8, pp. 2238-2242 (1973)). The modified nucleotides are added during synthesis. Synthesis may refer by example to solid support synthesis of oligonucleotides. In this case, modified nucleic acids, which can be a nucleic acid analog, or a nucleic acid modified with a detectable moiety, or with an attachment chemistry linker, are added one after each other to the nucleic acid fragments being formed on the solid support, with synthesis by phosphoramidite being the most popular method. Synthesis may also refer to the process performed by a polymerase while it synthesizes the complementary strands of a nucleic acid template. Certain DNA polymerases are capable of using and incorporating nucleic acids analogs, or modified nucleic acids, either modified with a detectable moiety or an attachment chemistry linker to the complementary nucleic acid template.

Detection method(s) used will depend on the particular detectable labels used in the reactive labels, retrievable labels and/or detectable labels. In certain exemplary embodiments, target nucleic acids such as chromosomes and sub-chromosomal regions of chromosomes during various phases of the cell cycle including, but not limited to, interphase, preprophase, prophase, prometaphase, metaphase, anaphase, telophase and cytokinesis, having one or more reactive labels, retrievable labels, or detectable labels bound thereto by way of the probes described herein may be selected for and/or screened for using a microscope, a spectrophotometer, a tube luminometer or plate luminometer, x-ray film, a scintillator, a fluorescence activated cell sorting (FACS) apparatus, a microfluidics apparatus or the like.

As used herein, the term "chromosome" refers to the support for the genes carrying heredity in a living cell, including DNA, protein, RNA and other associated factors. The conventional international system for identifying and numbering the chromosomes of the human genome is used herein. The size of an individual chromosome may vary within a multi-chromosomal genome and from one genome to another. A chromosome can be obtained from any species. A chromosome can be obtained from an adult subject, a juvenile subject, an infant subject, from an unborn subject (e.g., from a fetus, e.g., via prenatal test such as amniocentesis, chorionic villus sampling, and the like or directly from the fetus, e.g., during a fetal surgery) from a biological sample (e.g., a biological tissue, fluid or cells (e.g., sputum, blood, blood cells, tissue or fine needle biopsy samples, urine, cerebrospinal fluid, peritoneal fluid, and pleural fluid, or cells therefrom) or from a cell culture sample (e.g., primary cells, immortalized cells, partially immortalized cells or the like). In certain exemplary embodiments, one or more chromosomes can be obtained from one or more genera including, but not limited to, *Homo, Drosophila, Caenorhabiditis, Danio, Cyprinus, Equus, Canis, Ovis, Ocorynchus, Salmo, Bos, Sus, Gallus, Solanum, Triticum, Oryza, Zea, Hordeum, Musa, Avena, Populus, Brassica, Saccharum* and the like.

When fluorescently labeled targeting moieties or detectable labels are used, fluorescence photomicroscopy can be used to detect and record the results of in situ hybridization using routine methods known in the art. Alternatively, digital (computer implemented) fluorescence microscopy with image-processing capability may be used. Two well-known systems for imaging FISH of chromosomes having multiple colored labels bound thereto include multiplex-FISH (M-FISH) and spectral karyotyping (SKY). See Schrock et al. (1996) Science 273:494; Roberts et al. (1999) Genes Chrom. Cancer 25:241; Fransz et al. (2002) Proc. Natl. Acad. Sci. USA 99:14584; Bayani et al. (2004) Curr. Protocol. Cell Biol. 22.5.1-22.5.25; Danilova et al. (2008) Chromosoma 117:345; U.S. Pat. No. 6,066,459; and FISH TAG™ DNA Multicolor Kit instructions (Molecular probes) for a review of methods for painting chromosomes and detecting painted chromosomes.

In certain exemplary embodiments, images of fluorescently labeled chromosomes are detected and recorded using a computerized imaging system such as the Applied Imaging Corporation CytoVision System (Applied Imaging Corporation, Santa Clara, CA) with modifications (e.g., software, Chroma 84000 filter set, and an enhanced filter wheel). Other suitable systems include a computerized imaging system using a cooled CCD camera (Photometrics, NU200 series equipped with Kodak KAF 1400 CCD) coupled to a Zeiss Axiophot microscope, with images processed as described by Ried et al. (1992) Proc. Natl. Acad. Sci. USA 89:1388). Other suitable imaging and analysis systems are described by Schrock et al., supra; and Speicher et al., supra.

In situ hybridization methods using probes generated by the methods described herein can be performed on a variety of biological or clinical samples, in cells that are in any (or all) stage(s) of the cell cycle (e.g., mitosis, meiosis, interphase, G0, G1, S and/or G2). Examples include all types of cell culture, animal or plant tissue, peripheral blood lymphocytes, buccal smears, touch preparations prepared from uncultured primary tumors, cancer cells, bone marrow, cells obtained from biopsy or cells in bodily fluids (e.g., blood, urine, sputum and the like), cells from amniotic fluid, cells from maternal blood (e.g., fetal cells), cells from testis and ovary, and the like. Samples are prepared for assays of the invention using conventional techniques, which typically depend on the source from which a sample or specimen is taken. These examples are not to be construed as limiting the sample types applicable to the methods and/or compositions described herein.

In certain exemplary embodiments, probes include multiple gRNA/Cas9 complexes which are differentially labeled (i.e., at least two of the gRNA/Cas9 complexes are differently labeled). Various approaches to multi-color chromosome painting have been described in the art and can be adapted to the present invention following the guidance provided herein. Examples of such differential labeling ("multicolor FISH") include those described by Schrock et al. (1996) Science 273:494, and Speicher et al. (1996) Nature Genet. 12:368). Schrock et al. describes a spectral imaging method, in which epifluorescence filter sets and computer software is used to detect and discriminate between multiple differently labeled DNA probes hybridized simultaneously to a target chromosome set. Speicher et al. describes using different combinations of 5 fluorochromes to label each of the human chromosomes (or chromosome arms) in a 27-color FISH termed "combinatorial multifluor FISH"). Other suitable methods may also be used (see, e.g., Ried et al., 1992, Proc. Natl. Acad. Sci. USA 89:1388-92).

According to certain aspects, a Cas9-gRNA complex is used to probe and access regions of interest on native double stranded DNA without the need to make the target DNA single stranded. A guide RNA specific to the target double stranded nucleic acid sequence of interest is designed using methods known to those of skill in the art, preincubated with Cas9 and then added to a sample containing the target DNA. The guide RNA and Cas9 will then co-localize to and form a complex with the target DNA.

One of skill based on the present disclosure will readily be able to identify or design guide RNAs and Cas9 proteins which co-localize to a DNA including a target nucleic acid. One of skill will further be able to identify detectable moieties for binding to the guide RNA or the Cas9 protein, whether directly or indirectly. DNA includes genomic DNA, mitochondrial DNA, viral DNA or exogenous DNA.

According to one aspect, a guide RNA specific to the sequence of interest is designed. The gRNA is pre-incubated with the Cas9 and then the combination is added to the sample containing the target DNA or otherwise contacted to the target DNA. The gRNA or the Cas9 may include a detectable label or the detectable label may be added after complex formation. The mixture of components may all be provided in solution or the target nucleic acid may be immobilized on a surface or present within in a cell or tissue.

According to aspects of the present disclosure, the CRISPR Cas9 system described herein has the advantage of being sequence specific (with appropriate design) and the target sequences are "programmed" via the 17-25 nucleotides spacer sequence on the gRNA.

The Cas9 system shows highly efficient binding when certain sequences are used in the "seed" region of the gRNA; this can be used as a genome mapping tool based on the frequent occurrence in the genome of these short sequences.

The Cas9 system also may be engineered to become a mapping tool, by using degenerate positions (and/or universal bases) at non-seed regions of the gRNA.

To increase the specificity of the labeling, a cluster of guides can be bound around the locus of interest.

The guide RNAs can be made by direct solid-phase synthesis of RNA (available from vendors such as IDT) or by in vitro transcription of solid-phased synthesized DNA oligos.

The gRNA can be easily synthesized from array-synthesized oligos (which are available in lengths greater than the ~100-200 nt needed), and amplified rendering the cost of each guide very low, and making generation of a large number of gRNA easily scalable. For example Custom Array Inc. can provide 90,000 array synthesized oligos suitable for gRNA generation, in one run of their instrument.

The reaction kinetic is isothermal (37 degrees, possibly room temperature), rapid, under 1 minute, and the resulting complex is very stable and is readily probe-able.

Target DNA may be bulk DNA in solution or immobilised on a surface, DNA in situ in cells, DNA on chromosomes spread on a surface, and to single DNA molecules stretched on a surface or in nanochannels.

Other engineered nucleases, such as Homing endonucleases (HE), Meganuclease, Transcription activator-like effector nuclease (TALEN), Zinc finger nuclease (ZFN), prokaryotic Argonaute (pAgo), or BurrH-based nuclease (BuDN), could be used instead of, or in parallel with Cas9. By example TtAGO has a high affinity to RNA and low affinity for dsDNA.

According to certain aspects, DNA-bound Cas9-sgRNA can be detected by labeling the Cas9 protein directly (e.g. via an affinity tag bound to a quantum dot or an organic dye). Commercially available Cas9 proteins already contain affinity tags (Cas9 from PNABio Inc. includes a Human influenza hemagglutinin (HA); Cas9 available from New England Biolabs includes a Histidine (His) tag. DNA-bound Cas9-sgRNA can be detected by labeling the gRNA, such as at a tail portion at the 3' end of the gRNA and wherein the tail portion may be probed. For example, a fluorescent moiety can be bound to the tail, probes of different color can be bound to create a coding scheme, probes can be exchanged to increase the repertoire of codes. In combination with DNA-PAINT, super-resolution imaging can be achieved. In combination with a fluidic device, EXCHANGE-PAINT can be performed, which enables multiplexing at super-resolution. In this scheme, a limited number of codes can be used for super resolution imaging of a large number of loci by performing cycles of reagent exchange in which at each cycle the same colors are used but are linked to different DNA PAINT imager sequence. For example, just two labels comprising, Cy3B, Atto 655 used 5× times, each time coupled with a different imager sequence, has the capacity to code for ten gRNA. At each cycle a sub-set of the gRNA become labeled. After the cycles have been completed, the identity of the gRNA's is decoded by determining color, and cycle number at which a particular gRNA lights up.

In order to increase signal intensity, oligos labeled with multiple fluorophores can be bound to the tail portion of the gRNA. Alternatively, rolling circle amplification primed by the 3' end of the tail by using an oligo that binds the tail and circularizes as a padlock probe, can be performed. Hybridization chain reaction or other signal amplification methods known to those of skill in the art can also be used.

Detection methods include fluorescence detection methods, electroluminescence detection methods, chemiluminescence detection methods, bioluminescence detection methods and colorimetric detection methods.

Detection methods other than those involving detection of a fluorescent, electroluminescent, chemiluminescent, bioluminescent or colorimetric moiety or complex can be used such as passing Cas9-sgRNA bound DNA strand through nanopores or nanogaps or nanochannels to determine the location of binding of the Cas9-sgRNA, using electron microscopies or scanning probe microscopies for detecting the location of binding of Cas9-sgRNA to DNA elongated/stretched on a surface, detecting the binding of Cas9-sgRNA to target DNA using Cantilevers, Quartz crystal microbalance, field-effect transistors and the like.

According to certain aspects, the presence of a complex of gRNA and Cas9 at a target nucleic acid is determined using nanopore or nanogap detection technology or nanopore or nanogap sequencing technology known to those of skill in the art. Briefly, the target nucleic acid having the gRNA and Cas9 bound thereto in an electrically conductive medium is passed through a nanopore under the influence of a voltage differential. Interface dependent changes in ionic current are used to differentiate between individual nucleotides and the gRNA/Cas9 complex bound to the nucleic acid. In this matter, the presence of the gRNA/Cas9 complex may be detected. According to one aspect, interface dependent changes in ionic current determine entry of the target nucleic acid into the nanopore or nanogap and whether the gRNA/Cas9 complex is bound to the target nucleic acid and the location or locations of binding. When the nucleic acid, as a linear polymer, enters the nanopore, there is a drop in ionic current because the physical presence of the polymer in the pore perturbs the flow of ions through the pore. If a gRNA/Cas9 complex is bound to a particular location on the DNA, then when that location enters the pore, the flow of ions is further decreased, reducing the ionic current. This reduction in current indicates that the gRNA/Cas9 complex is bound to the target nucleic acid. Depending on its size and physico-chemical properties, each type of structure or complex bound to the target nucleic acid (i.e. DNA polymer) will produce a characteristic change in ionic current. gRNA-Cas9 complexes targeting different locations or alleles can be labeled differently so that they can be distinguished by nanopore readout.

"Nanopore" means a hole or passage having a nanometer scale width, such as a hole or passage through a planar surface or membrane. The nanopore may be formed by a multimeric protein ring, such as in a lipid bilayer. The nanopores may be a physical hole in a solid-state planar surface of silicon nitride, graphene or such non-biological material. Typically, the passage is 0.2-25 nm wide. Nanopores, as used herein, may include transmembrane structures that may permit the passage of molecules through a membrane. Examples of nanopores include α-hemolysin (*Staphylococcus aureus*) and MspA (*Mycobacterium smegmatis*). Other examples of nanopores may be found in the art describing nanopore sequencing or described in the art as pore-forming toxins, such as the β-PFTs Panton-Valentine leukocidin S, aerolysin, and Clostridial Epsilon-toxin, the α-PFTs cytolysin A, the binary PFT anthrax toxin, or others such as pneumolysin or gramicidin. Nanopores are becoming technologically and economically significant with the advent of nanopore sequencing technology. Methods for nanopore sequencing are known in the art, for example, as described in U.S. Pat. No. 5,795,782, which is incorporated by reference. Briefly, nanopore detection involves a nanopore-perforated membrane immersed in a voltage-conducting fluid, such as an ionic solution including, for example, KCl, NaCl, NiCl, LiCl or other ion forming inorganic compounds known to those of skill in the art. A voltage is applied across the membrane, and an electric current results from the conduction of ions through the nanopore. When the nanopore interacts with polymers, such as DNA, flow through the nanopore is modulated according to the characteristic of the polymer sub-fragment translocating through the pore at any given time, such as in a monomer-specific manner, resulting in a change in the current that permits identification of the monomer(s) or subfragments. Nanopores within the scope of the present disclosure include solid state nonprotein nanopores known to those of skill in the art and DNA origami nanopores known to those of skill in the art. Such nanopores provide a nanopore width larger than known protein nanopores which allow the passage of larger molecules for detection, such as a Cas9/gRNA complex with a double stranded target nucleic acid, while still being sensitive enough to detect a change in ionic current when the complex passes through the nanopore.

"Nanopore analysis" means a method of determining the components of a polymer, such as a polynucleotide including a gRNA/Cas9 complex, based upon interaction of the polymer with the nanopore. Nanopore analysis may be achieved by measuring a change in the conductance of ions through a nanopore that occurs when the size of the opening is altered by interaction with the polymer.

In addition to a nanopore, the present disclosure envisions the use of a nanogap which is known in the art as being a gap between two electrodes where the gap is about a few nanometers in width such as between about 0.2 nm to about 25 nm or between about 2 and about 5 nm. The gap mimics the opening in a nanopore and allows DNA to pass through or over the gap and between the electrodes. Aspects of the present disclosure also envision use of a nanochannel. Electrodes are placed adjacent to a nanochannel through which the DNA passes. In addition or as an alternative, when the complex is optically labeled, the location of complex binding along a DNA polymer stretched in a nanochannel, can be determined. It is to be understood that one of skill will readily envision different embodiments of molecule or moiety identification and sequencing based on movement of a molecule or moiety through an electric field and creating a distortion of the electric field representative of the structure passing through the electric field.

According to an additional aspect, a Cas9 nickase can be used to nick a target double stranded nucleic acid and the nick used as a sequence-defined priming site for polymerase- or ligase based sequencing, thereby revealing the sequence information surrounding the Cas9-sgRNA target site. A library of guides can be designed which enable the sequencing of many selected parts of the genome, e.g. the exome, regions identified by GWAS signals, specific genes associated with heart disease, cancer etc. Primer extension can also be used to label the site of nicking, such as by incorporation fluorescent nucleotides, by ligation or by incorporation of fluorescent nucleotides followed by ligation. If the primer extension displaces an existing strand, the displaced flap can be labeled by hybridization of an oligo to it, for example. If there are multiple nicking sites, such as when part of the guide contains degenerate sequences, then the multiple sites of labeling can be used as a mapping tool. Primer extension methods are known to those of skill in the art.

Figure 6A:
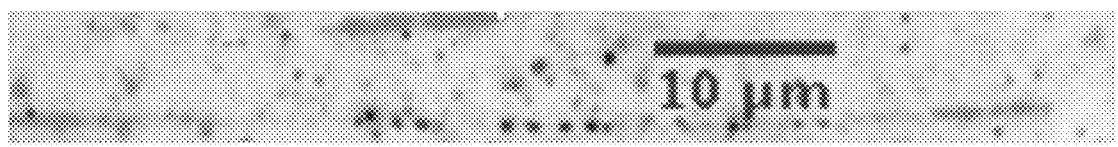
FIG. 6A-6C present images of stretched DNA probed by labeled gRNA/Cas9.

Particular applications of the methods described herein include identification or diagnostic or mapping methods. Access to the "dark matter" of the human genome, such as centromeric repeats as shown in FIG. 6A. Centromere DNA sequences are mostly absent from the current reference genome, due to their highly repetitive nature. Methods of single molecule mapping or sequencing described herein using CRISPR/Cas9 allow the more complete assembly of reference genomes by mapping repetitive sites at a super-resolution in a targeted manner, and also allowing sequencing from those sites. Such methods can be used with personal genomes.

Methods according to the present disclosure include, performing FISH on chromosome spreads at higher efficiency and resolution than currently done using labeled clones. The labeled gRNA/Cas9 complex is an effective FISH probe in the exemplary methods described herein as it allows cleaner signals to be obtained. The methods allow for faster and better identification of chromosomal breakpoints, complex translocations or rearrangements, which is related to many cancer and infertility problems.

Methods according to the present disclosure allow for in vitro diagnostics.

Methods according to the present disclosure allow for probing of genes coding for multi-drug resistance in bacteria, or virus, in the context of a rapid diagnostic platform; in this context Cas9-sgRNA can be used to directly and stably target dsDNA.

The following exemplary methods are also envisioned by the present disclosure.

Wild Type Cas9 Including the Presence of Mg

In some embodiments the invention comprises a method for detecting, labelling, pulling-down or targeting a site in a nucleic acid, comprising: (a) contacting the nucleic acid with a complex comprising a Cas9 protein that has or retains nuclease activity and a guide RNA under conditions in which the complex binds to the nucleic acid, cleaves the nucleic acid, but does not easily dissociate from the nucleic acid (i.e., remains attached to the nucleic acid, holding both cleaved strands together, and (b) analyzing the product of step (a). In some embodiments, such conditions comprise the presence of a divalent cation such as Mg2+. In some embodiments there is at least one wash step between step (a) and step (b). In some embodiments, at least one component of the resulting complex is labelled or tagged. In some embodiments, the guide RNA binds a sequence adjacent to a native PAM site. In some embodiments, the guide RNA binds a sequence adjacent to an artificial PAM site. In some embodiments, the Cas9 is an altered version of Cas9. In some embodiments, the guide RNA is a truncated guide RNA. In some embodiments the truncated guide comprises just the seed region of the guide RNA, i.e. 4-7 nucleotides adjacent to the PAM site.

Wild Type Cas9 in the Absence of Mg

In some embodiments the invention comprises a method for detecting, labelling, pulling-down or targeting a site in a nucleic acid, comprising: (a) contacting the nucleic acid with a complex comprising a Cas9 protein that has or retains nuclease activity and a guide RNA under conditions in which the complex binds to the nucleic acid, does not cleave the nucleic acid and does not easily dissociate from the nucleic acid, and (b) analyzing the product of step (a). In some embodiments, such conditions comprise the absence of a divalent cation such as Mg2+. In some embodiments, there is at least one wash step between step (a) and step (b). In some embodiments, at least one component of the resulting complex is labelled or tagged. In some embodiments, the guide RNA binds a sequence adjacent to a native PAM site. In some embodiments, the guide RNA binds a sequence adjacent to an artificial PAM site. In some embodiments, the Cas9 is an altered version of Cas9. In some embodiments, the guide RNA is a truncated guide RNA. In some embodiments the truncated guide comprises just the seed region of the guide RNA, i.e. 4-7 nucleotides adjacent to the PAM site.

Null/Dead Cas9

In some embodiments, the invention comprises a method for detecting, labelling, pulling-down or targeting a site in a nucleic acid, comprising: (a) contacting the nucleic acid with a complex comprising an enzymatically inactive or nuclease null Cas9 protein such as (e.g D10A/H840A dCas9) and a guide RNA under conditions in which the complex does not cleave the nucleic acid and does not easily dissociate from the nucleic acid, and (b) analyzing the product of step (a). In some embodiments there is at least one wash step between step (a) and step (b). In some embodiments, at least one component of the resulting complex is labelled or tagged. In some embodiments, the guide RNA binds a sequence adjacent to a native PAM site. In some embodiments, the guide RNA binds a sequence adjacent to an artificial PAM site. In some embodiments, the Cas9 is an altered version of Cas9. In some embodiments, the guide RNA is a truncated guide RNA. In some embodiments the truncated guide comprises just the seed region of the guide RNA, i.e. 4-7 nucleotides adjacent to the PAM site.

Nickase Cas9

In some embodiments the invention comprises a method for detecting, labelling, pulling-down or targeting a site in a nucleic acid, comprising: (a) contacting the nucleic acid with a complex comprising a Cas9 nickase (i.e., a nicking mutant of Cas9 protein such as Cas9 D10A or H840A mutants) and a guide RNA under conditions by which the complex does not easily dissociate from the nucleic acid, and (b) analyzing the product of step (a). In some embodiments, there is at least one wash step between step (a) and step (b). In some embodiments, at least one component of the resulting complex is labelled or tagged. In some embodiments, the guide RNA binds a sequence adjacent to a native PAM site. In some embodiments, the guide RNA binds a sequence adjacent to an artificial PAM site. In some embodiments, the Cas9 is an altered version of Cas9. In some embodiments, the guide RNA is a truncated guide RNA. In some embodiments the truncated guide comprises just the seed region of the guide RNA, i.e. 4-7 nucleotides adjacent to the PAM site.

Methods Using a Guide RNA without a DNA Binding Protein

In some embodiments the invention comprises a method for detecting, labelling, pulling-down or targeting a site in a nucleic acid, comprising: (a) contacting the nucleic acid with a guide RNA under conditions by which it does not easily dissociate from the nucleic acid, and (b) analyzing the product of step (a). In some embodiments, there is at least one wash step between step (a) and step (b). In some embodiments, the resulting guide RNA-DNA complex is labelled or tagged. In some embodiments, the label or tag is on a tail. In some embodiments, the guide RNA binds a sequence adjacent to a native PAM site. In some embodiments, the guide RNA binds a sequence adjacent to an artificial PAM site. In some embodiments, the guide RNA does not require binding to a sequence adjacent to a PAM site. In some embodiments, the guide RNA is a truncated guide RNA. In some embodiments, the truncated guide RNA comprises just the seed region of the guide RNA, i.e. 4-7 nucleotides adjacent to the PAM site. In some embodiments, the target locus is a region of repetitive DNA and the signal is amplified. In some embodiments, the target nucleic acid is denatured before addition of guide RNA.

Methods Using an RNA

In some embodiments the invention comprises a method for detecting, labelling, pulling-down or targeting a site in a nucleic acid, comprising: (a) contacting the nucleic acid with an RNA under conditions by which it binds to the nucleic acid, and (b) analyzing the product of step (a). In some embodiments, there is at least one wash step between step (a) and step (b). In some embodiments, the resulting RNA-DNA complex is labelled or tagged. In some embodiments, the label or tag is on a tail. In some embodiments, the target locus is a region of repetitive DNA and the signal is amplified.

Duplex Destabilizing/Opening Reagent and RNA

In some embodiments the invention comprises a method for detecting, labelling, pulling-down or targeting a site in a nucleic acid, comprising: (a) contacting the nucleic acid with a duplex destabilizing/opening reagent and a guide RNA or RNA under conditions in which a complex is formed and binds to the nucleic acid and the complex does not easily dissociate from the nucleic acid, and (b) analyzing the product of step (a). In some embodiments, there is at least one wash step between step (a) and step (b). In some embodiments, at least one component of the resulting complex is labelled or tagged. In some embodiments, the label or tag is on a tail. In some embodiments, the Cas9 is an altered version of Cas9. In some embodiments, the guide RNA is a truncated guide RNA. In some embodiments, the truncated guide comprises just the seed region of the guide RNA, i.e. 4-7 nucleotides adjacent to the PAM site. In some embodiments, the target locus is a region of repetitive DNA and the signal is amplified. A destabilizing reagent (which includes a single strand DNA stabilizing agent) includes a helicase, replication protein A (RPA), E. coli single stranded binding protein (SSB), Betaine, Betaine/Glycine, formamide, urea, DMSO etc. A duplex opening reagent comprises primosome protein PriA, triplex-forming bis-PNA, gamma PNA etc.

RNA Synthesis In Vitro and Probing

In some embodiments, the invention comprises a method for detecting, labelling, pulling-down or targeting a site in a nucleic acid, comprising: (a) synthesizing an RNA in a cell-free system, (b) contacting the nucleic acid with the RNA and other components by which a complex is formed and said complex does not easily dissociate from the nucleic acid, and (c) analyzing the product of step (b). In some embodiments there is at least one wash step between step (b) and step (c). In some embodiments, at least one component of the resulting complex is labelled or tagged. In some embodiments, the label or tag is on a tail. In some embodiments the Cas9 is an altered version of Cas9. In some embodiments, the guide RNA is a truncated guide RNA. In some embodiments, the truncated guide comprises just the seed region of the guide RNA, i.e. 4-7 nucleotides adjacent to the PAM site.

Nicking and Sequencing

In some embodiments the invention comprises targeted sequencing comprising (a) contacting the nucleic acid with a complex comprising a nicking mutant of Cas9 protein and a guide RNA targeting a specific location under conditions where the complex induces a nick in one strand of the nucleic acid, (b) extending the 3' end of the nick with a nucleotide, (c) detecting the product of step (b) and repeating step (b) in a manner to sequence the DNA. In some embodiments, the nucleotide is labelled. In some embodiments, the nucleotide is labelled at the terminal phosphate. In some embodiments, the nucleotide contains more than three phosphates. In some embodiments, the nucleotide is labelled at the base via a cleavable linkage. In some embodiments, the nucleotide is a reversible terminator. In some embodiments, the label at the base provides the reversible termination. In some embodiments, a modification at the 3' or 2' position on the sugar provides the reversible termination. In some embodiments, all four nucleotides are available for extension at the same time. In some embodiments, the methods of single molecule detection are used. In some embodiments, the single molecule is analysed as a linear string. In some embodiments, the nucleic acid is analysed in a cell in situ. In some embodiments, wherein the nucleic acid is analysed in a cell in situ, the cell is fixed before analysis.

In some embodiments, the nucleic acid analysed in situ is a DNA molecule and RNA molecules are removed before analysis. In some embodiments, reagents are used to remove the complex from the nucleic acid after nicking. In some embodiments, there is at least one wash step between step (b) and step (c). In some embodiments, the Cas9 is an altered version of Cas9. In some embodiments, the guide RNA is a truncated guide RNA. In some embodiments, the truncated guide comprises just the seed region of the guide RNA, i.e. 4-7 nucleotides adjacent to the PAM site.

Nicking and Capture

In some embodiments, the 3' end of the nick is extended with modified nucleotides. In some embodiments, the modified nucleotides are biotin modified. In some embodiments, the incorporated biotins are used to label the target DNA, e.g via interaction with streptavidin/neutravidin or anti-biotin antibody that are themselves labelled (or become labelled). In some embodiments, the incorporated biotins are used to capture the target DNA, e.g via interaction with streptavidin/ neutravidin or anti-biotin antibody that are themselves bound (or become bound) to biotin coated capture material, such as magnetic or agarose beads, or to a surface. In some embodiments, the Cas9/gRNA directed nicking and incorporation of bases that are modified to aid capture, is used to isolate specific single or multiple parts of a nucleic acid sample, in a reaction that is conducted in solution. In this embodiment, for example, after nicking and incorporation of biotinylated dUTP, the product is reacted with streptavidin coated magnetic beads for a length of time (e.g. one hour) that enables the biotinylated parts of the genome to be bound by the streptavidin on the beads. A magnet is then applied and the targeted parts of the genome, which are attached to the solid-phase bead are separated from the supernatant, thereby isolating the targeted regions of interest. The supernatant is discarded. After various degrees of washing stringency and removal of supernatant, the selected genomic DNA is separated from the bead, by methods known in the art (e.g. by heating beyond 90 degrees C.). The captured molecules can then be sequenced, such as by next generation sequencing methods and devices known to those of skill in the art, which may comprise steps selected from, size selection, polishing, barcoding, tailing, library preparation, cluster amplification, rolony amplification etc. The nicking and incorporation approach described herein for selecting or enriching parts or a subset of a nucleic acid sample is advantageous over binding of the guideRNA/Cas9 insofar as the extension allows multiple biotins to be incorporated, thereby improving the efficiency of capture. Another advantage is reduced off-target capture, as three steps are needed before the target becomes capturable: gRNA/cas9 binding, nicking and extension. This selection method is cleaner than existing approaches (e.g. Sureselect) and results in less sequencing, as off target sequences are fewer. In some embodiments, a reaction is conducted on the 5' end of the nick, such as a ligation reaction, such as ligating biotinylated oligonucleotides, as an example. In some embodiments, the sense and antisense strands of a DNA duplex can be separated. According to this aspect, one strand is captured via gRNA/Cas9 binding or via incorporation of biotinylated nucleotides and the other is collected from the supernatant. Alternatively, the strand of the duplex displaced by gRNA binding can be captured by binding to a single-strand binding protein, hydroxyapatite or to a sequence specific oligonucleotide.

Nicking and Direct Sequencing

In some embodiments, the gRNA directed nicking is performed with a target nucleic acid, i.e. DNA, that is attached to a surface or alternatively, after nicking is performed, the DNA is attached to the surface. In some embodiments, the 3' end of the nick can then be used to initiate DNA sequencing. The 3' end of the nick allows polymerase based sequencing, such as Illumina sequencing by synthesis. Both the 3' and 5' ends of the nick support ligation based sequencing such as SOLID (Life Technologies) and sequencing by ligation (Complete Genomics Inc). In some embodiments, the genomic DNA is retained in long lengths and the nicking is conducted before or after it has been attached to a surface. In some embodiments, the DNA is attached to a surface and stretched or elongated so that the sequence or features along its length can be analyzed. Such an analysis may be conducted via optical, electron, X-ray, or scanning probe microscopies. In some embodiments, where the analysis is done via optical methods, Total Internal Reflection or evanescent wave/waveguide imaging is conducted on the sequencing reactions on the polynucleotide disposed on the surface. In some embodiments, the polynucleotides may be linearized but not attached to a surface. In some embodiments, the linearization occurs by the polynucleotide being attached at one end and dangling in a flow stream. In some embodiments, the target nucleic acid, i.e. DNA, is made substantially linear via hydrodynamic drag forces. In some embodiments, the DNA is stretched by nano-confinement by being disposed in a nanoslit, nanochannel or nanogroove. In some embodiments, the linear DNA is substantially straight. In some embodiments, the gRNA directed nicks direct sequencing by synthesis to be conducted at multiple chosen sequence locations on a long linear polynucleotide. In this embodiment, a polymerase enzyme (e.g. 9 Degree North or a mutant thereof or Phi29 or a mutant thereof) extends from the nick by incorporating a nucleotide that is detectable in sequencing by synthesis. This detection can be via pH (as in Ion Torrent sequencing). In some embodiments, detection is via a fluorescent label on the nucleotide. In some embodiments, the nucleotide as well as being fluorescently labeled also acts as reversible terminator and thereby allowing stepwise four color sequencing to be conducted via methods known in the art (such as Illumina or Lasergen sequencing.) The nucleotides that are incorporated may be lightning terminators (Lasergen), wherein the cleavage of the photocleavable moiety is by UV light. In some embodiments, sequencing following the gRNA/Cas9 complex formation is for the purpose of performing selective or targeted sequencing. In other embodiments, the gRNA contains at least a portion of degenerate positions, and sequencing from multiple start sites distributed over the genome is initiated and is not selective for a particular locus. In some embodiments, the nicking occurs while the DNA is inside the cell. In some embodiments, the cell is fixed. For example, the nicking can form part of a Fluorescent in situ sequencing (FISSEQ) reaction, in which DNA is sequenced. In some embodiments, the nicking is used to induced nicks in genomic DNA inside a cell and then to initiate amplification of the region adjacent to the nick, e.g. via branched or rolling circle amplification by a strand displacing polymerase such as Phi29. Sequencing is then conducted on the amplified product. Alternatively, the nicked genomic DNA is sequenced directly from the nick using single molecule sequencing methods, such as TrueSeq (Helicos Bio/SeqLL).

Binding and Nanopore Analysis

In some embodiments the invention comprises a method for detecting the location of a sequence or a binding site in a nucleic acid, comprising: (a) contacting the nucleic acid with a complex comprising a Cas9 protein and a guide RNA under conditions in which the complex does not easily dissociate from the nucleic acid; (b) passing the nucleic acid through a nanopore or nanogap, and (c) analyzing the locations of binding. In some embodiments, the methods of single molecule detection are used. In some embodiments, single channel recording is used. In some embodiments, the single molecule is analysed as a linear string.

Off-Target Binding

In some embodiments the invention comprises a method for detecting guide RNA off-target binding sites comprising: (a) contacting the nucleic acid with a complex comprising a Cas9 protein and a guide RNA under conditions in which the complex does not easily dissociate from the nucleic acid, (b) detecting the locations of binding, (c) determining the targeted location of binding, (d) determining the locations of off-target binding, and (e) determining the identity of the sequences of the off target binding via the locations of the off target binding. In some embodiments, labels are used to provide landmarks by reference to which the target or off target binding can be determined. In some embodiments, the labels comprise binding reagents that create a physical map on the nucleic acid. In some embodiments, the binding reagents may be one or more of a non-promiscuous gRNA, a restriction enzyme, a nickase enzyme, an oligonucleotide etc. In some embodiments, the methods of single molecule detection are used. In some embodiments the single molecule is analysed as a linear string.

Detecting Copy Number

In some embodiments the invention comprises a method for determining the copy number of a chromosome or region of the genome including (a) contacting the target nucleic acid sequence with a guide RNA sequence having a portion complementary to the chromosome or genomic region whose copy number is to be determined and a Cas9 protein, and a portion complementary to a reference chromosome and/or genomic region and Cas9 protein, (b) obtaining a ratio of signal from the chromosome/region of genome whose copy number is to be determined versus the reference chromosome or genomic region. In some embodiments, the method is applied to detection of aneuploidy. In some embodiments, the aneuploidy is trisomy 21. In some embodiments, the locus whose copy number is to be determined is LSI 21q22.13-q22.2.

Her2

In some embodiments the invention comprises a method for determining the extent of Her2 amplification comprising: (a) contacting the target nucleic acid sequence with a guide RNA sequence having a portion complementary to the Her2 locus and a Cas9 protein, and a portion complementary to a reference locus and Cas9 protein, and (b) obtaining a ratio of signal from the Her2 locus compared to the reference locus.

Gene Fusion

In some embodiments, the invention comprises a method for determining the occurrence of a gene fusion including: (a) contacting the target nucleic acid sequence with a guide RNA probe sequence having a portion complementary to the first genomic locus and a Cas9 protein, and a guide RNA probe sequence having a portion complementary to a second genomic locus and Cas9 protein, (b) detecting a co-localization event between the first and second locus, wherein a gene fusion is any fusion between genomic regions. According to one aspect, co-localization results in probes being adjacent to each other.

Break Apart Assay

In some embodiments the invention comprises a method for determining the occurrence of a gene fusion including (a) contacting the target nucleic acid sequence with a guide RNA sequence having a portion complementary to a genomic locus (first locus) and a Cas9 protein, and a guide RNA sequence having a portion complementary (according to a reference) to an adjacent genomic locus (second locus) and Cas9 protein, and (b) determining if a co-localization event between the first and second locus is not detected. In some embodiments, the method is applied to anaplastic lymphoma kinase, such as ALK (See FIG. 12). In some embodiments the method is applied to ROS1. ROS1 is a receptor tyrosine kinase of the insulin receptor family. In some embodiments, the assay is applied in the diagnosis of Non-Small Cell Lung Cancer.

Genomic Re-Arrangements

In some embodiments the invention comprises a method for detecting re-arrangements across genomic region including (a) contacting a genomic DNA sample with a multiple guide RNA sequence each having a portion complementary to specific sub-regions of the genomic region and Cas9 protein, wherein a gRNA for each sub-region comprises an encoding that enables it to be distinguished from gRNA for other sub-regions, and (b) imaging the genomic DNA and decoding the codes and comparing the order of the codes against a reference, wherein there is co-localization of codes over the approximate length of the genomic region of interest. In some embodiments, the gRNA is encoded at the tail. In some embodiments, the decoding of the code is conducted by contacting the encoded part of the tail with decoder molecules such decoder molecules comprising DNA or protein probes. In some embodiments, in addition to determining genomic rearrangements, different alleles for particular genomic segments are also distinguished. In some embodiments, different codes can be used for different alleles, as well as for different genomic segments. In some embodiments, the region of interest is the BRCA1 and/or BRCA2 region(s) of the genome. In some embodiments, the region of interest is the MHC or HLA region. In some embodiments, the region of interest is the region around the MMR genes, MLH1-PMS2 and MSH2-EPCAM-MSH6 and can be used in the diagnosis or analysis of Hereditary Nonpolyposis Colorectal Cancer (HNPCC). In some embodiments, multiple gRNA are used for each genomic segment and each of such multiple guide RNA are labeled with the same code.

Enumerating Repeat Number

In some embodiments, strands of genomic DNA are analyzed as linear strings. In some embodiments, the DNA is stretched. In some embodiments, nanopore/nanogap analysis is conducted. In some embodiments, the method is used for enumerating the number of repeat units on the 3.3 kb-D4Z4 repeat-containing loci on human chromosomes 4 and 10. In some embodiments, the evaluation of the D4ZA region is used to diagnose or analyze patients with Facioscapulohumeral Muscular Dystrophy (FSHD). In some embodiments, the method is used for enumerating telomere sub-unit repeat number. In some embodiments, the method is used for enumerating centromere repeat number. In some embodiments, the method is used for enumerating major satellite repeat number. In some embodiments, the method is used for enumerating minor satellite repeat number.

Cas9/Guide RNA In Situ Hybridization

According to certain aspects, a method for performing Cas9 mediated in situ hybridization includes the steps of contacting the target nucleic acid sequence with a guide RNA sequence having a portion complementary to the chromosomal or genomic region of interest and a Cas9 protein, wherein the guide RNA and the Cas9 protein co-localize to the target nucleic acid sequence to form a complex, wherein the chromosomal or genomic region of interest is disposed in a flow cell, wherein reagents for in situ hybridization and wash reagents are flowed atop the chromosomal or genomic region of interest. According to certain aspects, the location of the complex is detected using methods from the group comprising fluorescence, chemiluminescence, electroluminescence, colorimetric detection and the like.

Allele-Specific Detection

In some embodiments, the invention comprises a method for determining the presence of a specific allele including (a) contacting the target nucleic acid sequence with a guide RNA sequence having its seed portion (first 4-7 nucleotides adjacent to the PAM site) complementary to allele to be detected and Cas9 protein, and (b) detecting the presence of the gRNA/Cas9 co-localized with the nucleic acid.

Binding Assay

According to certain aspects, a diagnostic method for detecting a specific sequence is provided including the steps of (a) contacting the target nucleic acid sequence with a guide RNA sequence having a portion complementary to the target nucleic acid sequence and a Cas9 protein, (b) capturing the complex at a location on a surface, (c) detecting the captured complex at the location via a label only present in the complex and not on the target nucleic acid sequence. According to certain aspects, a diagnostic method for detecting a specific sequence is provided including the steps of (a) contacting the target nucleic acid sequence with a guide RNA sequence having a portion complementary to the target nucleic acid sequence and a Cas9 protein, (b) capturing the complex at a location on a surface, (c) detecting the captured complex at the location via a label only present in the complex and not on cas9/gRNA. In some embodiments, the assay is carried out as part of a lateral flow assay, a dipstick assay, a paper microfluidics assay, a dot blot assay a microarray assay. In some embodiments, the assay is a diagnostic assay.

Immunohistochemistry and gRNA/Cas 9 In Situ Hybridization

In some embodiments, the invention comprises a method of combining immunohistochemistry (IHC) and gRNA/cas9 mediated in situ hybridization (ISH) on the same sample including the steps of (a) contacting the target nucleic acid sequence within target chromatin with a guide RNA sequence having a portion complementary to the target nucleic acid sequence and a Cas9 protein, wherein the guide RNA and the Cas9 protein co-localize to the target nucleic acid sequence to form a complex, (b) contacting the target chromatin with protein binding reagent, and (c) detecting the comparative locations of the guide RNA/cas9 complex and the protein binding reagent. In some embodiments, the protein binding reagent is an antibody. In some embodiments, the protein binding reagent is an aptamer. In some embodiments, the guide RNA/Cas9 complex and the protein binding reagent are differentially labeled. In some embodiments, the IHC reagents and the guide RNA/Cas9 ISH reagents are added together. In some embodiments, the IHC reagents and the guide RNA/Cas9 ISH reagents are added in series, i.e., one after another. In some embodiments, because the guide RNA/Cas9 ISH does not require a denaturation step, the proteins and the chromatin architecture are left intact for IHC to be conducted. In some embodiments, the guide RNA/Cas9 complex is used to isolate a particular portion of chromatin, and the proteins present on the isolated chromatin are detected using an analytical method.

Probing the Guide RNA Tail

In some embodiments, the invention comprises a method of detecting a target nucleic acid sequence including the steps of (a) contacting the target nucleic acid sequence with a guide RNA sequence having a portion complementary to the target nucleic acid sequence and a Cas9 protein, wherein the guide RNA and the Cas9 protein co-localize to the target nucleic acid sequence to form a complex, and wherein the guide RNA includes a 3' tail sequence and said tail is complementary to a probe sequence or can act as a primer, and (b) detecting the complex thereby detecting the target nucleic acid sequence. According to certain aspects, the tail comprises a sequence complementary to a sequence in the close vicinity of the gRNA binding location. According to certain aspects, the tail comprises a sequence complementary to the displaced strand of the duplex. According to certain aspects, one of the target strands of the duplex is sequestered by the guide RNA, leaving the other strand open to bind with other reagents. Exemplary reagents can include a single strand binding protein, a complementary oligonucleotide which may be labeled, or a portion of the tail which is complementary to the strand. According to one aspect, the tail comprises a docking site or handle for DNA PAINT. In some embodiments, the Cas9/guide RNA complex with the other strand is stabilized. In some embodiments, binding single stranded binding protein, such as RPA or binding an oligonucleotide or analog/mimic thereof to the displaced strand, can stabilize the Cas9/guide RNA complex with the other strand. In some embodiments the stabilization effect is due to there being reduced competition from re-zipping of the native duplex.

Cas9 with Altered PAM Specificity

In some embodiments, the invention comprises a method for labelling or targeting a site in a nucleic acid, including the steps of (a) contacting the nucleic acid with a labelled complex comprising Cas9 protein altered to bind adjacent to a non-canonical PAM sequence, and a guide RNA under conditions by which the complex binds to the nucleic acid, and (b) analyzing the product of step (a). According to one aspect, there is optionally at least one wash step between step (a) and step (b) and optionally ancillary reagents are provided to facilitate the binding of the gRNA.

In general for the embodiments described herein, the guide RNA and the RNA may include modified RNA nucleotides known to those of skill in the art. In general for the embodiments described herein, the guide RNA and the RNA may include an RNA/DNA chimera or an RNA/PNA chimera. In some embodiments, the guide RNA or the RNA is made in a cell free system. Methods for making the gRNA or RNA include in vitro transcription and automated chemical RNA synthesis methods known to those of skill in the art. In some embodiments, the gRNA or Cas protein or ancillary proteins are expressed in a cell system and are purified in a cell free system. In some embodiments, the gRNA or RNA is complexed with the Cas protein or ancillary protein in a cell free system.

The following examples are set forth as being representative of the present disclosure. These examples are not to be construed as limiting the scope of the present disclosure as these and other equivalent embodiments will be apparent in view of the present disclosure, figures and accompanying claims.

Example I

Protocols

Protocol for Synthesis of gRNA:
  PCR Assembly is performed as follows.
  Prepare reaction mix including:
  12 µL of Q5 DNA polymerase 2× master mix (NEB)
  3 µL of 10 µM T7 forward primer
  3 µL of 10 µM barcode reverse primer
  3 µL of 10 µM Sp.gRNA.spli60 (forward)
  3 µL of 10 µM gRNA.end (reverse)
  Cycle condition in PCR device:
  1. 98° C. for 30 seconds
  2. 98° C. for 10 sec
  3. 52° C. for 20 sec
  4. 72° C. for 15 sec
  5. Repeat from step 2 for 29 cycles
  6. 72° C. for 2 min
  7. 4° C. hold
  Purify DNA on spin column (Zymo). Typically yield ~1 µg of dsDNA template.
  In vitro Transcription (IVT) in performed as follows:
  Prepare reaction mix including:
  5.8 µl RNase-Free water
  2.5 µl AmpliScribe T7-Flash 10× Reaction Buffer (Illumina)
  1.8 µl 100 mM ATP
  1.8 µl 100 mM CTP (+2 uL Cy3-dUTP)
  1.8 µl 100 mM GTP
  1.8 µl 100 mM UTP
  2 µl 100 mM DTT
  0.5 µl RiboGuard RNase Inhibitor
  5 µl DNA template
  2.0 µl AmpliScribe T7-Flash Enzyme Solution
  Guide RNA can also be synthesized with modified NTP in which case the following modification is performed:
    add 1:1 molar ratio of the NTP to be modified and the modified-NTP (e.g. 0.9 µl UTP and 0.9 µl UTP-Cy3).
  Incubate at 37° C. for 2 h to 16 h in PCR device, then hold 4° C. Purify RNA on spin column (Zymo).
  Typically yield ~100 µg of RNA (i.e. barcoded gRNA).

Protocol for Cas9-gRNA Complex Assembly:
  For reference, 1 µg of gRNA with a single barcode on a tail is 25 pmol of RNA. Cas9 protein and gRNA are typically mixed at a 1:1 molar ratio, to form the Cas9-gRNA complex. The same reaction conditions can be used for complexing wild type Cas9, nickase Cas9 and nuclease null or dead Cas9. MgCl can be omitted when the wild type Cas9 is used and the aim is to prevent cleavage. Plasmids for expressing, wild type Cas9, nuclease null Cas9 and Cas9 nickase are available from Addgene. The plasmids can be expressed in a suitable host and the proteins can be purified by methods known in the art, such as the use of His tags in the expressed protein. Higher ratio of Cas9 to gRNA (e.g. 3:1) can be used to ensure that more gRNA are complexed with Cas9. The active complex is typically formed by pre-incubating at 37° C. for 15 minutes. The reaction buffer can vary. Exemplary buffers include 20 mM HEPES, 100 mM NaCl, 5 mM $MgCl_2$, 0.1 mM EDTA, pH 6.5; 20 mM Tris-HCl, 100 mM KCl, 5 mM $MgCl_2$, 5% glycerol, 1 mM DTT, pH 7.5; and 1×PBS, 5 mM $MgCl_2$, 0.5% Tween-20, pH 7.0. The active complex can be used immediately or stored at 4° C. for several weeks.

Cas9-gRNA Fluorescence In Situ Assay:
  According to this assay, the samples have been fixed to a microscope slide (or coverslip slide). The slides can be incubated in a Coplin jar, or assembled in a flow chamber or flow cell to minimize reaction volume even more and automate the process. The reaction is performed in the following order and slides are incubated in a coplin jar, unless otherwise noted (for flow chambers, information is provided in parenthesis). Incubate for 2 minutes with 1×PBS with 0.5% Tween-20 (wash with two flow chamber volumes, incubate for 30 second, between each washes). Incubate for 5 minutes with 1×PBS with 0.5% Triton X-100 (wash with two flow chamber volumes, incubate for 2 minutes, between each washes). Incubate for 5 minutes with 0.1 N HCl (wash with two flow chamber volumes, incubate for 2 minutes, between each washes). Incubate for 2 minutes with 1×PBS with 0.5% Tween-20 (wash with two flow chamber volumes, incubate for 30 second, between each washes). Incubate for 5 minutes in Cas9 buffer (wash with two flow chamber volumes, incubate for 30 second, between each washes). This time can be used to pre-complex Cas9-gRNA in Cas9 buffer at 37° C., or warm up the refrigerated complex to 37° C. Typically, 5 µM of gRNA and 5 µM of Cas9 are complexed together in 25 uL volume per sample. Add 25 uL Cas9-gRNA complex in Cas9 buffer, and incubate in a humidity chamber at 37° C. for 4 h. Alternatively, seal with removable rubber cement and incubate at 37° C. Wash by incubating for 2 times for 5 minutes in Cas9 buffer at 37° C. (wash with four flow chamber volumes, incubate for 30 second, between each washes). Incubate for 2 minutes with 1×PBS with 0.5% Tween-20 (wash with two flow chamber volumes, incubate for 30 second, between each washes). Optional: if necessary, probe by adding 1 µM oligo probes to 20 µL 2×SCC with 0.5% Tween-20 to each sample, and incubate in a humidity chamber at for 15 min. Alternatively seal with removable rubber cement before incubation. Wash by incubating for 2 times for 2 minutes in 1×PBS with 0.5% tween-20 (wash with four flow chamber volumes, incubate for 30 second, between each washes). Mount with 10 uL anti-fade microscopy medium with DAPI and seal with nail polish (e.g. AntiFade or VectaShield). Slides are ready for imaging or can be stored in the dark for a week. In some cases the HCL step can be omitted.

Flow Cell

A flow cell can be made by using double sided tape or sheets (From Adhesive Research or 3M) to make barriers, which is sandwiched between the coverglass or slide containing the sample of interest and a second coverglass or slide. A system for making a flow cell is commercially available from Ibidi can be used (sticky-Slide VI$^{0.4}$ or sticky-Slide I Luer). Here the slide or cover glass on which the cells, chromosomes or DNA is deposited, is attached to the sticky part of the flow cell to create a flow cell atop the substrate. Reagents are flowed into the flow cell by manual pipetting into the inlet area and wicking (e.g. using blotting paper) in the outlet area. Alternatively, reagents are flowed in via an automated reagent flow and exchange system to move fluid and multi-way valve. This can be accomplished by using a syringe pump, pressure driven flow and suction. The automated system is integrated with a microscope or an imaging instrument, wherein the flow cell is loaded.

Molecular Combing of DNA

Male Genomic DNA (Promega or Novagen) or DNA extracted from cells using the gel plug method for example, is combed onto coverglass coated with vinyl silane (7-Octenyltrichlorosilane). This is done by dipping the coverglass (e.g. 22×22 mm) into a trough containing the DNA in 0.5M MES buffer solution that covers the majority of the coverglass (e.g. 1-1.5 ml for a 22×22 coverglass), allowing the DNA ends to bind to the surface coating (1 min-10 min, typically) and then withdrawing the coverglass from the trough. The concentration of DNA in the trough can be adjusted to give the desired density of combed DNA. For example, a concentration up to 0.5 ng/ul can give a reasonable density where individual stretched DNA molecules can be resolved. The coverglass is then withdrawn at a constant speed (e.g. 300 µm/s) from the DNA solution, allowing the DNA to become stretched due to the force of the receding meniscus, as the coverglass is withdrawn. Optionally, the DNA is then crosslinked onto the coverglass using approximately 10-20 Joules per cm2 of Ultra-violet radiation energy. Optionally, a flow cell is formed on the coverglass as described above. The combed DNA can be visualized by staining with one or more intercalating dyes such as YOYO-1 either during the combing process or after. A DNA base pair to YOYO-1 staining ratio between 5:1 and 10:1 is typically used.

Cas9/gRNA Binding to DNA Pre-Stretched on a Coverglass

A coverglass with combed genomic DNA sandwiched to make a flow cell is first hydrated by washing with PBS tween and PBS. Optionally, the substrated is blocked with Blockaid (Life Technologies). Optionally, the flow cell is washed through with the Cas9 reaction buffer. The Cas9-gRNA are pre-complexed at 37 degrees C. and then added to the flow cell and left to incubate for 30 minutes to one hour. The reaction is stopped by washing through with buffers such as reaction buffer and PBS tween20 and PBS.

Figure 6B:
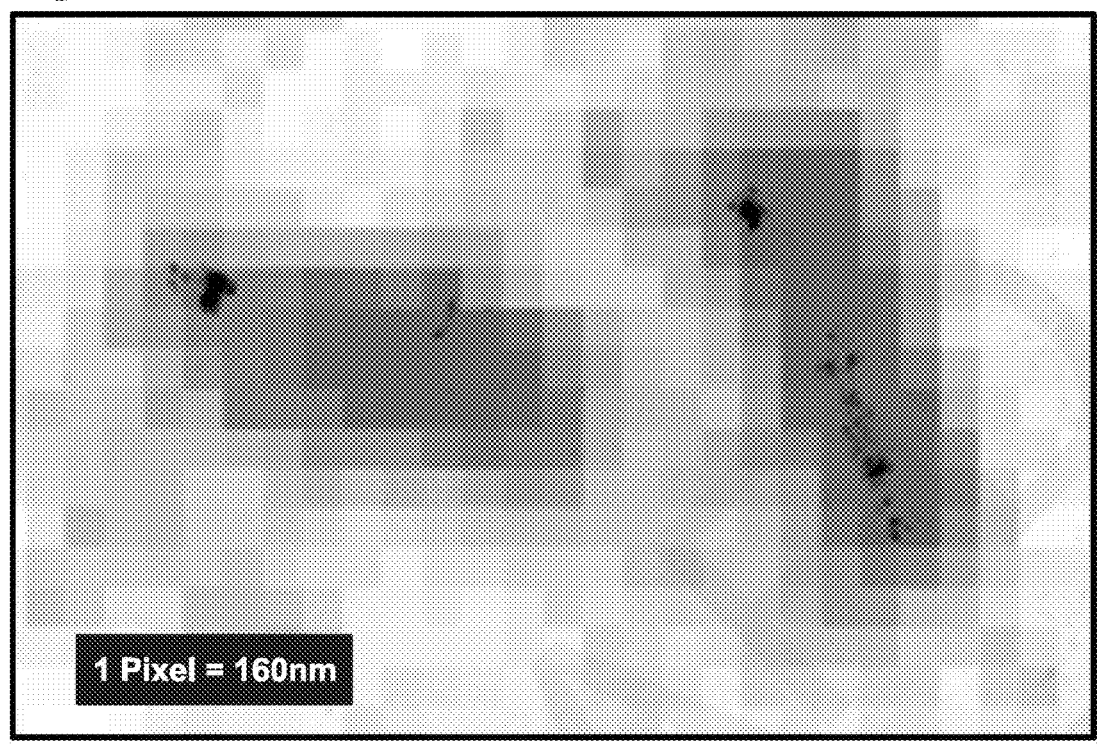

The guide RNA used for FIGS. 6A and 6B is Centromere 16 gRNA with Tail:

```
                                      (SEQ ID NO: 8)
GACGCCUUCGUUGGAAACGUUUUAGAGCUAGAAAUAGCAAGUUAAAAUAA

GGCUAGUCCGUUAUCAACUUGAAAAAGUGGCACCGAGUCGGUGCUUUUUT

CCTCTACCACCTACATCACTTATACATCTA
```

Hybridization of Fluorescently Labeled Probe to Tail

Ensuring the flow cell remains hydrated and after the Cas9/gRNA complex has formed, the complex is imaged by adding a DNA probe to the tail in the following hybridization buffer: 200 ul formamide, 20 ul sds, 120 ul blockaid, 40 ul of 20×ssc, and 20 ul water.

The sequence used for probing the tail is.

```
                                      (SEQ ID NO: 9)
        TAGATGTATAA GTGATGTAGGTGGTAGAGGA
```

This can be left at 4 degrees C. overnight. Other hybridization temperatures and hybridization buffer compositions can also be used depending on the thermal stability of the probe to tail hybrid.

Labelling can be done at one or both ends with a fluorescent label such as Atto 647N, Atto 655, Alexa 647. Superresolution imaging can be carried out by the STORM method when an appropriate fluorescent label is used (e.g. Atto 655).

Hybridization of Probe to Tail and Imaging

DNA PAINT imager probes are added to the imaging solution in a hybridization buffer to obtain the stochastic on and off pattern needed for superresolution. A PAINT sequence that is complementary to a sequence on the tail or is complementary to a sequence on a probe that binds to the tail and that was used in FIG. 6A and FIG. 6B and similar experiments was /5Alex647N/TAGATGTATAAAAAAATTTAATAAGGT/3AlexF647N (SEQ ID NO: 10)
or
/5ATTO647NN/TAGATGTATAAAAAAA/3ATTO647NN/ (SEQ ID NO: 11)

Imaging is accomplished using a 633, 640 or 647 nm laser line and a filter block appropriate for Cy3 on a Nikon Ti-E inverted microscope in Total Internal Reflection (TIRF) mode and captured on back thinned Andor Ixon X3 EMCCD camera.

Superresolution Imaging

Superresolution imaging as shown in FIG. 6b can be conducted by performing the DNA PAINT procedure using the following imager strand: P9 imager: ACCTTATTA. This binds to a tail that contains the P9 handle (docking sequence) or to a probe that has already bound to the tail that contains the P9 handle: TAATAAGGT. A suitable buffer for imaging DNA PAINT is 5 mM Tris pH 8, 10 mM MgCl2, 1 mM EDTA pH 8 and 0.05% Tween-20. A movie can be taken for 15 minutes to 30 min using Nikon NIS Elements software and the superresolution image can be constructed using DNA PAINT Image Analysis code written in LabVIEW (See Jungmann et al Nano Lett., 2010, 10 (11), pp 4756-4761.

Binding Cas9/gRNA to Genomic DNA in Solution

The Cas9-gRNA complex assembly (pre-incubated at 37 degrees C. for 10 min) is added to DNA in the presence of buffer solution and incubated at 37 degree C. for one hour. The DNA with Cas9/gRNA bound is optionally purified. Then, if DNA stretching is desired the reaction is diluted in 0.5M MES solution and the DNA with gRNA/cas9 complex decorated thereon is combed onto a vinyl silane coverglass surface. This approach was used in FIG. 6C.

Purification of Complexed DNA

Depending on the size of the guide RNA used, a number of different purification methods can be used to isolate the target DNA/gRNA/Cas9 complex including, size exclusion, affinity purification (e.g. using desthiobiotin or cleavable linker binding to streptavidin bead), or dialysis membrane.

Cas9 Nicking and Targeted Sequencing

Cas9-gRNA binds to dsDNA template at a specific location on the target DNA. The target DNA can be in a native genome and the reaction is performed in vivo. The target DNA can be in cells or an organism is fixed to a surface and the reaction is performed in situ. In these cases, it is preferable that the spatial location of the genome remains preserved. Furthermore, the target DNA can be extracted and the reaction is performed ex vivo. The extracted target DNA can also be immobilized on a surface or in a fluidic system (e.g. a nanochannel) and the reaction is performed ex vivo.

Figure 9:
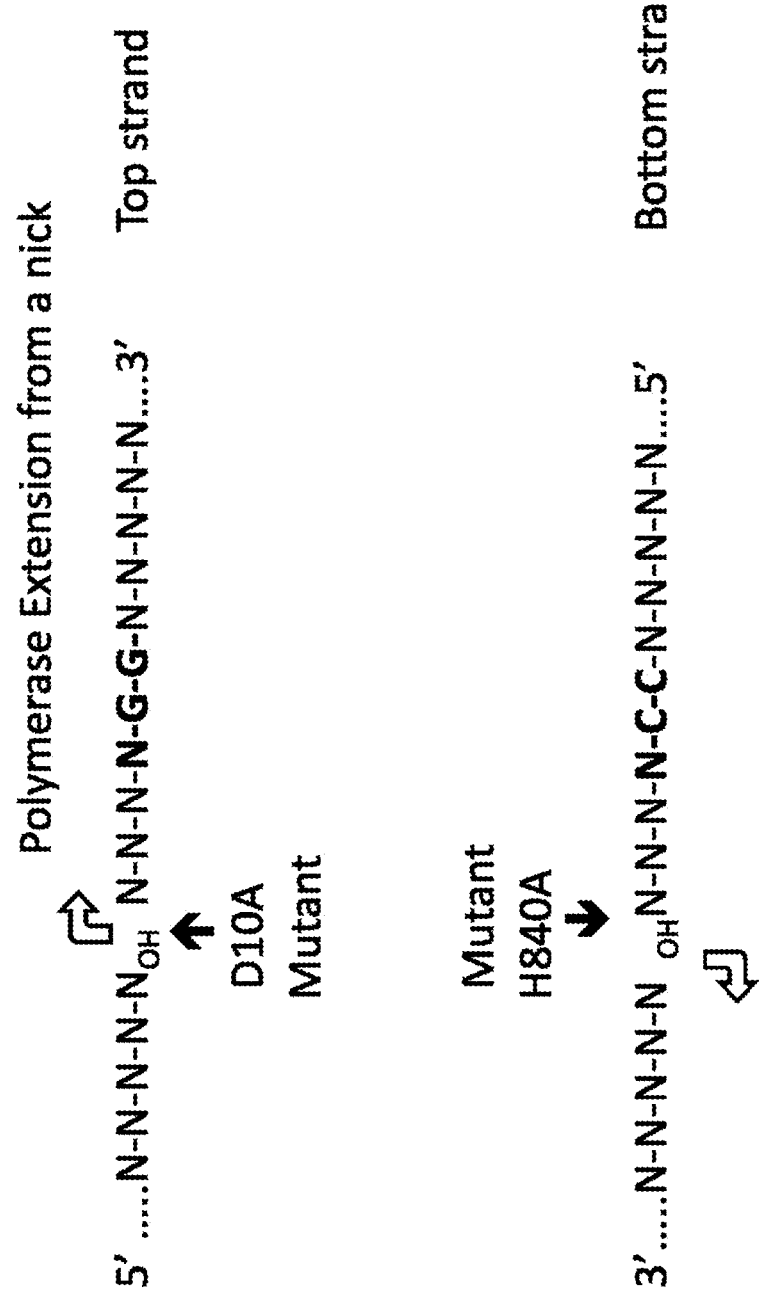
FIG. 9A-9B present a diagram for initiating sequencing from a nick site. (SEQ ID NO:1-2)

A gRNA/Cas9 mediated nicking reaction is conducted using a mutant nickase (e.g. Cas9 carrying either the D10A or H840A mutants). See FIG. 9. The RuvC domain of Cas9 can be inactivated by a D10A mutation and the HNH domain can be inactivated by an H840A mutation.

One of two nicking mechanisms can be used, one on the top strand which base-pairs with gRNA, the other on the bottom strand, the displaced strand. Mutation at position D10A allows nicking of the top strand but not the bottom. Mutation at the H840A position allows nicking of the bottom strand and not the top. Cleavage occurs 3 bp upstream of the protospacer adjacent motif (PAM) by Cas9 (D10A) nickase. Cas9(H840A) cleavage occurs at the complementary location on the bottom strand. Compared to nicking endonucleases, which recognize specific short sequences that occur many times in the genome, gRNA nicks at comparatively long recognition sequences, which may occur only once in the genome. This can be used to target specific unique sequences in the genome. Targeted sequencing can be conducted by the steps: choosing either the D10A nickase or the H840A nickase; choosing a guide RNA in the vicinity of the region to be sequenced; carrying out gRNA/Cas9 reaction to for a complex with the chosen gRNA and Cas9 mutant; optionally removing the Cas9/gRNA complex from the target DNA; addition of polymerase and fluorescently labeled reversible terminator nucleotides in appropriate buffer to conduct sequencing cycles of incorporation, washes and cleavage. This enables the targeted location to be sequenced.

In some embodiments, the Cas9-gRNA complex may be removed from the target DNA and from the sample entirely. The removal agent can be a detergent (e.g. sodium dodecyl sulfate), an organic compound (e.g. urea, Guanidinium chloride/thiocyanate), an amide (e.g. formamide), a proteolytic enzyme (e.g. protease), a physical property (e.g. temperature) or a combination thereof.

If Cas9(D10A) is used, sequencing proceeds through the PAM locus and proceeds downstream of the locus, sequencing the strand containing the PAM. If the Cas9(H840A) is used, sequencing proceeds in the upstream direction of the PAM locus and sequences the strand complementary to the NGG PAM sequence. To avoid sequencing through the guide RNA sequence the D10A mutant can be chosen. Multiple guides can be chosen over the region of interest.

If stepwise sequencing by synthesis is conducted, each incorporated nucleotide bears a reversible terminator, the result of incorporation of a single nucleotide at each targeted location is detected (preferably by using TIRF illumination and a CCD or CMOS detector) before removal of the terminator and label and repeating the cycle for the next base at each targeted position.

Various Illumina SBS kits (e.g SBS Kit 2) can be used for sequencing with reagent addition and imaging in the following order: Universal Sequencing Buffer; Incorporation Mastermix; Universal Sequencing Buffer; IMAGING TARGETED LOCI; Universal Scan Mix; Cleavage Reagent Mastermix; Cleavage Wash Mix. Details of the Illumina kit can be downloaded from the world wide website support.illumina.com/downloads/hiseq-rapid-sbs-kit-v2-reagent-prep-guide-15058772.html. Imaging is done by using 532 nm laser for two of the four dyes and 660 nm laser for the other two of the dyes on the nucleotides. Each of the two dyes excited by each laser are differentiated by using specific emission filters and an algorithm designed to determine the signatures of each dye.

One of a number of different Illumina sequencing instruments can be used including the Genome Analyzer IIx. A flow cell footprint compatible with the Illumina flow cell holder and inlet and outlet ports can be used. Alternatively, a home-built system comprising an inverted microscope, with high numerical aperture objective lens, lasers, CCD camera, fluorophore selective filters and syringe pump based or pressure driven reagent exchange system and a heated stage. The home-built system can be adapted for other nucleotide/dye combinations than offered by Illumina.

If the sequencing is done as a real-time reaction (e.g. PacBio or Starlight sequencing) the nucleotides are labeled at the terminal phosphate which is a natural leaving group once the nucleotide has been incorporated. Such a reaction is continuously monitored on CCD or a CMOS camera.

Targeted Sequencing on Stretched DNA Duplex

Genomic DNA can be extracted from cells and retained in long lengths (e.g. by performing extraction in gel plugs) so that the linear location of the sequence is preserved. This has important utility for determining the organization of sequences in the genome. Structural variation (SV) in the organization of the genome can lead to disease, as demonstrated by the ALK, BRCA, FSHM and HER2 examples described herein. However, certain SV such as the Bcr-ABL translocation in leukemia can be targeted by drugs such as Gleevac, so it is important to determine if a leukemia patient has the translocation that can be targeted by this drug.

Preferably the sequencing is done on stretched DNA using molecular combing for example, so that the linear organization in the genome of the targeted sequences can be visualized. The targeted regions can be selected by using a nicking mutant Cas9 and gRNA designed to bind at the locations of interest, performing the nicking reaction and then extending from the nick. The nicking reaction can be conducted in solution before combing of the DNA. Alternatively, the nicking reaction can be conducted after DNA has been combed, using a flow cell on top of the combed DNA. The sequencing reactions proceed initially by hydrating and pre-conditioning the DNA with incorporation buffer and then by flowing sequencing reagents into the flow cell. The result is that not only is the sequence of the target region obtained, but also its location in the genome. An example of when this is important is when gRNA based targeting of sequencing is directed to a sequence in the genome that is a hotspot for translocation, but it is not known where in the genome it has translocated to and what sequence it has fused with.

Targeted Sequencing In Situ

Methods described herein are directed to determining the spatial location of parts of the genome within a cell or nucleus and how such spatial location affects gene regulation and genome function. The spatial location in the cell of specific genomic sequences can be targeted using gRNA specific to those sequences. gRNA/Cas9 mediated nicks are created on the genomic DNA in the fixed cells and fluorescence-based sequencing is conducted on the genomic DNA in situ. As described in Lee et al, 2015: (Nat Protoc. 2015, 10(3):442-58,) cells are grown on glass-bottom dishes and tissue sections are mounted by methods known in the art. The cells are fixed (e.g. using 10% formalin in PBS for 15 min at 25° C., or 100% methanol at −20° C. for 20 minutes). Washes are conducted in PBS with Triton X-100 and with PBS alone. Urea is optionally added to remove the gRNA/Cas9 from the nicked DNA. Optionally RNA is removed by using RNases.

Sequencing can be conducted directly on a single molecule of the genomic DNA within the cell. Nucleotides are incorporated at the site of nicks using a polymerase. Preferably, the nucleotides bear fluorescent labels with fluorophores providing high quantum yield, such as Cy3B or multi-labeled nucleotides. Washes of various stringencies known in the art are used to reduce signal form un-incorporated nucleotides. Imaging is conducted via a single molecule imaging method but because only part of the cell is in contact with a surface, TIRF imaging can only access a sub-fraction of incorporation signals. Confocal microscopy or light-sheet microscopy can be used to access signals that are distributed over 3D space within the cells and tissues. Multi-photon or two-photon laser microscopy is used to access signal, especially when it is deep lying. Such methods are also effective in reducing background signals.

After PBS washes, the buffer used in the sequencing reaction is used for conditioning the sample before the sequencing reaction mix is added. Depending on the primers used, the imaging set up and whether temperature control is available, either SOLID chemistry, CycLic chemistry, SBL chemistry or a sequencing by synthesis chemistry such as Illumina sequencing or Lasergen sequencing is applied for incorporation of nucleotides and cleavage of labels and terminators. Images are taken after each incorporation step. The images are processed to produce punctuate signals. Images from each consecutive cycle are registered. Base calls are made upon each image and the base calls are stacked to provide sequence reads at each foci. Non-specific signals can be filtered out by only including sequences in the process of read build-up, that are coincident over many registered images. Bowtie 1.0 or other sequence alignment algorithm is used to align reads to a reference, and to further filter out noise or off-target sequences that are not of interest. The distinct foci of the sequencing reads are visualized to provide information of the spatial localization of the targeted sequences within the cell. Sequencing, rather than just labeling of the targeted locations, has the potential to reveal sequence variants, within the regions of interest as well as their spatial location.

Nanopore Analysis of gRNA/Cas9 Complex Along Nucleic Acid Polymer

SiN membranes are fabricated, and 20 nm diameter nanopores are drilled with a transmission electron microscope (TEM) (Janssen, X. J. A.; Jonsson, M. P.; Plesa, C.; Soni, G. V.; Dekker C.; Dekker, N. H. Nanotechnology 2012, 23 (47), 475302). Membranes are then painted with a layer of polydimethylsiloxane (PDMS) to reduce capacitance and improve the signal-to-noise ratio. Membranes are mounted in a flow cell, containing a top and bottom reservoir separated by the membrane, after which the two reservoirs are filled with 1 M KCl, 10 mM Tris, 1 mM EDTA at pH 8. The nucleic acid polymer is added to the top reservoir and a voltage is applied between the top (−ve) and bottom (+ve) reservoir, allowing electrophoretic driven transport of the nucleic acid polymer through the pore, substantially in a linear manner. The current is recorded with an ion channel recording system including an Axopatch 200B amplifier and a Digidata 1322A DAQ digitizer. The recordings are analyzed using the Transalyzer Matlab package (See Plesa, C.; Dekker, C. Nanotechnology 2015, 26 (8), 084003). The data is analyzed for an increase in current blockage as the nucleic acid polymer enters the nanopore and then further punctuate elevations in blockage as the gRNA/Cas9 bound regions pass the narrow constriction of the pore.

Example II

Creating Cas9-gRNA Complex for Her2/Erbb2 Diagnostic

Her2 (also known has Erbb2 by the Human Genome Organization Gene Nomenclature Committee) gene sequence is available from different online repository, such NCBI world wide website ncbi.nlm.nih.gov/gene/2064.

Her2 sequence is analyzed to find PAM motif along the dsDNA. The preferred motif is 5'-GG-NNNNNNNNNNNNNNNNNGG-3' (SEQ ID NO:12). The 5' GG provide optimal RNA synthesis via T7 RNA polymerase. The 3' NGG is the PAM sequence recognized by Cas9. The 17 bases N in between are for the targeted sequence and provide high specificity. Exomes are preferred because the method can distinguish between gene variants (i.e. isoforms).

Figures 10, 11:
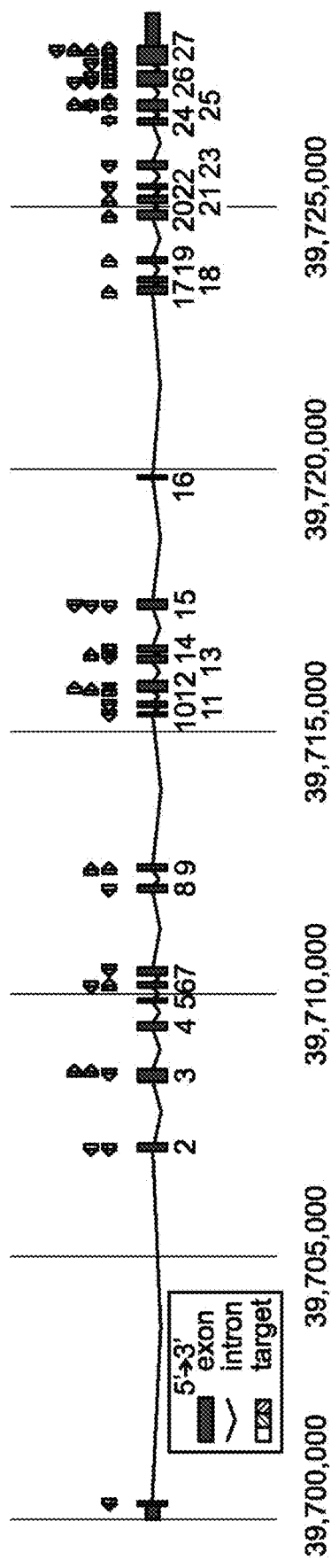
FIG. 10 presents an output diagram identifying gRNA/Cas9 target sites to identify Her2, using CHOPCHOP.
FIG. 11 presents a PCR assembly strategy to make a gRNA template from an ensemble of oligonucleotides. (SEQ ID NO:3-6)

A number of programs are freely available on the internet to find the target sequences. FIG. 10 shows a diagram of the output provided when using CHOPCHOP (See Tessa G. Montague; Jose M. Cruz; James A. Gagnon; George M. Church; Eivind Valen. (2014). CHOPCHOP: a CRISPR/Cas9 and TALEN web tool for genome editing. Nucleic Acids Res. 42. W401-W407).

A partial list of target sequences for Her2 is presented in Table 1. This table also contains information about the location of the target on the human genome, the exon number, the DNA strand (i.e. sense (+) vs antisense (−)), and the potential number of secondary targets elsewhere in the genome (i.e. Mismatches, MM)

TABLE 1

| | Target sequence | Genomic location | Exon | Strand | MM |
|---|---|---|---|---|---|
| 1 | GGGCGAGGAGGAGCCCCCAGCGG | chr17:39700259 | 1 | − | 0 (SEQ ID NO: 13) |
| 2 | GGTGGCGGAGCATGTCCAGGTGG | chr17:39707039 | 2 | − | 0 (SEQ ID NO: 14) |
| 3 | GGTGGGTCTCGGGACTGGCAGGG | chr17:39707021 | 2 | − | 0 (SEQ ID NO: 15) |
| 4 | GGCAGCCCTGGTAGAGGTGGCGG | chr17:39707054 | 2 | − | 0 (SEQ ID NO: 16) |
| 5 | GGAGGCCCCTGTGACAGGGGTGG | chr17:39708472 | 3 | − | 0 (SEQ ID NO: 17) |
| 6 | GGGCCTCCCCAGGAGGCCTGCGG | chr17:39708487 | 3 | + | 0 (SEQ ID NO: 18) |
| 7 | GGCCTCCCCAGGAGGCCTGCGGG | chr17:39708488 | 3 | + | 0 (SEQ ID NO: 19) |
| 8 | GGTGGCTGTGCCCGCTGCAAGGG | chr17:39710106 | 6 | + | 0 (SEQ ID NO: 20) |
| 9 | GGGCAGTGGCCCCTTGCAGCGGG | chr17:39710116 | 6 | − | 0 (SEQ ID NO: 21) |
| 10 | GGGACAGGCAGTCACACAGCTGG | chr17:39710458 | 7 | − | 0 (SEQ ID NO: 22) |
| 11 | GGTTGTGCAGGGGGCAGACGAGG | chr17:39711962 | 8 | − | 0 (SEQ ID NO: 23) |
| 12 | GGGCATGGAGCACTTGCGAGAGG | chr17:39712335 | 9 | + | 0 (SEQ ID NO: 24) |
| 13 | GGAGCACTTGCGAGAGGTGAGGG | chr17:39712341 | 9 | + | 0 (SEQ ID NO: 25) |
| 14 | GGAGCTGCTCTGGCTGGAGCGGG | chr17:39715307 | 10 | − | 0 (SEQ ID NO: 26) |
| 15 | GGAAGACGCTGAGGTCAGGCAGG | chr17:39715477 | 11 | − | 0 (SEQ ID NO: 27) |
| 16 | GGTGGGTGTTATGGTGGATGAGG | chr17:39715824 | 12 | − | 0 (SEQ ID NO: 28) |
| 17 | GGCTGGGGCTGCGCTCACTGAGG | chr17:39715781 | 12 | + | 0 (SEQ ID NO: 29) |
| 18 | GGTGCGGGTTCCGAAAGAGCTGG | chr17:39715875 | 12 | − | 0 (SEQ ID NO: 30) |
| 19 | GGCTGGGCATCAGCTGGCTGGGG | chr17:39715766 | 12 | + | 0 (SEQ ID NO: 31) |
| 20 | GGGCTGGGCATCAGCTGGCTGGG | chr17:39715765 | 12 | + | 0 (SEQ ID NO: 32) |
| 21 | GGAGGAATGCCGAGTACTGCAGG | chr17:39716410 | 13 | + | 0 (SEQ ID NO: 33) |
| 22 | GGCATTCCTCCACGCACTCCTGG | chr17:39716398 | 13 | − | 0 (SEQ ID NO: 34) |
| 23 | GGCTGACACTCAGGGTGGCACGG | chr17:39716552 | 14 | − | 0 (SEQ ID NO: 35) |
| 24 | GGTCAGGTTTCACACCGCTGGGG | chr17:39717382 | 15 | − | 0 (SEQ ID NO: 36) |
| 25 | GGGCAGCGGGCCACGCAGAAGGG | chr17:39717362 | 15 | − | 0 (SEQ ID NO: 37) |
| 26 | GGGGCAGCGGGCCACGCAGAAGG | chr17:39717363 | 15 | − | 0 (SEQ ID NO: 38) |
| 27 | GGTTGGCATTCTGCTGGTCGTGG | chr17:39723346 | 17 | + | 0 (SEQ ID NO: 39) |
| 28 | GGAGAATGTGAAAATTCCAGTGG | chr17:39723932 | 19 | + | 0 (SEQ ID NO: 40) |
| 29 | GGGCATCTGCCTGACATCCACGG | chr17:39724776 | 20 | + | 0 (SEQ ID NO: 41) |
| 30 | GGATGTGCGGCTCGTACACAGGG | chr17:39725066 | 21 | + | 0 (SEQ ID NO: 42) |
| 31 | GGTGAACCGCCGGCGGAGAATGG | chr17:39725355 | 22 | − | 0 (SEQ ID NO: 43) |
| 32 | GGTCAGGGATCTCCCGGGCTGGG | chr17:39725759 | 23 | − | 0 (SEQ ID NO: 44) |
| 33 | GGATGACCACAAAGCGCTGGGGG | chr17:39726635 | 24 | − | 0 (SEQ ID NO: 45) |
| 34 | GGATGATTGACTCTGAATGTCGG | chr17:39726565 | 24 | + | 0 (SEQ ID NO: 46) |

TABLE 1-continued

| | Target sequence | Genomic location | Exon | Strand | MM | |
|---|---|---|---|---|---|---|
| 35 | GGTGTCTGAATTCTCCCGCATGG | chr17:39726605 | 24 | + | 0 | (SEQ ID NO: 47) |
| 36 | GGACAGAAGAAGCCCTGCTGGGG | chr17:39726920 | 25 | - | 0 | (SEQ ID NO: 48) |
| 37 | GGGGGACCTGGTGGATGCTGAGG | chr17:39726886 | 25 | + | 0 | (SEQ ID NO: 49) |
| 38 | GGACGATGACATGGGGGACCTGG | chr17:39726874 | 25 | + | 0 | (SEQ ID NO: 50) |
| 39 | GGTGGATGCTGAGGAGTATCTGG | chr17:39726895 | 25 | + | 0 | (SEQ ID NO: 51) |
| 40 | GGCACCGCAGCTCATCTACCAGG | chr17:39726981 | 25 | + | 0 | (SEQ ID NO: 52) |
| 41 | GGAGTATCTGGTACCCCAGCAGG | chr17:39726907 | 25 | + | 0 | (SEQ ID NO: 53) |
| 42 | GGACCATGCCCCCAGCGCCCGGG | chr17:39726952 | 25 | - | 0 | (SEQ ID NO: 54) |
| 43 | GGGTGCCAGTGGAGACCTGGGGG | chr17:39727344 | 26 | - | 0 | (SEQ ID NO: 55) |
| 44 | GGCGGTGGGGACCTGACACTAGG | chr17:39727298 | 26 | + | 0 | (SEQ ID NO: 56) |
| 45 | GGGGAGGCTTTGCAGCCCCTTGG | chr17:39727419 | 26 | - | 0 | (SEQ ID NO: 57) |
| 46 | GGTCCTGGTCCCAGTAATAGAGG | chr17:39727933 | 27 | - | 0 | (SEQ ID NO: 58) |
| 47 | GGGACCAGGACCCACCAGAGCGG | chr17:39727944 | 27 | + | 0 | (SEQ ID NO: 59) |
| 48 | GGTGTCCCTTTGAAGGTGCTGGG | chr17:39727976 | 27 | - | 0 | (SEQ ID NO: 60) |
| 49 | GGGGGCTGGGGCCGAACATCTGG | chr17:39727703 | 27 | - | 0 | (SEQ ID NO: 61) |
| 50 | GGCCCAAGACTCTCTCCCCAGGG | chr17:39727782 | 27 | + | 0 | (SEQ ID NO: 62) |

It should be noted that regions outside the gene can as easily be targeted. Specific regions such as exons and introns are targeted, which can be less than 1 kb to a full gene of 30 kb, tens or hundreds of kilobases, or several megabases.

The sequence targets are used as a template to prepare the gRNAs. This involves adding each target sequence to a gRNA scaffold. A diagram of an assembly model is provided below, and the assembly is done using PCR with a high-fidelity DNA polymerase (Melting temperature (Tm) are provided). Briefly, oligonucleotides are acquired from a commercial vendor or synthesized in-house. There are 2 universal oligonucleotides: Fwd-T7-gRNA, a forward PCR primer which also include a portion of the T7 RNA polymerase recognition motif; and gRNA.split60 the universal gRNA scaffold. Additionally, there are 2 variable oligonucleotides: Sp.gRNA.split60, the sequence specific for the target of interest; and Rev-B1-gRNA.18, a reverse PCR primer which also include a barcoded handle for multiplex strand detection.

This design allows for cost efficient synthesis and assembly of gRNA, while providing optimum sequence accuracy for oligonucleotides synthesized via phosphoramidite chemistry, and addition of various type of barcode handles, which are codes to which labelled entities can be docked. The DNA templates can be synthesized at different scales, including on an oligonucleotide array synthesizer, or acquired commercially. The templates can be amplified and re-amplified by PCR to generate and perpetuate the templates, which is more cost effective than de novo synthesis.

An exemplary PCR assembly depicted in FIG. 11 can take less than an hour. Following PCR, gRNA are synthesized by in vitro transcription (IVT) by adding a T7 RNA polymerase mix to the template DNA. In this case, longer reactions will provide more gRNA. A rapidly produced Cas9-gRNA kit for a limited number of use can be made within half an hour. A large quantity can be produced with a reaction proceeding for 16 hours. After IVT, the DNA template is degraded by DNaseI treatment and the RNA is purified, either by using a commercial column purification kit or by ethanol precipitation in the presence of ammonium acetate.

The barcoded-gRNA are then complexed in a 1:1 ratio with Cas9 protein in the presence of magnesium ions to form the Cas9-gRNA complex. The reagents can then be used. The detection probe, which is a labeled oligonucleotide that binds to the barcode to facilitate decoding the barcode can also be added at this stage, which allows for a faster hybridization detection method downstream. That decision is made based on the expected signal-to-noise ratio. By example, if low noise is expected (e.g. detection of Her2 on chromosome spread on the surface of a microscope slide), then the Cas9-gRNA-label kit can simply be added to the sample, allowed to react at 37° C. Unreacted complexes are washed and the sample can be imaged. A kit is an ensemble of all the Cas9-gRNA complexes required to probe the locus. A Cas9-gRNA-label kit is the ensemble of all the pre-labeled Cas9-gRNA.

Example for Encoding Cas9-gRNA for Multiplex Detection.

One or multiple code or barcode handles (docking sites for probe) can be added to the gRNA. The principle is to determine the identity of the Cas9-gRNA complexes associated to the DNA sample. This is done by hybridizing a detectable "decoder" probe specific to the gRNA handle. The gRNA handle can contain one or multiple barcodes, which can be arranged in various ways, such as being stacked successively or partially overlapping each other. The latter enables reduction of the overall length of a multiplex barcode, which increases multiplexing capabilities for a given gRNA handle length.

The multiplexing capability is proportional to the number of barcodes and is equal to the number of barcode combinations, such that nCr=r (n+r−1)!/r!(n−1)!, where n is the number of barcodes, r is the number of events where the barcodes are read. By example with two barcodes B1 and B2, C=1 and P=2 are obtained, for a total of 3 codes (B1B1, B1B2, B2B2). With 3 barcodes, 10 codes are obtained. 126 codes can be generated with as little as 5 barcodes, while 10 barcodes provide a total 92378 codes, enough to survey the exome.

Encoding methods provided herein are directed to the following. One code per locus can be assigned, which allows one to identify multiple targets in a single assay. One code per isoform for a given locus can be assigned, which allows variations to be identified. 2 codes for a given locus can be assigned, which provide colocalization of the signal identity for a given target, allowing for increased confidence of the target identity. This is advantageous in the case of a sample with high background, in which case the assay would be positive only if both signals are detected on the same loci. More than 2 codes can be assigned for a given locus, which would also allow for colocalization but provide signature that will improve identification and improve resolution. By example, two loci could be recognized by two sets of Cas9-gRNAs, the $1^{st}$ one encoded with barcodes B1B2 and B1B3, the $2^{nd}$ with barcode B1B3 and B1B4. The common B1 would provide an easily detectable signal across the loci. The signal locations can be focused on more specifically and the remaining barcodes B2B3 for loci 1, and B3B4 for loci 2 can be detected.

Table 2 provides a list of 5 barcodes, which were generated from a list a 12 nucleotide-long sequences that are not present more than once in the human genome:

TABLE 2

| Barcode | Sequence |
| --- | --- |
| B1 | CGTCGATTACCA (SEQ ID NO: 63) |
| B2 | CCATACTCGTCG (SEQ ID NO: 64) |
| B3 | TCGATAGTACGT (SEQ ID NO: 65) |
| B4 | CGTACTGAACGA (SEQ ID NO: 66) |
| B5 | CGAAGTACTACG (SEQ ID NO: 67) |
| B6 | TCGTTACGACCA (SEQ ID NO: 68) |
| B7 | CCAGACGAATCG (SEQ ID NO: 69) |
| B8 | TCGAATAGTCGT (SEQ ID NO: 70) |
| B9 | CGTAACTAACGA (SEQ ID NO: 71) |
| B10 | CGAACAATCGTA (SEQ ID NO: 72) |

A barcode size of 12 bases is sufficient to allow the design of a range of probes across a range of lengths and melting temperatures. By example, 10 to 12 mer probes allow for more stable interaction under certain ionic concentration (e.g. 5 mM $MgCl_2$), while still being removable using denaturant (e.g. 50% formamide). 8 to 9 mer probes allow to perform super-resolution imaging using the DNA-PAINT technique described in Jungmann R, Avendaño M S, Woehrstein J B, Dai M, Shih W M, Yin P. Multiplexed 3D cellular super-resolution imaging with DNA-PAINT and Exchange-PAINT. Nat Methods. 2014 March; 11(3):313-8).

The barcode-specific probes can be of many types and are adaptable to the assay. By example, the probe can be an oligonucleotide complement to the sequence. In another example, the probe can consist of circular ssDNA template, like a padlock probe, with one region of the probe hybridizing to the barcode and one or more regions serving as accessory hybridization for a secondary set of probes. The circular probe can then be amplified using rolling circle amplification, which would increase the signal intensity. In another example, the hybridizing probe is linear and contains sites for secondary probes which also contain sites for secondary or ternary probes and so on, allowing the self-assembly of a hyperbranched probe, which would increase the signal intensity. While most of the probes discussed here are fluorescently labeled, in another example, those probes are attached to a molecule which would allow for chromogenic detection, e.g. given a high density of gold nanoparticles the detection could be colorimetric and still visibly localized to specific region in the nucleus.

Figure 7:
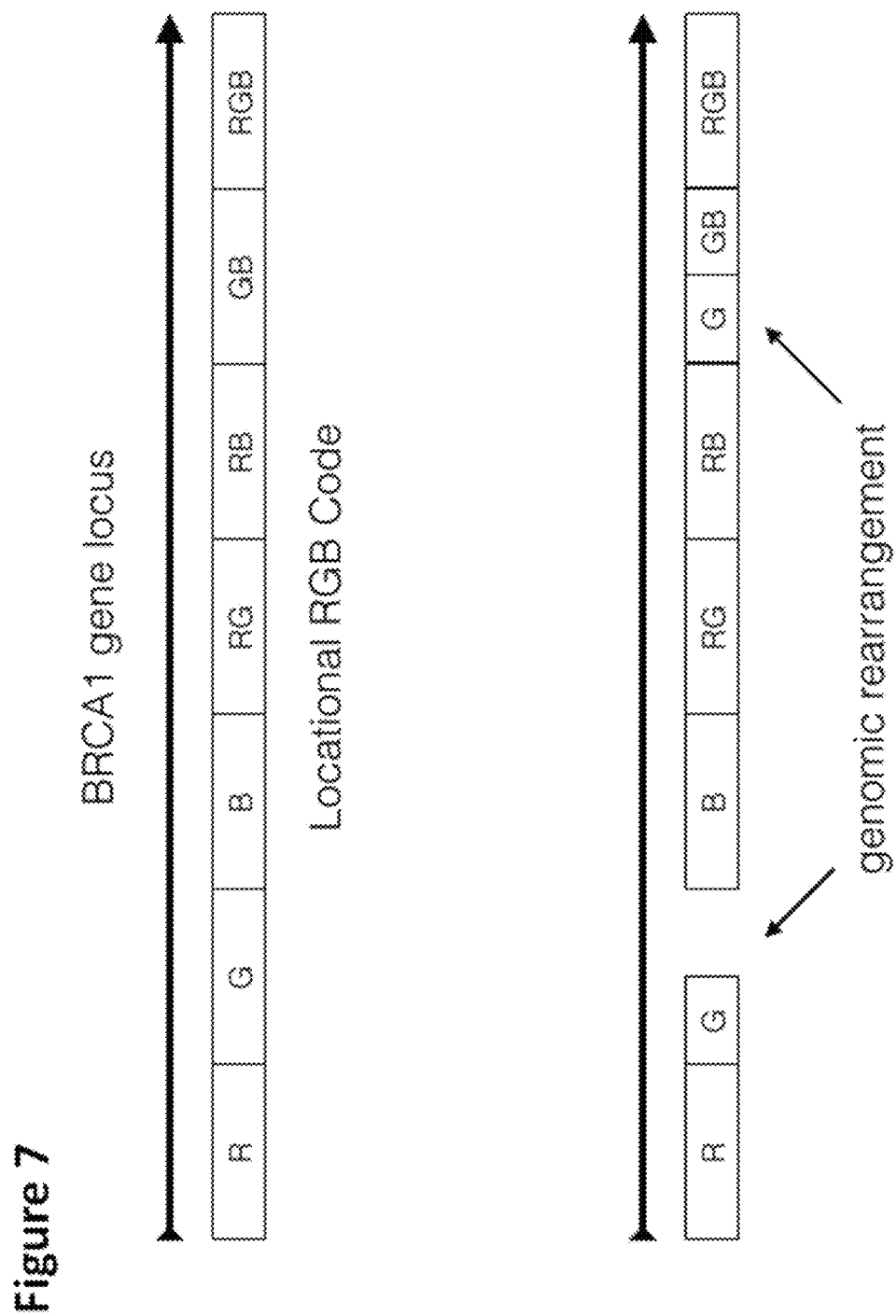
FIG. 7 presents a diagram for identifying genomic rearrangement using gRNA/Cas9 probing.

An example of a Locational RGB code is provided in FIG. 7, Guide RNA tails are barcoded according to color scheme listed as shown in Table 3 which lists gRNAs to fluorescently barcode BRCA1 rearrangement. R is Red, G is Green, B is blue. The barcodes are segregated in a way that forms an expected sequential color pattern. According to this scheme, each barcode is associated with a color, meaning that 3 barcode sequences need to be generated, which are then combined according to the color code. By example, if a gRNA code is R, then only barcode R needs to be added to the gRNA tail, while if a gRNA code is RGB, then all 3 barcodes need to be combined at the gRNA tail. The barcodes are detected via addition of their respective fluorescent probes, revealing the actual sequential color pattern. Any unexpected patterns will be identified as a genomic rearrangement.

TABLE 3

| | | Locational | Origami Code | | |
| --- | --- | --- | --- | --- | --- |
| Name | Position | Code | Spot1 | Spot2 | Spot3 |
| gRNA.BRCA1.1 | 5 | R | RG | RGB | RG |
| gRNA.BRCA1.2 | 177 | R | RG | RGB | RB |
| gRNA.BRCA1.3 | 317 | R | RG | RGB | BG |
| gRNA.BRCA1.4 | 460 | R | RG | RGB | R |
| gRNA.BRCA1.5 | 585 | R | RG | RGB | G |
| gRNA.BRCA1.6 | 610 | R | RG | RGB | B |
| gRNA.BRCA1.7 | 730 | R | RG | RB | RGB |
| gRNA.BRCA1.8 | 738 | R | RG | RB | RG |
| gRNA.BRCA1.9 | 792 | R | RG | RB | BG |
| gRNA.BRCA1.10 | 827 | R | RG | RB | R |
| gRNA.BRCA1.11 | 881 | R | RG | RB | G |
| gRNA.BRCA1.12 | 906 | R | RG | RB | B |
| gRNA.BRCA1.13 | 960 | R | RG | BG | RGB |
| gRNA.BRCA1.14 | 1,048 | R | RG | BG | RG |
| gRNA.BRCA1.15 | 1,220 | R | RG | BG | RB |
| gRNA.BRCA1.16 | 1,310 | R | RG | BG | R |
| gRNA.BRCA1.17 | 1,337 | R | RG | BG | G |
| gRNA.BRCA1.18 | 1,403 | R | RG | BG | B |
| gRNA.BRCA1.19 | 1,410 | R | RG | R | RGB |
| gRNA.BRCA1.20 | 1,446 | R | RG | R | RG |
| gRNA.BRCA1.21 | 1,459 | R | RG | R | RB |
| gRNA.BRCA1.22 | 1,509 | R | RG | R | BG |
| gRNA.BRCA1.23 | 1,561 | R | RG | R | G |
| gRNA.BRCA1.24 | 1,647 | R | RG | R | B |
| gRNA.BRCA1.25 | 1,667 | R | RG | G | RGB |
| gRNA.BRCA1.26 | 1,675 | R | RG | G | RG |
| gRNA.BRCA1.27 | 1,813 | R | RG | G | RB |
| gRNA.BRCA1.28 | 2,118 | R | RG | G | BG |
| gRNA.BRCA1.29 | 2,119 | R | RG | G | R |
| gRNA.BRCA1.30 | 2,120 | R | RG | B | RGB |
| gRNA.BRCA1.31 | 2,212 | R | RG | B | RG |
| gRNA.BRCA1.32 | 2,304 | R | RG | B | RB |
| gRNA.BRCA1.33 | 2,372 | R | RG | B | BG |
| gRNA.BRCA1.34 | 2,533 | R | RB | RGB | RG |
| gRNA.BRCA1.35 | 2,589 | R | RB | RGB | RB |
| gRNA.BRCA1.36 | 2,609 | R | RB | RGB | BG |

TABLE 3-continued

| Name | Position | Locational Code | Origami Code Spot1 | Spot2 | Spot3 |
|---|---|---|---|---|---|
| gRNA.BRCA1.37 | 2,662 | R | RB | RGB | R |
| gRNA.BRCA1.38 | 2,800 | R | RB | RGB | G |
| gRNA.BRCA1.39 | 2,844 | R | RB | RGB | B |
| gRNA.BRCA1.40 | 2,917 | R | RB | RG | RGB |
| gRNA.BRCA1.41 | 2,951 | R | RB | RG | RB |
| gRNA.BRCA1.42 | 3,012 | R | RB | RG | BG |
| gRNA.BRCA1.43 | 3,110 | R | RB | RG | R |
| gRNA.BRCA1.44 | 3,111 | R | RB | RG | G |
| gRNA.BRCA1.45 | 3,112 | R | RB | RG | B |
| gRNA.BRCA1.46 | 3,132 | R | RB | BG | RGB |
| gRNA.BRCA1.47 | 3,333 | R | RB | BG | RG |
| gRNA.BRCA1.48 | 3,362 | R | RB | BG | RB |
| gRNA.BRCA1.49 | 3,363 | R | RB | BG | R |
| gRNA.BRCA1.50 | 3,399 | R | RB | BG | G |
| gRNA.BRCA1.51 | 3,877 | R | RB | BG | B |
| gRNA.BRCA1.52 | 3,899 | R | RB | R | RGB |
| gRNA.BRCA1.53 | 4,168 | R | RB | R | RG |
| gRNA.BRCA1.54 | 4,174 | R | RB | R | RB |
| gRNA.BRCA1.55 | 4,200 | R | RB | R | BG |
| gRNA.BRCA1.56 | 4,401 | R | RB | R | G |
| gRNA.BRCA1.57 | 4,408 | R | RB | R | B |
| gRNA.BRCA1.58 | 4,422 | R | RB | G | RGB |
| gRNA.BRCA1.59 | 4,453 | R | RB | G | RG |
| gRNA.BRCA1.60 | 4,488 | R | RB | G | RB |
| gRNA.BRCA1.61 | 4,489 | R | RB | G | BG |
| gRNA.BRCA1.62 | 4,528 | R | RB | G | R |
| gRNA.BRCA1.63 | 4,691 | R | RB | G | B |
| gRNA.BRCA1.64 | 4,752 | R | RB | B | RGB |
| gRNA.BRCA1.65 | 4,777 | R | RB | B | RG |
| gRNA.BRCA1.66 | 4,831 | R | RB | B | RB |
| gRNA.BRCA1.67 | 4,919 | R | RB | B | BG |
| gRNA.BRCA1.68 | 4,955 | R | RB | B | R |
| gRNA.BRCA1.69 | 5,016 | R | RB | B | G |
| gRNA.BRCA1.70 | 5,123 | R | BG | RGB | RG |
| gRNA.BRCA1.71 | 5,146 | R | BG | RGB | RB |
| gRNA.BRCA1.72 | 5,191 | R | BG | RGB | BG |
| gRNA.BRCA1.73 | 5,282 | R | BG | RGB | R |
| gRNA.BRCA1.74 | 5,448 | R | BG | RGB | G |
| gRNA.BRCA1.75 | 5,473 | R | BG | RGB | B |
| gRNA.BRCA1.76 | 5,675 | R | BG | RG | RGB |
| gRNA.BRCA1.77 | 5,774 | R | BG | RG | RB |
| gRNA.BRCA1.78 | 5,808 | R | BG | RG | BG |
| gRNA.BRCA1.79 | 5,843 | R | BG | RG | R |
| gRNA.BRCA1.80 | 5,958 | R | BG | RG | G |
| gRNA.BRCA1.81 | 6,492 | R | BG | RG | B |
| gRNA.BRCA1.82 | 6,493 | R | BG | RB | RGB |
| gRNA.BRCA1.83 | 6,642 | R | BG | RB | RG |
| gRNA.BRCA1.84 | 6,903 | R | BG | RB | BG |
| gRNA.BRCA1.85 | 6,996 | R | BG | RB | R |
| gRNA.BRCA1.86 | 7,027 | R | BG | RB | G |
| gRNA.BRCA1.87 | 7,347 | R | BG | RB | B |
| gRNA.BRCA1.88 | 7,431 | R | BG | R | RGB |
| gRNA.BRCA1.89 | 7,444 | R | BG | R | RG |
| gRNA.BRCA1.90 | 7,453 | R | BG | R | RB |
| gRNA.BRCA1.91 | 7,474 | R | BG | R | BG |
| gRNA.BRCA1.92 | 7,479 | R | BG | R | G |
| gRNA.BRCA1.93 | 7,489 | R | BG | R | B |
| gRNA.BRCA1.94 | 7,490 | R | BG | G | RGB |
| gRNA.BRCA1.95 | 7,510 | R | BG | G | RG |
| gRNA.BRCA1.96 | 7,511 | R | BG | G | RB |
| gRNA.BRCA1.97 | 7,720 | R | BG | G | BG |
| gRNA.BRCA1.98 | 7,721 | R | BG | G | R |
| gRNA.BRCA1.99 | 7,997 | R | BG | B | RGB |
| gRNA.BRCA1.100 | 8,022 | R | BG | B | RG |
| gRNA.BRCA1.101 | 8,200 | R | BG | B | RB |
| gRNA.BRCA1.102 | 8,258 | R | BG | B | BG |
| gRNA.BRCA1.103 | 8,279 | R | BG | B | R |
| gRNA.BRCA1.104 | 8,380 | R | R | RGB | RG |
| gRNA.BRCA1.105 | 8,544 | R | R | RGB | RB |
| gRNA.BRCA1.106 | 8,556 | R | R | RGB | BG |
| gRNA.BRCA1.107 | 8,702 | G | R | RGB | R |
| gRNA.BRCA1.108 | 8,859 | G | R | RGB | G |
| gRNA.BRCA1.109 | 8,990 | G | R | RG | RGB |
| gRNA.BRCA1.110 | 9,079 | G | R | RG | RB |
| gRNA.BRCA1.111 | 9,080 | G | R | RG | BG |
| gRNA.BRCA1.112 | 9,315 | G | R | RG | R |
| gRNA.BRCA1.113 | 9,339 | G | R | RG | G |
| gRNA.BRCA1.114 | 9,407 | G | R | RG | B |
| gRNA.BRCA1.115 | 9,539 | G | R | RB | RGB |
| gRNA.BRCA1.116 | 9,814 | G | R | RB | RG |
| gRNA.BRCA1.117 | 9,835 | G | R | RB | BG |
| gRNA.BRCA1.118 | 10,035 | G | R | RB | R |
| gRNA.BRCA1.119 | 10,047 | G | R | RB | G |
| gRNA.BRCA1.120 | 10,107 | G | R | RB | B |
| gRNA.BRCA1.121 | 10,152 | G | R | BG | RGB |
| gRNA.BRCA1.122 | 10,201 | G | R | BG | RG |
| gRNA.BRCA1.123 | 10,303 | G | R | BG | RB |
| gRNA.BRCA1.124 | 10,478 | G | R | BG | R |
| gRNA.BRCA1.125 | 10,545 | G | R | BG | G |
| gRNA.BRCA1.126 | 10,548 | G | R | BG | B |
| gRNA.BRCA1.127 | 10,549 | G | R | G | RGB |
| gRNA.BRCA1.128 | 10,551 | G | R | G | RG |
| gRNA.BRCA1.129 | 10,760 | G | R | G | RB |
| gRNA.BRCA1.130 | 10,866 | G | R | G | BG |
| gRNA.BRCA1.131 | 10,874 | G | R | B | RG |
| gRNA.BRCA1.132 | 10,894 | G | R | B | RB |
| gRNA.BRCA1.133 | 10,990 | G | R | B | BG |
| gRNA.BRCA1.134 | 10,997 | G | G | RGB | RG |
| gRNA.BRCA1.135 | 11,082 | G | G | RGB | RB |
| gRNA.BRCA1.136 | 11,117 | G | G | RGB | BG |
| gRNA.BRCA1.137 | 11,137 | G | G | RGB | R |
| gRNA.BRCA1.138 | 11,151 | G | G | RGB | G |
| gRNA.BRCA1.139 | 11,172 | G | G | RGB | B |
| gRNA.BRCA1.140 | 11,602 | G | G | RG | RGB |
| gRNA.BRCA1.141 | 11,796 | G | G | RG | RB |
| gRNA.BRCA1.142 | 11,804 | G | G | RG | BG |
| gRNA.BRCA1.143 | 12,424 | G | G | RG | R |
| gRNA.BRCA1.144 | 12,737 | G | G | RG | G |
| gRNA.BRCA1.145 | 12,878 | G | G | RB | RGB |
| gRNA.BRCA1.146 | 12,922 | G | G | RB | RG |
| gRNA.BRCA1.147 | 12,977 | G | G | RB | BG |
| gRNA.BRCA1.148 | 12,998 | G | G | RB | R |
| gRNA.BRCA1.149 | 13,156 | G | G | RB | G |
| gRNA.BRCA1.150 | 13,178 | G | G | RB | B |
| gRNA.BRCA1.151 | 13,219 | G | G | BG | RGB |
| gRNA.BRCA1.152 | 13,483 | G | G | BG | RG |
| gRNA.BRCA1.153 | 13,578 | G | G | BG | RB |
| gRNA.BRCA1.154 | 13,637 | G | G | BG | R |
| gRNA.BRCA1.155 | 13,741 | G | G | BG | G |
| gRNA.BRCA1.156 | 13,831 | G | G | R | RGB |
| gRNA.BRCA1.157 | 13,997 | G | G | R | RG |
| gRNA.BRCA1.158 | 14,306 | G | G | R | RB |
| gRNA.BRCA1.159 | 14,476 | G | G | R | BG |
| gRNA.BRCA1.160 | 14,501 | G | G | B | RB |
| gRNA.BRCA1.161 | 14,522 | G | G | B | BG |
| gRNA.BRCA1.162 | 14,575 | G | B | RGB | RG |
| gRNA.BRCA1.163 | 14,587 | G | B | RGB | RB |
| gRNA.BRCA1.164 | 15,033 | G | B | RGB | BG |
| gRNA.BRCA1.165 | 15,219 | G | B | RG | RGB |
| gRNA.BRCA1.166 | 15,222 | G | B | RG | RB |
| gRNA.BRCA1.167 | 15,475 | G | B | RG | BG |
| gRNA.BRCA1.168 | 15,522 | G | B | RG | R |
| gRNA.BRCA1.169 | 15,579 | G | B | RB | RGB |
| gRNA.BRCA1.170 | 15,818 | G | B | RB | RG |
| gRNA.BRCA1.171 | 15,901 | G | B | RB | BG |
| gRNA.BRCA1.172 | 16,111 | G | B | RB | R |
| gRNA.BRCA1.173 | 16,136 | G | B | BG | RGB |
| gRNA.BRCA1.174 | 16,448 | G | B | BG | RG |
| gRNA.BRCA1.175 | 16,595 | G | B | BG | RB |
| gRNA.BRCA1.176 | 16,688 | G | B | BG | R |
| gRNA.BRCA1.177 | 16,747 | G | B | R | RGB |
| gRNA.BRCA1.178 | 16,748 | G | B | R | BG |
| gRNA.BRCA1.179 | 16,918 | G | B | G | RG |
| gRNA.BRCA1.180 | 16,974 | G | B | G | RB |
| gRNA.BRCA1.181 | 17,418 | G | B | G | BG |
| gRNA.BRCA1.182 | 17,422 | G | RGB | RG | RGB |
| gRNA.BRCA1.183 | 17,589 | G | RGB | RG | RB |
| gRNA.BRCA1.184 | 17,669 | G | RGB | RG | BG |
| gRNA.BRCA1.185 | 18,262 | G | RGB | RG | R |
| gRNA.BRCA1.186 | 18,269 | G | RGB | RG | G |
| gRNA.BRCA1.187 | 18,970 | G | RGB | RG | B |
| gRNA.BRCA1.188 | 18,971 | G | RGB | RB | RGB |

TABLE 3-continued

| Name | Position | Locational Code | Origami Code Spot1 | Spot2 | Spot3 |
|---|---|---|---|---|---|
| gRNA.BRCA1.189 | 19,005 | G | RGB | RB | RG |
| gRNA.BRCA1.190 | 19,026 | G | RGB | RB | BG |
| gRNA.BRCA1.191 | 19,289 | G | RGB | RB | R |
| gRNA.BRCA1.192 | 19,392 | G | RGB | RB | G |
| gRNA.BRCA1.193 | 19,445 | G | RGB | RB | B |
| gRNA.BRCA1.194 | 19,545 | G | RGB | BG | RGB |
| gRNA.BRCA1.195 | 19,570 | G | RGB | BG | RG |
| gRNA.BRCA1.196 | 19,818 | G | RGB | BG | RB |
| gRNA.BRCA1.197 | 19,819 | G | RGB | BG | R |
| gRNA.BRCA1.198 | 19,839 | G | RGB | BG | G |
| gRNA.BRCA1.199 | 20,595 | G | RGB | BG | B |
| gRNA.BRCA1.200 | 20,810 | G | RGB | R | RGB |
| gRNA.BRCA1.201 | 20,952 | G | RGB | R | RG |
| gRNA.BRCA1.202 | 20,988 | G | RGB | R | RB |
| gRNA.BRCA1.203 | 21,054 | G | RGB | R | BG |
| gRNA.BRCA1.204 | 21,075 | G | RGB | R | G |
| gRNA.BRCA1.205 | 21,352 | G | RGB | G | RGB |
| gRNA.BRCA1.206 | 21,440 | G | RGB | G | RG |
| gRNA.BRCA1.207 | 21,499 | G | RGB | G | RB |
| gRNA.BRCA1.208 | 21,506 | G | RGB | G | BG |
| gRNA.BRCA1.209 | 21,581 | G | RGB | G | R |
| gRNA.BRCA1.210 | 21,592 | G | RGB | B | RGB |
| gRNA.BRCA1.211 | 22,366 | G | RGB | B | RG |
| gRNA.BRCA1.212 | 22,373 | G | RGB | B | RB |
| gRNA.BRCA1.213 | 22,729 | B | RGB | B | BG |
| gRNA.BRCA1.214 | 22,760 | B | RGB | B | G |
| gRNA.BRCA1.215 | 22,824 | B | RB | RGB | RG |
| gRNA.BRCA1.216 | 22,849 | B | RB | RGB | RB |
| gRNA.BRCA1.217 | 23,339 | B | RB | RGB | BG |
| gRNA.BRCA1.218 | 23,739 | B | RB | RGB | R |
| gRNA.BRCA1.219 | 24,253 | B | RB | RGB | G |
| gRNA.BRCA1.220 | 24,443 | B | RB | RGB | B |
| gRNA.BRCA1.221 | 24,530 | B | RB | RG | RGB |
| gRNA.BRCA1.222 | 24,877 | B | RB | RG | RB |
| gRNA.BRCA1.223 | 24,878 | B | RB | RG | BG |
| gRNA.BRCA1.224 | 24,927 | B | RB | RG | R |
| gRNA.BRCA1.225 | 25,105 | B | RB | RG | G |
| gRNA.BRCA1.226 | 25,350 | B | RB | RG | B |
| gRNA.BRCA1.227 | 25,368 | B | RB | BG | RGB |
| gRNA.BRCA1.228 | 25,472 | B | RB | BG | RG |
| gRNA.BRCA1.229 | 25,525 | B | RB | BG | RB |
| gRNA.BRCA1.230 | 25,614 | B | RB | BG | R |
| gRNA.BRCA1.231 | 25,693 | B | RB | BG | G |
| gRNA.BRCA1.232 | 25,852 | B | RB | BG | B |
| gRNA.BRCA1.233 | 25,936 | B | RB | R | RGB |
| gRNA.BRCA1.234 | 25,972 | B | RB | R | RG |
| gRNA.BRCA1.235 | 26,984 | B | RB | R | RB |
| gRNA.BRCA1.236 | 27,130 | B | RB | R | BG |
| gRNA.BRCA1.237 | 27,155 | B | RB | R | G |
| gRNA.BRCA1.238 | 27,252 | B | RB | G | RGB |
| gRNA.BRCA1.239 | 27,256 | B | RB | G | RG |
| gRNA.BRCA1.240 | 27,431 | B | RB | G | RB |
| gRNA.BRCA1.241 | 27,447 | B | RB | G | BG |
| gRNA.BRCA1.242 | 27,452 | B | RB | G | R |
| gRNA.BRCA1.243 | 27,610 | B | RB | B | RGB |
| gRNA.BRCA1.244 | 27,631 | B | RB | B | RG |
| gRNA.BRCA1.245 | 27,682 | B | RB | B | RB |
| gRNA.BRCA1.246 | 27,722 | B | RB | B | BG |
| gRNA.BRCA1.247 | 28,262 | B | RB | B | R |
| gRNA.BRCA1.248 | 28,287 | B | RB | B | G |
| gRNA.BRCA1.249 | 28,400 | B | BG | RGB | RG |
| gRNA.BRCA1.250 | 28,425 | B | BG | RGB | RB |
| gRNA.BRCA1.251 | 28,464 | B | BG | RGB | BG |
| gRNA.BRCA1.252 | 28,581 | B | BG | RGB | R |
| gRNA.BRCA1.253 | 28,817 | B | BG | RGB | G |
| gRNA.BRCA1.254 | 28,958 | B | BG | RGB | B |
| gRNA.BRCA1.255 | 28,983 | B | BG | RG | RGB |
| gRNA.BRCA1.256 | 29,080 | B | BG | RG | RB |
| gRNA.BRCA1.257 | 29,202 | B | BG | RG | BG |
| gRNA.BRCA1.258 | 29,516 | B | BG | RG | R |
| gRNA.BRCA1.259 | 30,531 | B | BG | RG | G |
| gRNA.BRCA1.260 | 30,964 | B | BG | RG | B |
| gRNA.BRCA1.261 | 30,989 | B | BG | RB | RGB |
| gRNA.BRCA1.262 | 31,104 | B | BG | RB | RG |
| gRNA.BRCA1.263 | 31,374 | B | BG | RB | BG |
| gRNA.BRCA1.264 | 31,469 | B | BG | RB | R |
| gRNA.BRCA1.265 | 31,486 | B | BG | RB | G |
| gRNA.BRCA1.266 | 31,547 | B | BG | RB | B |
| gRNA.BRCA1.267 | 31,698 | B | BG | R | RGB |
| gRNA.BRCA1.268 | 32,906 | B | BG | R | RG |
| gRNA.BRCA1.269 | 32,942 | B | BG | R | RB |
| gRNA.BRCA1.270 | 32,973 | B | BG | R | BG |
| gRNA.BRCA1.271 | 33,121 | B | BG | R | G |
| gRNA.BRCA1.272 | 33,128 | B | BG | R | B |
| gRNA.BRCA1.273 | 33,335 | B | BG | G | RGB |
| gRNA.BRCA1.274 | 33,496 | B | BG | G | RG |
| gRNA.BRCA1.275 | 33,994 | B | BG | G | RB |
| gRNA.BRCA1.276 | 34,521 | B | BG | G | BG |
| gRNA.BRCA1.277 | 34,751 | B | BG | G | R |
| gRNA.BRCA1.278 | 34,892 | B | BG | B | RGB |
| gRNA.BRCA1.279 | 34,917 | B | BG | B | RG |
| gRNA.BRCA1.280 | 34,988 | B | BG | B | RB |
| gRNA.BRCA1.281 | 35,188 | B | BG | B | BG |
| gRNA.BRCA1.282 | 35,232 | B | BG | B | R |
| gRNA.BRCA1.283 | 35,330 | B | R | RGB | RG |
| gRNA.BRCA1.284 | 35,366 | B | R | RGB | RB |
| gRNA.BRCA1.285 | 35,445 | B | R | RGB | BG |
| gRNA.BRCA1.286 | 35,931 | B | R | RGB | R |
| gRNA.BRCA1.287 | 36,116 | B | R | RGB | G |
| gRNA.BRCA1.288 | 36,134 | B | R | RGB | B |
| gRNA.BRCA1.289 | 36,764 | B | R | RG | RGB |
| gRNA.BRCA1.290 | 36,884 | B | R | RG | RB |
| gRNA.BRCA1.291 | 36,905 | B | R | RG | BG |
| gRNA.BRCA1.292 | 37,050 | B | R | RG | R |
| gRNA.BRCA1.293 | 37,334 | B | R | RG | G |
| gRNA.BRCA1.294 | 37,867 | B | R | RB | RGB |
| gRNA.BRCA1.295 | 38,007 | B | R | RB | RG |
| gRNA.BRCA1.296 | 38,032 | B | R | RB | BG |
| gRNA.BRCA1.297 | 38,275 | B | R | RB | R |
| gRNA.BRCA1.298 | 38,325 | B | R | RB | G |
| gRNA.BRCA1.299 | 38,470 | B | R | RB | B |
| gRNA.BRCA1.300 | 38,471 | B | R | BG | RGB |
| gRNA.BRCA1.301 | 38,472 | B | R | BG | RG |
| gRNA.BRCA1.302 | 38,825 | B | R | BG | RB |
| gRNA.BRCA1.303 | 38,842 | B | R | BG | R |
| gRNA.BRCA1.304 | 39,099 | B | R | BG | G |
| gRNA.BRCA1.305 | 39,109 | B | R | BG | B |
| gRNA.BRCA1.306 | 39,114 | B | R | G | RGB |
| gRNA.BRCA1.307 | 39,115 | B | R | G | RG |
| gRNA.BRCA1.308 | 39,786 | B | R | G | RB |
| gRNA.BRCA1.309 | 39,801 | B | R | G | BG |
| gRNA.BRCA1.310 | 39,865 | B | R | B | RGB |
| gRNA.BRCA1.311 | 40,010 | B | R | B | RG |
| gRNA.BRCA1.312 | 40,054 | B | R | B | RB |
| gRNA.BRCA1.313 | 40,221 | B | G | RGB | RG |
| gRNA.BRCA1.314 | 40,663 | B | G | RGB | RB |
| gRNA.BRCA1.315 | 40,927 | B | G | RGB | BG |
| gRNA.BRCA1.316 | 41,058 | B | G | RGB | R |
| gRNA.BRCA1.317 | 41,059 | B | G | RGB | G |
| gRNA.BRCA1.318 | 41,341 | B | G | RG | RGB |
| gRNA.BRCA1.319 | 41,688 | B | G | RG | RB |
| gRNA.BRCA1.320 | 42,346 | RG | G | RG | BG |
| gRNA.BRCA1.321 | 42,400 | RG | G | RG | R |
| gRNA.BRCA1.322 | 42,753 | RG | G | RG | G |
| gRNA.BRCA1.323 | 42,862 | RG | G | RG | B |
| gRNA.BRCA1.324 | 42,870 | RG | G | RB | RGB |
| gRNA.BRCA1.325 | 42,891 | RG | G | RB | RG |
| gRNA.BRCA1.326 | 42,912 | RG | G | RB | BG |
| gRNA.BRCA1.327 | 42,943 | RG | G | RB | R |
| gRNA.BRCA1.328 | 42,952 | RG | G | RB | G |
| gRNA.BRCA1.329 | 42,964 | RG | G | RB | B |
| gRNA.BRCA1.330 | 43,471 | RG | G | BG | RGB |
| gRNA.BRCA1.331 | 43,514 | RG | G | BG | RG |
| gRNA.BRCA1.332 | 43,594 | RG | G | BG | RB |
| gRNA.BRCA1.333 | 43,783 | RG | G | BG | R |
| gRNA.BRCA1.334 | 44,610 | RG | G | BG | G |
| gRNA.BRCA1.335 | 44,956 | RG | G | R | RGB |
| gRNA.BRCA1.336 | 45,085 | RG | G | R | RG |
| gRNA.BRCA1.337 | 45,408 | RG | G | R | RB |
| gRNA.BRCA1.338 | 45,642 | RG | G | R | BG |
| gRNA.BRCA1.339 | 45,834 | RG | G | B | RGB |
| gRNA.BRCA1.340 | 45,939 | RG | G | B | BG |

TABLE 3-continued

| Name | Position | Locational Code | Origami Code Spot1 | Spot2 | Spot3 |
|---|---|---|---|---|---|
| gRNA.BRCA1.341 | 46,018 | RG | B | RGB | RG |
| gRNA.BRCA1.342 | 46,057 | RG | B | RGB | RB |
| gRNA.BRCA1.343 | 46,159 | RG | B | RGB | BG |
| gRNA.BRCA1.344 | 46,184 | RG | B | RGB | G |
| gRNA.BRCA1.345 | 46,866 | RG | B | RG | RGB |
| gRNA.BRCA1.346 | 47,006 | RG | B | RG | RB |
| gRNA.BRCA1.347 | 47,161 | RG | B | RG | BG |
| gRNA.BRCA1.348 | 47,295 | RG | B | RG | G |
| gRNA.BRCA1.349 | 47,316 | RG | B | RB | RGB |
| gRNA.BRCA1.350 | 47,624 | RG | B | RB | RG |
| gRNA.BRCA1.351 | 48,296 | RG | B | RB | BG |
| gRNA.BRCA1.352 | 48,417 | RG | B | RB | R |
| gRNA.BRCA1.353 | 48,597 | RG | B | BG | RGB |
| gRNA.BRCA1.354 | 48,709 | RG | B | BG | RG |
| gRNA.BRCA1.355 | 48,741 | RG | B | BG | RB |
| gRNA.BRCA1.356 | 49,338 | RG | B | BG | G |
| gRNA.BRCA1.357 | 49,509 | RG | B | R | RG |
| gRNA.BRCA1.358 | 49,850 | RG | B | R | BG |
| gRNA.BRCA1.359 | 50,036 | RG | B | G | RG |
| gRNA.BRCA1.360 | 50,332 | RG | B | G | RB |
| gRNA.BRCA1.361 | 50,553 | RG | RGB | RG | RGB |
| gRNA.BRCA1.362 | 50,611 | RG | RGB | RG | RB |
| gRNA.BRCA1.363 | 50,725 | RG | RGB | RG | BG |
| gRNA.BRCA1.364 | 51,015 | RG | RGB | RG | R |
| gRNA.BRCA1.365 | 51,082 | RG | RGB | RG | G |
| gRNA.BRCA1.366 | 51,519 | RG | RGB | RG | B |
| gRNA.BRCA1.367 | 51,797 | RG | RGB | RB | RGB |
| gRNA.BRCA1.368 | 51,939 | RG | RGB | RB | RG |
| gRNA.BRCA1.369 | 51,964 | RG | RGB | RB | BG |
| gRNA.BRCA1.370 | 52,106 | RG | RGB | RB | R |
| gRNA.BRCA1.371 | 52,142 | RG | RGB | RB | G |
| gRNA.BRCA1.372 | 52,240 | RG | RGB | RB | B |
| gRNA.BRCA1.373 | 52,265 | RG | RGB | BG | RGB |
| gRNA.BRCA1.374 | 52,396 | RG | RGB | BG | RG |
| gRNA.BRCA1.375 | 52,687 | RG | RGB | BG | RB |
| gRNA.BRCA1.376 | 52,906 | RG | RGB | BG | R |
| gRNA.BRCA1.377 | 53,519 | RG | RGB | BG | G |
| gRNA.BRCA1.378 | 54,362 | RG | RGB | BG | B |
| gRNA.BRCA1.379 | 54,794 | RG | RGB | R | RGB |
| gRNA.BRCA1.380 | 54,956 | RG | RGB | R | RG |
| gRNA.BRCA1.381 | 54,957 | RG | RGB | R | RB |
| gRNA.BRCA1.382 | 54,976 | RG | RGB | R | BG |
| gRNA.BRCA1.383 | 55,494 | RG | RGB | R | G |
| gRNA.BRCA1.384 | 55,623 | RG | RGB | G | RGB |
| gRNA.BRCA1.385 | 55,661 | RG | RGB | G | RG |
| gRNA.BRCA1.386 | 55,668 | RG | RGB | G | RB |
| gRNA.BRCA1.387 | 55,678 | RG | RGB | G | BG |
| gRNA.BRCA1.388 | 56,191 | RG | RGB | G | R |
| gRNA.BRCA1.389 | 56,192 | RG | RGB | B | RGB |
| gRNA.BRCA1.390 | 56,200 | RG | RGB | B | RG |
| gRNA.BRCA1.391 | 57,155 | RG | RGB | B | RB |
| gRNA.BRCA1.392 | 57,180 | RG | RGB | B | BG |
| gRNA.BRCA1.393 | 57,839 | RG | RGB | B | R |
| gRNA.BRCA1.394 | 57,864 | RG | RGB | B | G |
| gRNA.BRCA1.395 | 58,010 | RG | RG | RGB | RG |
| gRNA.BRCA1.396 | 58,204 | RG | RG | RGB | RB |
| gRNA.BRCA1.397 | 58,282 | RG | RG | RGB | BG |
| gRNA.BRCA1.398 | 58,325 | RG | RG | RGB | R |
| gRNA.BRCA1.399 | 58,449 | RG | RG | RGB | G |
| gRNA.BRCA1.400 | 58,474 | RG | RG | RGB | B |
| gRNA.BRCA1.401 | 58,672 | RG | RG | RB | RGB |
| gRNA.BRCA1.402 | 58,835 | RG | RG | RB | RG |
| gRNA.BRCA1.403 | 59,401 | RG | RG | RB | BG |
| gRNA.BRCA1.404 | 59,800 | RG | RG | RB | R |
| gRNA.BRCA1.405 | 59,983 | RG | RG | RB | G |
| gRNA.BRCA1.406 | 60,099 | RG | RG | RB | B |
| gRNA.BRCA1.407 | 60,227 | RG | RG | BG | RGB |
| gRNA.BRCA1.408 | 60,231 | RG | RG | BG | RG |
| gRNA.BRCA1.409 | 60,248 | RG | RG | BG | RB |
| gRNA.BRCA1.410 | 60,252 | RG | RG | BG | R |
| gRNA.BRCA1.411 | 61,036 | RG | RG | BG | G |
| gRNA.BRCA1.412 | 61,740 | RG | RG | BG | B |
| gRNA.BRCA1.413 | 61,926 | RG | RG | R | RGB |
| gRNA.BRCA1.414 | 62,214 | RG | RG | R | RG |
| gRNA.BRCA1.415 | 62,304 | RG | RG | R | RB |
| gRNA.BRCA1.416 | 62,672 | RG | RG | R | BG |
| gRNA.BRCA1.417 | 62,820 | RG | RG | R | G |
| gRNA.BRCA1.418 | 63,273 | RG | RG | R | B |
| gRNA.BRCA1.419 | 63,414 | RG | RG | G | RGB |
| gRNA.BRCA1.420 | 63,439 | RG | RG | G | RG |
| gRNA.BRCA1.421 | 63,505 | RG | RG | G | RB |
| gRNA.BRCA1.422 | 64,068 | RG | RG | G | BG |
| gRNA.BRCA1.423 | 64,187 | RG | RG | G | R |
| gRNA.BRCA1.424 | 64,302 | RG | RG | G | B |
| gRNA.BRCA1.425 | 64,404 | RG | RG | B | RGB |
| gRNA.BRCA1.426 | 64,411 | RG | RG | B | RG |
| gRNA.BRCA1.427 | 64,455 | RB | RG | B | RB |
| gRNA.BRCA1.428 | 64,479 | RB | RG | B | BG |
| gRNA.BRCA1.429 | 64,500 | RB | RG | B | R |
| gRNA.BRCA1.430 | 65,444 | RB | RG | B | G |
| gRNA.BRCA1.431 | 65,692 | RB | BG | RGB | RG |
| gRNA.BRCA1.432 | 65,759 | RB | BG | RGB | RB |
| gRNA.BRCA1.433 | 66,292 | RB | BG | RGB | BG |
| gRNA.BRCA1.434 | 66,442 | RB | BG | RGB | R |
| gRNA.BRCA1.435 | 66,751 | RB | BG | RGB | G |
| gRNA.BRCA1.436 | 66,897 | RB | BG | RGB | B |
| gRNA.BRCA1.437 | 66,922 | RB | BG | RG | RGB |
| gRNA.BRCA1.438 | 67,204 | RB | BG | RG | RB |
| gRNA.BRCA1.439 | 67,370 | RB | BG | RG | BG |
| gRNA.BRCA1.440 | 67,444 | RB | BG | RG | R |
| gRNA.BRCA1.441 | 67,977 | RB | BG | RG | G |
| gRNA.BRCA1.442 | 68,830 | RB | BG | RG | B |
| gRNA.BRCA1.443 | 68,873 | RB | BG | RB | RGB |
| gRNA.BRCA1.444 | 68,912 | RB | BG | RB | RG |
| gRNA.BRCA1.445 | 69,130 | RB | BG | RB | BG |
| gRNA.BRCA1.446 | 69,271 | RB | BG | RB | R |
| gRNA.BRCA1.447 | 69,436 | RB | BG | RB | G |
| gRNA.BRCA1.448 | 69,925 | RB | BG | RB | B |
| gRNA.BRCA1.449 | 70,004 | RB | BG | R | RGB |
| gRNA.BRCA1.450 | 70,147 | RB | BG | R | RG |
| gRNA.BRCA1.451 | 70,290 | RB | BG | R | RB |
| gRNA.BRCA1.452 | 70,432 | RB | BG | R | BG |
| gRNA.BRCA1.453 | 70,467 | RB | BG | R | G |
| gRNA.BRCA1.454 | 70,754 | RB | BG | R | B |
| gRNA.BRCA1.455 | 70,800 | RB | BG | G | RGB |
| gRNA.BRCA1.456 | 70,924 | RB | BG | G | RG |
| gRNA.BRCA1.457 | 71,133 | RB | BG | G | RB |
| gRNA.BRCA1.458 | 71,158 | RB | BG | G | BG |
| gRNA.BRCA1.459 | 71,397 | RB | BG | G | R |
| gRNA.BRCA1.460 | 71,398 | RB | BG | B | RGB |
| gRNA.BRCA1.461 | 71,773 | RB | BG | B | RG |
| gRNA.BRCA1.462 | 71,798 | RB | BG | B | RB |
| gRNA.BRCA1.463 | 71,915 | RB | BG | B | BG |
| gRNA.BRCA1.464 | 72,051 | RB | BG | B | R |
| gRNA.BRCA1.465 | 73,315 | RB | BG | B | G |
| gRNA.BRCA1.466 | 73,457 | RB | R | RGB | RG |
| gRNA.BRCA1.467 | 73,797 | RB | R | RGB | RB |
| gRNA.BRCA1.468 | 73,909 | RB | R | RGB | BG |
| gRNA.BRCA1.469 | 73,951 | RB | R | RGB | R |
| gRNA.BRCA1.470 | 74,973 | RB | R | RGB | G |
| gRNA.BRCA1.471 | 74,998 | RB | R | RGB | B |
| gRNA.BRCA1.472 | 75,052 | RB | R | RG | RGB |
| gRNA.BRCA1.473 | 75,139 | RB | R | RG | RB |
| gRNA.BRCA1.474 | 75,148 | RB | R | RG | BG |
| gRNA.BRCA1.475 | 75,175 | RB | R | RG | R |
| gRNA.BRCA1.476 | 75,837 | RB | R | RG | G |
| gRNA.BRCA1.477 | 75,851 | RB | R | RB | RGB |
| gRNA.BRCA1.478 | 75,926 | RB | R | RB | RG |
| gRNA.BRCA1.479 | 75,927 | RB | R | RB | BG |
| gRNA.BRCA1.480 | 76,170 | RB | R | RB | R |
| gRNA.BRCA1.481 | 76,487 | RB | R | RB | G |
| gRNA.BRCA1.482 | 77,242 | RB | R | RB | B |
| gRNA.BRCA1.483 | 77,401 | RB | R | BG | RGB |
| gRNA.BRCA1.484 | 77,803 | RB | R | BG | RG |
| gRNA.BRCA1.485 | 77,970 | RB | R | BG | RB |
| gRNA.BRCA1.486 | 78,230 | RB | R | BG | R |
| gRNA.BRCA1.487 | 78,231 | RB | R | BG | G |
| gRNA.BRCA1.488 | 78,277 | RB | R | G | RGB |
| gRNA.BRCA1.489 | 78,625 | RB | R | G | RG |
| gRNA.BRCA1.490 | 78,933 | RB | R | G | RB |
| gRNA.BRCA1.491 | 78,958 | RB | R | G | BG |
| gRNA.BRCA1.492 | 79,186 | RB | R | B | RG |

TABLE 3-continued

| Name | Position | Locational Code | Origami Code Spot1 | Spot2 | Spot3 |
|---|---|---|---|---|---|
| gRNA.BRCA1.493 | 79,211 | RB | R | B | RB |
| gRNA.BRCA1.494 | 79,475 | RB | G | RGB | RG |
| gRNA.BRCA1.495 | 79,600 | RB | G | RGB | RB |
| gRNA.BRCA1.496 | 79,654 | RB | G | RGB | BG |
| gRNA.BRCA1.497 | 79,679 | RB | G | RGB | R |
| gRNA.BRCA1.498 | 79,998 | RB | G | RGB | G |
| gRNA.BRCA1.499 | 80,198 | RB | G | RGB | B |
| gRNA.BRCA1.500 | 80,737 | RB | G | RG | RGB |
| gRNA.BRCA1.501 | 80,877 | RB | G | RG | RB |
| gRNA.BRCA1.502 | 80,902 | RB | G | RG | BG |
| gRNA.BRCA1.503 | 80,986 | RB | G | RG | R |
| gRNA.BRCA1.504 | 81,300 | RB | G | RG | G |
| gRNA.BRCA1.505 | 81,339 | RB | G | RB | RGB |
| gRNA.BRCA1.506 | 81,479 | RB | G | RB | RG |
| gRNA.BRCA1.507 | 81,765 | RB | G | RB | BG |
| gRNA.BRCA1.508 | 81,907 | RB | G | RB | R |
| gRNA.BRCA1.509 | 81,932 | RB | G | RB | G |
| gRNA.BRCA1.510 | 82,467 | RB | G | RB | B |
| gRNA.BRCA1.511 | 82,513 | RB | G | BG | RGB |
| gRNA.BRCA1.512 | 82,521 | RB | G | BG | RG |
| gRNA.BRCA1.513 | 82,522 | RB | G | BG | RB |
| gRNA.BRCA1.514 | 82,537 | RB | G | BG | R |
| gRNA.BRCA1.515 | 82,729 | RB | G | BG | G |
| gRNA.BRCA1.516 | 82,919 | RB | G | R | RGB |
| gRNA.BRCA1.517 | 83,157 | RB | G | R | RG |
| gRNA.BRCA1.518 | 83,334 | RB | G | R | RB |
| gRNA.BRCA1.519 | 83,681 | RB | G | R | BG |
| gRNA.BRCA1.520 | 84,189 | RB | G | B | RGB |
| gRNA.BRCA1.521 | 84,452 | RB | G | B | BG |
| gRNA.BRCA1.522 | 84,618 | RB | B | RGB | RG |
| gRNA.BRCA1.523 | 85,185 | RB | B | RGB | RB |
| gRNA.BRCA1.524 | 85,276 | RB | B | RGB | BG |
| gRNA.BRCA1.525 | 85,394 | RB | B | RG | RGB |
| gRNA.BRCA1.526 | 85,527 | RB | B | RG | RB |
| gRNA.BRCA1.527 | 85,571 | RB | B | RG | BG |
| gRNA.BRCA1.528 | 85,596 | RB | B | RG | R |
| gRNA.BRCA1.529 | 85,683 | RB | B | RG | G |
| gRNA.BRCA1.530 | 85,936 | RB | B | RB | RGB |
| gRNA.BRCA1.531 | 85,955 | RB | B | RB | RG |
| gRNA.BRCA1.532 | 86,055 | RB | B | RB | BG |
| gRNA.BRCA1.533 | 86,194 | GB | B | BG | RGB |
| gRNA.BRCA1.534 | 86,303 | GB | B | BG | RG |
| gRNA.BRCA1.535 | 86,310 | GB | B | BG | RB |
| gRNA.BRCA1.536 | 86,697 | GB | B | BG | R |
| gRNA.BRCA1.537 | 86,810 | GB | B | R | RGB |
| gRNA.BRCA1.538 | 86,840 | GB | B | R | RG |
| gRNA.BRCA1.539 | 86,960 | GB | B | R | BG |
| gRNA.BRCA1.540 | 87,126 | GB | B | G | RG |
| gRNA.BRCA1.541 | 87,199 | GB | B | G | BG |
| gRNA.BRCA1.542 | 87,247 | GB | RGB | RG | RGB |
| gRNA.BRCA1.543 | 87,355 | GB | RGB | RG | RB |
| gRNA.BRCA1.544 | 88,350 | GB | RGB | RG | BG |
| gRNA.BRCA1.545 | 88,419 | GB | RGB | RG | R |
| gRNA.BRCA1.546 | 88,446 | GB | RGB | RG | G |
| gRNA.BRCA1.547 | 88,455 | GB | RGB | RG | B |
| gRNA.BRCA1.548 | 88,543 | GB | RGB | RB | RGB |
| gRNA.BRCA1.549 | 88,597 | GB | RGB | RB | RG |
| gRNA.BRCA1.550 | 88,604 | GB | RGB | RB | BG |
| gRNA.BRCA1.551 | 88,622 | GB | RGB | RB | R |
| gRNA.BRCA1.552 | 88,720 | GB | RGB | RB | G |
| gRNA.BRCA1.553 | 88,902 | GB | RGB | RB | B |
| gRNA.BRCA1.554 | 88,909 | GB | RGB | BG | RGB |
| gRNA.BRCA1.555 | 88,927 | GB | RGB | BG | RG |
| gRNA.BRCA1.556 | 88,955 | GB | RGB | BG | RB |
| gRNA.BRCA1.557 | 88,960 | GB | RGB | BG | R |
| gRNA.BRCA1.558 | 88,998 | GB | RGB | BG | G |
| gRNA.BRCA1.559 | 89,029 | GB | RGB | BG | B |
| gRNA.BRCA1.560 | 89,153 | GB | RGB | R | RGB |
| gRNA.BRCA1.561 | 89,207 | GB | RGB | R | RG |
| gRNA.BRCA1.562 | 89,351 | GB | RGB | R | RB |
| gRNA.BRCA1.563 | 89,515 | GB | RGB | R | BG |
| gRNA.BRCA1.564 | 90,439 | GB | RGB | R | G |
| gRNA.BRCA1.565 | 90,440 | GB | RGB | G | RGB |
| gRNA.BRCA1.566 | 90,441 | GB | RGB | G | RG |
| gRNA.BRCA1.567 | 90,462 | GB | RGB | G | RB |
| gRNA.BRCA1.568 | 90,700 | GB | RGB | G | BG |
| gRNA.BRCA1.569 | 90,736 | GB | RGB | G | R |
| gRNA.BRCA1.570 | 90,914 | GB | RGB | G | B |
| gRNA.BRCA1.571 | 91,209 | GB | RGB | B | RGB |
| gRNA.BRCA1.572 | 91,284 | GB | RGB | B | RG |
| gRNA.BRCA1.573 | 91,323 | GB | RGB | B | RB |
| gRNA.BRCA1.574 | 91,424 | GB | RGB | B | BG |
| gRNA.BRCA1.575 | 91,460 | GB | RGB | B | R |
| gRNA.BRCA1.576 | 91,603 | GB | RG | RGB | RG |
| gRNA.BRCA1.577 | 91,678 | GB | RG | RGB | RB |
| gRNA.BRCA1.578 | 91,710 | GB | RG | RGB | BG |
| gRNA.BRCA1.579 | 92,123 | GB | RG | RGB | R |
| gRNA.BRCA1.580 | 92,226 | GB | RG | RGB | G |
| gRNA.BRCA1.581 | 92,269 | GB | RG | RGB | B |
| gRNA.BRCA1.582 | 92,347 | GB | RG | RB | RGB |
| gRNA.BRCA1.583 | 92,363 | GB | RG | RB | RG |
| gRNA.BRCA1.584 | 92,368 | GB | RG | RB | BG |
| gRNA.BRCA1.585 | 92,384 | GB | RG | RB | R |
| gRNA.BRCA1.586 | 92,520 | GB | RG | RB | G |
| gRNA.BRCA1.587 | 92,536 | GB | RG | RB | B |
| gRNA.BRCA1.588 | 92,540 | GB | RG | BG | RGB |
| gRNA.BRCA1.589 | 92,541 | GB | RG | BG | RG |
| gRNA.BRCA1.590 | 92,557 | GB | RG | BG | RB |
| gRNA.BRCA1.591 | 92,604 | GB | RG | BG | R |
| gRNA.BRCA1.592 | 92,690 | GB | RG | BG | G |
| gRNA.BRCA1.593 | 92,820 | GB | RG | BG | B |
| gRNA.BRCA1.594 | 92,899 | GB | RG | R | RGB |
| gRNA.BRCA1.595 | 92,914 | GB | RG | R | RG |
| gRNA.BRCA1.596 | 92,935 | GB | RG | R | RB |
| gRNA.BRCA1.597 | 92,936 | GB | RG | R | BG |
| gRNA.BRCA1.598 | 92,957 | GB | RG | R | G |
| gRNA.BRCA1.599 | 92,978 | GB | RG | R | B |
| gRNA.BRCA1.600 | 92,979 | GB | RG | G | RGB |
| gRNA.BRCA1.601 | 93,001 | GB | RG | G | RG |
| gRNA.BRCA1.602 | 93,022 | GB | RG | G | RB |
| gRNA.BRCA1.603 | 93,029 | GB | RG | G | BG |
| gRNA.BRCA1.604 | 93,045 | GB | RG | G | R |
| gRNA.BRCA1.605 | 93,067 | GB | RG | B | RGB |
| gRNA.BRCA1.606 | 93,088 | GB | RG | B | RG |
| gRNA.BRCA1.607 | 93,107 | GB | RG | B | RB |
| gRNA.BRCA1.608 | 93,108 | GB | RG | B | BG |
| gRNA.BRCA1.609 | 93,123 | GB | RG | B | G |
| gRNA.BRCA1.610 | 93,134 | GB | RB | RGB | RG |
| gRNA.BRCA1.611 | 93,140 | GB | RB | RGB | RB |
| gRNA.BRCA1.612 | 93,141 | GB | RB | RGB | BG |
| gRNA.BRCA1.613 | 93,173 | GB | RB | RGB | R |
| gRNA.BRCA1.614 | 93,364 | GB | RB | RGB | G |
| gRNA.BRCA1.615 | 93,611 | GB | RB | RGB | B |
| gRNA.BRCA1.616 | 93,612 | GB | RB | RG | RGB |
| gRNA.BRCA1.617 | 93,774 | GB | RB | RG | RB |
| gRNA.BRCA1.618 | 93,999 | GB | RB | RG | BG |
| gRNA.BRCA1.619 | 94,032 | GB | RB | RG | R |
| gRNA.BRCA1.620 | 94,130 | GB | RB | RG | G |
| gRNA.BRCA1.621 | 94,341 | GB | RB | RG | B |
| gRNA.BRCA1.622 | 94,367 | GB | RB | BG | RGB |
| gRNA.BRCA1.623 | 94,388 | GB | RB | BG | RG |
| gRNA.BRCA1.624 | 94,406 | GB | RB | BG | RB |
| gRNA.BRCA1.625 | 94,429 | GB | RB | BG | R |
| gRNA.BRCA1.626 | 94,511 | GB | RB | BG | G |
| gRNA.BRCA1.627 | 94,577 | GB | RB | BG | B |
| gRNA.BRCA1.628 | 94,608 | GB | RB | R | RGB |
| gRNA.BRCA1.629 | 94,644 | GB | RB | R | RG |
| gRNA.BRCA1.630 | 94,645 | GB | RB | R | RB |
| gRNA.BRCA1.631 | 94,666 | GB | RB | R | BG |
| gRNA.BRCA1.632 | 94,674 | GB | RB | R | G |
| gRNA.BRCA1.633 | 94,712 | GB | RB | R | B |
| gRNA.BRCA1.634 | 94,713 | GB | RB | G | RGB |
| gRNA.BRCA1.635 | 94,725 | GB | RB | G | RG |
| gRNA.BRCA1.636 | 94,803 | GB | RB | G | RB |
| gRNA.BRCA1.637 | 94,804 | GB | RB | G | BG |
| gRNA.BRCA1.638 | 94,816 | GB | RB | G | R |
| gRNA.BRCA1.639 | 94,850 | RGB | RB | G | B |
| gRNA.BRCA1.640 | 94,904 | RGB | RB | B | RGB |
| gRNA.BRCA1.641 | 94,905 | RGB | RB | B | RG |
| gRNA.BRCA1.642 | 94,922 | RGB | RB | B | RB |
| gRNA.BRCA1.643 | 94,923 | RGB | RB | B | BG |
| gRNA.BRCA1.644 | 94,965 | RGB | RB | B | R |

TABLE 3-continued

| Name | Position | Locational Code | Origami Code Spot1 | Spot2 | Spot3 |
|---|---|---|---|---|---|
| gRNA.BRCA1.645 | 94,966 | RGB | RB | B | G |
| gRNA.BRCA1.646 | 94,982 | RGB | R | RGB | RG |
| gRNA.BRCA1.647 | 94,991 | RGB | R | RGB | RB |
| gRNA.BRCA1.648 | 95,012 | RGB | R | RGB | BG |
| gRNA.BRCA1.649 | 95,018 | RGB | R | RGB | R |
| gRNA.BRCA1.650 | 95,033 | RGB | R | RGB | G |
| gRNA.BRCA1.651 | 95,038 | RGB | R | RG | RGB |
| gRNA.BRCA1.652 | 95,039 | RGB | R | RG | RB |
| gRNA.BRCA1.653 | 95,636 | RGB | R | RG | BG |
| gRNA.BRCA1.654 | 95,714 | RGB | R | RG | R |
| gRNA.BRCA1.655 | 95,802 | RGB | R | RG | G |
| gRNA.BRCA1.656 | 95,856 | RGB | R | RB | RGB |
| gRNA.BRCA1.657 | 95,881 | RGB | R | RB | RG |
| gRNA.BRCA1.658 | 96,183 | RGB | R | RB | BG |
| gRNA.BRCA1.659 | 96,409 | RGB | R | RB | R |
| gRNA.BRCA1.660 | 96,593 | RGB | R | RB | G |
| gRNA.BRCA1.661 | 96,594 | RGB | R | RB | B |
| gRNA.BRCA1.662 | 96,879 | RGB | R | BG | RGB |
| gRNA.BRCA1.663 | 97,267 | RGB | R | BG | RG |
| gRNA.BRCA1.664 | 97,461 | RGB | R | BG | RB |
| gRNA.BRCA1.665 | 97,550 | RGB | R | BG | R |
| gRNA.BRCA1.666 | 97,586 | RGB | R | BG | G |
| gRNA.BRCA1.667 | 98,126 | RGB | R | G | RGB |
| gRNA.BRCA1.668 | 98,248 | RGB | R | G | RG |
| gRNA.BRCA1.669 | 98,443 | RGB | R | G | RB |
| gRNA.BRCA1.670 | 99,499 | RGB | R | G | BG |
| gRNA.BRCA1.671 | 99,578 | RGB | R | B | RGB |
| gRNA.BRCA1.672 | 99,858 | RGB | R | B | RB |
| gRNA.BRCA1.673 | 99,989 | RGB | R | B | BG |
| gRNA.BRCA1.674 | 100,077 | RGB | G | RGB | RG |
| gRNA.BRCA1.675 | 100,078 | RGB | G | RGB | RB |
| gRNA.BRCA1.676 | 100,252 | RGB | G | RGB | BG |
| gRNA.BRCA1.677 | 100,253 | RGB | G | RGB | R |
| gRNA.BRCA1.678 | 100,267 | RGB | G | RGB | G |
| gRNA.BRCA1.679 | 100,333 | RGB | G | RG | RGB |
| gRNA.BRCA1.680 | 100,512 | RGB | G | RG | RB |
| gRNA.BRCA1.681 | 100,551 | RGB | G | RG | BG |
| gRNA.BRCA1.682 | 100,672 | RGB | G | RG | R |
| gRNA.BRCA1.683 | 100,697 | RGB | G | RG | G |
| gRNA.BRCA1.684 | 100,848 | RGB | G | RG | B |
| gRNA.BRCA1.685 | 100,884 | RGB | G | RB | RGB |
| gRNA.BRCA1.686 | 100,942 | RGB | G | RB | RG |
| gRNA.BRCA1.687 | 101,036 | RGB | G | RB | BG |
| gRNA.BRCA1.688 | 101,094 | RGB | G | RB | R |
| gRNA.BRCA1.689 | 101,186 | RGB | G | RB | G |
| gRNA.BRCA1.690 | 101,204 | RGB | G | RB | B |
| gRNA.BRCA1.691 | 101,219 | RGB | G | BG | RGB |
| gRNA.BRCA1.692 | 101,286 | RGB | G | BG | RG |
| gRNA.BRCA1.693 | 101,483 | RGB | G | BG | RB |
| gRNA.BRCA1.694 | 101,488 | RGB | G | BG | R |
| gRNA.BRCA1.695 | 101,709 | RGB | G | BG | G |
| gRNA.BRCA1.696 | 101,841 | RGB | G | BG | B |
| gRNA.BRCA1.697 | 101,844 | RGB | G | R | RGB |
| gRNA.BRCA1.698 | 101,845 | RGB | G | R | RG |
| gRNA.BRCA1.699 | 101,846 | RGB | G | R | RB |
| gRNA.BRCA1.700 | 101,909 | RGB | G | R | BG |
| gRNA.BRCA1.701 | 101,972 | RGB | B | RGB | RG |
| gRNA.BRCA1.702 | 102,080 | RGB | B | RGB | RB |
| gRNA.BRCA1.703 | 102,348 | RGB | B | RGB | BG |
| gRNA.BRCA1.704 | 102,360 | RGB | B | RG | RGB |
| gRNA.BRCA1.705 | 102,471 | RGB | B | RG | RB |
| gRNA.BRCA1.706 | 102,654 | RGB | B | RG | BG |
| gRNA.BRCA1.707 | 102,655 | RGB | B | RB | RGB |
| gRNA.BRCA1.708 | 102,823 | RGB | B | RB | RG |
| gRNA.BRCA1.709 | 102,882 | RGB | B | RB | BG |
| gRNA.BRCA1.710 | 102,889 | RGB | B | RB | G |
| gRNA.BRCA1.711 | 102,981 | RGB | B | BG | RGB |
| gRNA.BRCA1.712 | 103,008 | RGB | B | BG | RG |
| gRNA.BRCA1.713 | 103,018 | RGB | B | BG | RB |
| gRNA.BRCA1.714 | 103,039 | RGB | B | BG | R |
| gRNA.BRCA1.715 | 103,059 | RGB | B | R | RG |
| gRNA.BRCA1.716 | 103,143 | RGB | B | R | BG |
| gRNA.BRCA1.717 | 103,168 | RGB | B | G | RG |
| gRNA.BRCA1.718 | 103,438 | RGB | RGB | RG | RGB |
| gRNA.BRCA1.719 | 103,446 | RGB | RGB | RG | RB |
| gRNA.BRCA1.720 | 103,459 | RGB | RGB | RG | BG |
| gRNA.BRCA1.721 | 103,472 | RGB | RGB | RG | R |
| gRNA.BRCA1.722 | 103,555 | RGB | RGB | RG | G |
| gRNA.BRCA1.723 | 103,559 | RGB | RGB | RB | RGB |
| gRNA.BRCA1.724 | 103,606 | RGB | RGB | RB | RG |
| gRNA.BRCA1.725 | 103,670 | RGB | RGB | RB | BG |
| gRNA.BRCA1.726 | 103,699 | RGB | RGB | RB | R |
| gRNA.BRCA1.727 | 103,700 | RGB | RGB | RB | G |
| gRNA.BRCA1.728 | 103,738 | RGB | RGB | RB | B |
| gRNA.BRCA1.729 | 103,755 | RGB | RGB | BG | RGB |
| gRNA.BRCA1.730 | 103,756 | RGB | RGB | BG | RG |
| gRNA.BRCA1.731 | 103,769 | RGB | RGB | BG | RB |
| gRNA.BRCA1.732 | 103,790 | RGB | RGB | BG | R |
| gRNA.BRCA1.733 | 103,811 | RGB | RGB | BG | G |
| gRNA.BRCA1.734 | 103,824 | RGB | RGB | R | RGB |
| gRNA.BRCA1.735 | 103,880 | RGB | RGB | R | RG |
| gRNA.BRCA1.736 | 103,881 | RGB | RGB | R | RB |
| gRNA.BRCA1.737 | 104,232 | RGB | RGB | R | BG |
| gRNA.BRCA1.738 | 104,563 | RGB | RGB | G | RGB |
| gRNA.BRCA1.739 | 104,659 | RGB | RGB | G | RG |
| gRNA.BRCA1.740 | 105,115 | RGB | RGB | G | RB |
| gRNA.BRCA1.741 | 105,270 | RGB | RGB | G | BG |

Figure 8:
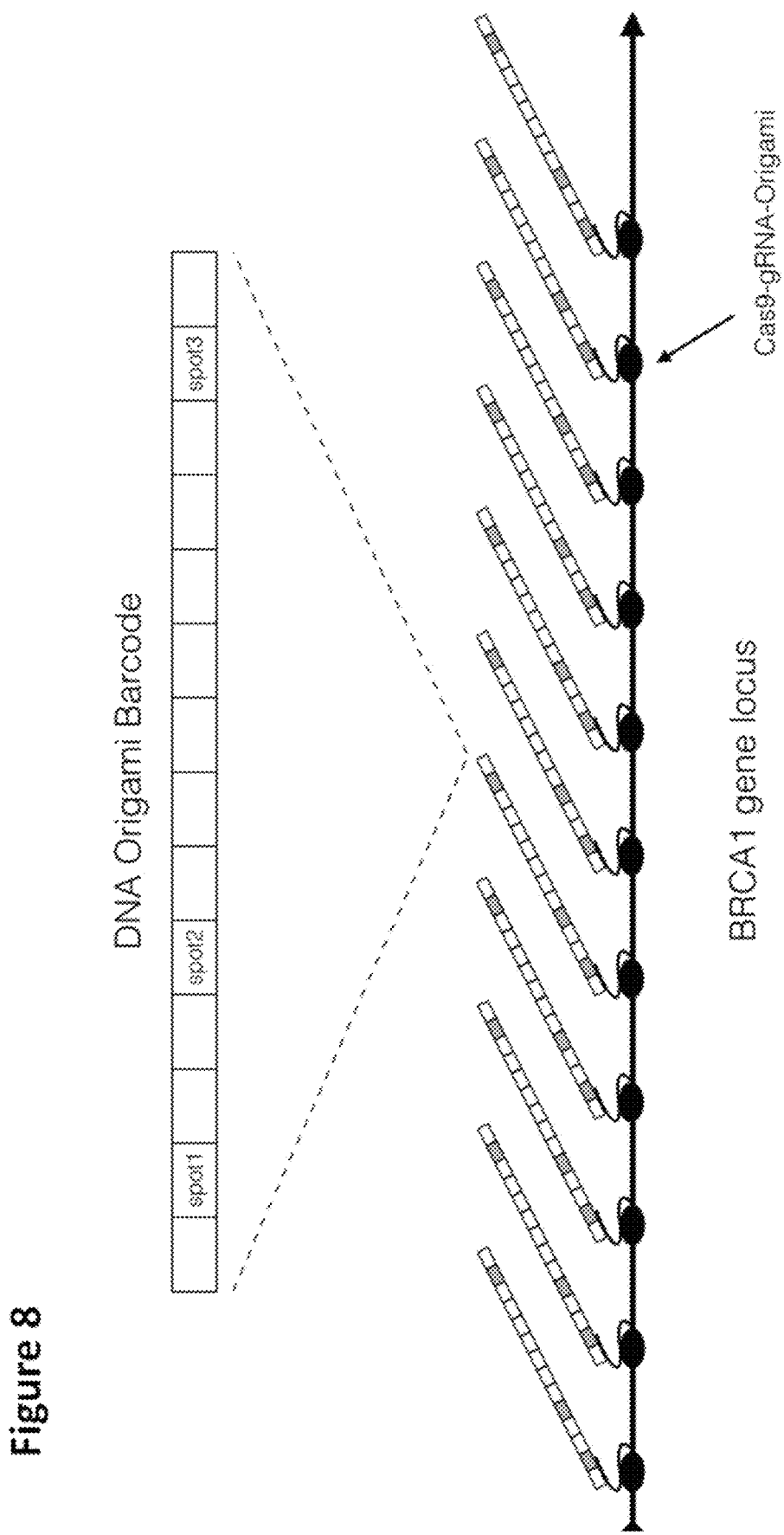
FIG. 8 presents a diagram for identifying genomic regions using origami barcodes attached to gRNA/Cas9.

Another example uses Origami Codes (see Nat Chem. 2012 October; 4(10):832-9.); see FIG. 8. Nucleic Acid origami methods are known to those of skill in the art. gRNA tails are barcoded according to the origami multicolor scheme listed in Table 3. The barcodes are segregated in a way that forms an expected sequential gRNA pattern. According to this scheme, the origami is the gRNA tail probe. Each origami multicolor probe has an attachment specific to a gRNA, meaning that for 741 origami probes, we have 741 unique gRNA tail sequences. An origami multicolor probe has 3 attachment locations for fluorescent labels, which can be physically resolved via high-resolution or super-resolution imaging, i.e Spot1, Spot2, Spot3. Each Spot has a variety of color code associated to it. The combination of these codes provide the identity of the origami multicolor probe.

The gRNA barcodes are detected via addition of their respective fluorescently labeled origami multicolor probes. The actual sequential gRNA pattern is revealed. Any unexpected patterns will be identified as a genomic rearrangement. Compared with the Locational RGB Code example, which resolve regions of the locus, the Origami Code can resolve at the single gRNA level, providing a much higher and detailed identification of a genomic region or the arrangement on the locus.

Her2 Assay

Determination of Her2 status is recommended for all invasive breast cancer using in situ hybridization techniques. A recent review of currently approved clinical diagnostics highlighted the current challenged of the different clinical assays (Reference: Franchet C, Filleron T, Cayre A, Mounié E, Penault-Llorca F, Jacquemier J, Macgrogan G, Arnould L, Lacroix-Triki M. Instant-quality fluorescence in-situ hybridization as a new tool for HER2 testing in breast cancer: a comparative study. Histopathology. 2014 January; 64(2): 274-83).

Multiple challenges are reported with the current assays available. For one, traditional FISH is a lengthy process, which typically requires a day to prepare the sample for hybridization (deparaffinization, pretreatment, pepsin digestion, denaturation), a lengthy hybridization is performed during 12-24 h, and the following day the hybridization is washed extensively and visualization is performed.

According to exemplary aspects described herein, methods do not require any pretreatment, pepsin digestion or denaturation of the sample. Cas9-gRNA complexes can readily and specifically hybridize to native double stranded DNA in fixed sample. Also non-hybridized complexes are easily washed away. Therefore, the overall process can be performed within a day. This timeline is on par with the Her2 immunohistochemistry assay that traditionally precedes the FISH assay. Moreover, the encoding method would allow for both the IHC and Cas9-gRNA FISH to proceed concomitantly.

Accuracy and discrepancies between assays are also being reported as a problem. Considering the high cost of breast cancer treatment, often year long, the wrong treatment results in considerable social and economic impacts. According to certain aspects described herein, Cas9-gRNA are encoded in a way that provide redundancy and colocalization. The positive samples can be distinguished compared to aberration. Moreover, methods described herein allow for re-probing of the sample, i.e. the probe can be removed, while the Cas9-gRNA stays bound to the target DNA, and a new round of probing can be performed under more stringent conditions.

Current FISH assays cost a few hundreds of dollars (Reference: world wide website ncbi.nlm.nih.gov/pmc/articles/PMC2706184/). This is partly due to the material being used for the probes, which in some case is a very long DNA copy inserted in a large vector with intercalating fluorescent molecule (PathVysion), or expensive peptide nucleic acid (PNA) probes (pharmDx), or use of antibody and secondary antibody to detect the DNA probe (IN-FORM). Methods described herein would bring the cost on par with the traditionally Her2 ICH test (~100$) that precedes the FISH assay. The Cas9 is a protein of bacterial origin and is efficiently expressed and purified from inexpensive bacterial system. It is also available commercially. The synthesis of the gRNA templates in an oligonucleotide array synthesizer is the most inexpensive way to currently synthesize DNA (0.0004$/base, commercial price). After the array synthesis, the oligonucleotide can be amplified using PCR, thereby creating a pool of gRNA templates that can be inexpensively re-amplified indefinitely. In vitro transcription is very efficient, producing 500 to 1000 RNA molecules per DNA molecule.

The Her2 assay reports the average number of copies of Her2 locus per cell as a ratio of chromosome 17. The most common reporters for chromosome 17 target the alpha satellite repeats of the centromeric region. This is a region that has been relatively well characterized and contains up to 1000 monomeric repeats (see Waye J S, Willard H F. Structure, organization, and sequence of alpha satellite DNA from human chromosome 17: evidence for evolution by unequal crossing-over and an ancestral pentamer repeat shared with the human X chromosome. Mol Cell Biol. 1986 September; 6(9):3156-65). Repeats are especially well suited to Cas9-gRNA methods described herein. In this case, only a few different gRNAs are required. Table 4 presents a list of gRNA targets. This list was extracted from the well characterized D17Z1 locus, from which other CEP17 probes are based from. This list would also cover variants as reported by O'Keefe C L, Warburton P E, Matera A G. Oligonucleotide probes for alpha satellite DNA variants can distinguish homologous chromosomes by FISH. Hum Mol Genet. 1996 November; 5(11):1793-9). However, with methods described herein, only 11 gRNAs can be used to target most of those repeats, since Cas9 typically allows for 1-2 mismatches near it's 5'end (Table 5).

TABLE 4

| Target name | Target Sequence |
|---|---|
| CEN17.1 | GAGCGCTTTCAGGCCTGTGGTGG (SEQ ID NO: 73) |
| CEN17.2 | GAGGGCTTTGAGGCCTGTGGTGG (SEQ ID NO: 74) |
| CEN17.3 | GAGGGCTTTGTGGTTTGTGGTGG (SEQ ID NO: 75) |
| CEN17.4 | GGAATCTGCAAGTGGATATGTGG (SEQ ID NO: 76) |
| CEN17.5 | GTGTTGAAACTCTCTTTTTGTGG (SEQ ID NO: 77) |
| CEN17.6 | GTTTCCAATCACTCTTTGTGTGG (SEQ ID NO: 78) |
| CEN17.7 | GTTTGGAAACACTCTTGTTGTGG (SEQ ID NO: 79) |
| CEN17.8 | GTTTTGAAACTCTCTTTCTGTGG (SEQ ID NO: 80) |
| CEN17.9 | ACACTGCTCTATCCATAGGAGG (SEQ ID NO: 81) |
| CEN17.10 | AGATATTTGGACCGCTCTGAGG (SEQ ID NO: 82) |
| CEN17.11 | AGCGCTTTCAGGCCTGTGGTGG (SEQ ID NO: 83) |
| CEN17.12 | AGGAATGTTCAACTCTGTGAGG (SEQ ID NO: 84) |
| CEN17.13 | AGGGCTTTGAGGCCTGTGGTGG (SEQ ID NO: 85) |
| CEN17.14 | AGGGCTTTGTGGTTTGTGGTGG (SEQ ID NO: 86) |
| CEN17.15 | CATCACAGAGAAGCTTCTGAGG (SEQ ID NO: 87) |
| CEN17.16 | CTGCATTCAACTCACAGTGTGG (SEQ ID NO: 88) |
| CEN17.17 | GAAAGGAAAGTTCAACTCGGGG (SEQ ID NO: 89) |
| CEN17.18 | GAATCTGCAAGTGGATATGTGG (SEQ ID NO: 90) |
| CEN17.19 | GAATGCAAACATCACGAAGAGG (SEQ ID NO: 91) |
| CEN17.20 | GCATATTTGGACCTCTTTGAGG (SEQ ID NO: 92) |
| CEN17.21 | GCTTCTGTTTAGTTCTGTGCGG (SEQ ID NO: 93) |
| CEN17.22 | GCTTCTGTTTAGTTCTGTGCGG (SEQ ID NO: 94) |
| CEN17.23 | GGACATTTGGAGGGCTTTGAGG (SEQ ID NO: 95) |
| CEN17.24 | GGACGTTTGGAGGGCTTTGTGG (SEQ ID NO: 96) |
| CEN17.25 | GGAGATTTGGAGCGCTTTGAGG (SEQ ID NO: 97) |
| CEN17.26 | GGATATTTAGGCCTCTCTGAGG (SEQ ID NO: 98) |
| CEN17.27 | GGATATTTGGACCACTCTGTGG (SEQ ID NO: 99) |
| CEN17.28 | GGATATTTGGACCTCTCTGAGG (SEQ ID NO: 100) |
| CEN17.29 | GGGATCATTGCACTCTTTGAGG (SEQ ID NO: 101) |
| CEN17.30 | TACTACCATAGGCCTAAAGCGG (SEQ ID NO: 102) |
| CEN17.31 | TATTTGTAGAATGTGCAAGTGG (SEQ ID NO: 103) |
| CEN17.32 | TCCAAAGACATCTTCGGAGAGG (SEQ ID NO: 104) |
| CEN17.33 | TCCAACGAAATCCTCAGAGAGG (SEQ ID NO: 105) |
| CEN17.34 | TCCAACGAAATCCTCAGAGAGG (SEQ ID NO: 106) |
| CEN17.35 | TCCAACGAAATCCTCAGAGCGG (SEQ ID NO: 107) |
| CEN17.36 | TCCAACGAAATCTTCAAAGAGG (SEQ ID NO: 108) |
| CEN17.37 | TCCAACGAAATGCTCAGAGAGG (SEQ ID NO: 109) |
| CEN17.38 | TCGAACGAAGGACACAGAGTGG (SEQ ID NO: 110) |
| CEN17.39 | TCGAACGAAGGCCACAGAGTGG (SEQ ID NO: 111) |

TABLE 4-continued

| Target name | Target Sequence |
|---|---|
| CEN17.40 | TCTGCAAGTGGACATTTGGAGG (SEQ ID NO: 112) |
| CEN17.41 | TCTGCAAGTGGACGTTTGGAGG (SEQ ID NO: 113) |
| CEN17.42 | TGGAGCGCTTTCAGGCCTGTGG (SEQ ID NO: 114) |
| CEN17.43 | TGGAGGGCTTTGAGGCCTGTGG (SEQ ID NO: 115) |
| CEN17.44 | TGGAGGGCTTTGTGGTTTGTGG (SEQ ID NO: 116) |
| CEN17.45 | TGTTGAAACTCTCTTTTTGTGG (SEQ ID NO: 117) |
| CEN17.46 | TTGTTGTGGAATGTGCAAGTGG (SEQ ID NO: 118) |
| CEN17.47 | TTTCCAATCACTCTTTGTGTGG (SEQ ID NO: 119) |
| CEN17.48 | TTTCTGTGGCATCTGCAAGGGG (SEQ ID NO: 120) |
| CEN17.49 | TTTGGAAACACTCTTGTTGTGG (SEQ ID NO: 121) |
| CEN17.50 | TTTGTGTAGAATCTGCAAGTGG (SEQ ID NO: 122) |
| CEN17.51 | TTTGTGTGGAATCTGCAAGTGG (SEQ ID NO: 123) |
| CEN17.52 | TTTTCGTAGTGTCTACAAGTGG (SEQ ID NO: 124) |
| CEN17.53 | TTTTGAAACTCTCTTTCTGTGG (SEQ ID NO: 125) |
| CEN17.54 | TTTTTCCAGAATCTGCAAGTGG (SEQ ID NO: 126) |
| CEN17.55 | TTTTTCTAGAATCTGCAAGTGG (SEQ ID NO: 127) |
| CEN17.56 | TTTTTGCAGGATCTACAAGTGG (SEQ ID NO: 128) |
| CEN17.57 | TTTTTGTACAATCTACAAGTGG (SEQ ID NO: 129) |
| CEN17.58 | TTTTTGTAGAAACTGCAAGGGG (SEQ ID NO: 130) |
| CEN17.59 | TTTTTGTAGAAACTGCAAGTGG (SEQ ID NO: 131) |
| CEN17.60 | TTTTTGTAGGATCTGCAAGTGG (SEQ ID NO: 132) |
| CEN17.61 | TTTTTGTGGAATCTGCAAGTGG (SEQ ID NO: 133) |

TABLE 5

| gRNA name | gRNA target sequence |
|---|---|
| Cen17gRNA.1 | GAGGGCTTTGAGGCCTGTGG (SEQ ID NO: 134) |
| Cen17gRNA.2 | GTGTTGAAACTCTCTTTTTG (SEQ ID NO: 135) |
| Cen17gRNA.3 | GACACTGCTCTATCCATAGG (SEQ ID NO: 136) |
| Cen17gRNA.4 | GAGGGCTTTGAGGCCTGTGG (SEQ ID NO: 137) |
| Cen17gRNA.5 | GGAATCTGCAAGTGGATATG (SEQ ID NO: 138) |
| Cen17gRNA.6 | GGCATATTTGGACCTCTTTG (SEQ ID NO: 139) |
| Cen17gRNA.7 | GTACTACCATAGGCCTAAAG (SEQ ID NO: 140) |
| Cen17gRNA.8 | GTCCAACGAAATCCTCAGAG (SEQ ID NO: 141) |
| Cen17gRNA.9 | GTCTGCAAGTGGACATTTGG (SEQ ID NO: 142) |
| Cen17gRNA.10 | GTTGTTGTGGAATGTGCAAG (SEQ ID NO: 143) |
| Cen17gRNA.11 | GTTTGTGTAGAATCTGCAAG (SEQ ID NO: 144) |

Additionally, methods described herein allow for screening allelic variants, which is essential information in personalized medicine, and can influence the treatment. By example, the Her2 variant I655V has been implicated in reduced efficiency of tamoxifen as a breast cancer treatment, which should be considered (see Chang N W, Chen D R, Chen F N, Lin C, Wu C T. HER2 codon 655 G-allele is associated with reductions in plasma high-density lipoprotein levels in breast cancer patients treated with tamoxifen. J Investig Med. 2011 December; 59(8):1252-7. doi: 10.231/JIM.0b013e3182354923). Two identified gRNAs target could be used to identify the variants (target 1: TCTGACGTCCATCATCTCTGCGG, (SEQ ID NO:145) and target 2 GCCAACCACCGCAGAGATGATGG (SEQ ID NO:146)). Using a set of 4 gRNAs (2 per target) with allele-specific barcodes, methods are provided to discriminate between the Isoleucine allele (ATC) or Valine allele (GTC), as part of a standard Her2 assay.

It is understood that other regions of chromosome 17 could be targeted. By example, Top2A is located in proximity to the Her2 locus and has been observed to co-amplify with Her2, which can also impact the choice for a proper treatment. See Smith K, Houlbrook S, Greenall M, Carmichael J, Harris A L. Topoisomerase II alpha co-amplification with erbB2 in human primary breast cancer and breast cancer cell lines: relationship to m-AMSA and mitoxantrone sensitivity. Oncogene. 1993 April; 8(4):933-8.

An example of a FISH protocol for screening Her2/CEN17 is described below. If both immunohistochemistry and FISH assays are to be performed on the same sample, cells or tissue samples are fixed on a microscope compatible support (e.g. clean borosilicate microscope slide or microscope cover slip) in 10% Paraformaldehyde in PBS at 4° C. between 1 h to 16 h. Alternatively, samples can be fixed in 100% methanol at −20° C., for 20 minutes to 1 h (methanol is more efficient at retaining DNA in the sample, while extracting many proteins). Paraffin embedded tissue sections should de-paraffined, before being affixed to the slide, which is typically accomplished by 5 minutes incubation in xylene, followed by two ethanol washes, and once with water. Fixed samples are then washed once with PBST (PBS buffer with 0.5% Tween-20) and then incubated for 5 minutes with PBS containing 0.5% Triton X-100. The samples are then washed in PBST and the Cas9-gRNA-label complex mixture is added to the sample in PBST with 5 mM $MgCl_2$, and incubated at 37° C. between 2 h to 16 h (i.e. the mix contains both sets for Her2 and CEN17 and their respective labels for identification). After incubation, unbound Cas9 is removed by 3 washes in PBST at 37° C. The samples are mounted with an antifade mounting reagent with DAPI (e.g. ProLong or VectaShield containing DAPI), and sealed. The samples are imaged using an oil immersion 63× objectives. Alternatively, the samples are stable for several weeks if kept protected from light and at 4° C. At least 20 nuclei in a tumor area are then counted and for each of them, the number of Her2 and CEN17 localization foci are recorded. The ratio of Her2 to CEN17 can be calculated and reported in accordance with current clinical practice as prescribed by the 2013 ASCO/CAP guidance (see Wolff A C, Hammond M E, Hicks D G, Dowsett M, McShane L M, Allison K H, Allred D C, Bartlett J M, Bilous M, Fitzgibbons P, Hanna W, Jenkins R B, Mangu P B, Paik S, Perez E A, Press M F, Spears P A, Vance G H, Viale G, Hayes D F; American Society of Clinical Oncology; College of American Pathologists. Recommendations for human epidermal growth factor receptor 2 testing in breast cancer: American Society of Clinical Oncology/College of American Pathologists clinical practice guideline update. J Clin Oncol. 2013 Nov. 1; 31(31):3997-4013).

Example III

FIG. 1A-1E are directed to in situ Cas9-gRNA probing of Major and Minor satellites, and Telomere regions of the mouse embryonic fibroblast cell nucleus. Three gRNAs were synthesized with fluorescently labeled UTP, to target the mouse Major satellite repeat (Cy5), Minor satellite repeat (Alexa-488), and Telomere (Cy3). (FIG. 1 legend: Major satellites (A), Minor satellites (B), Telomeres (C), DAPI staining of genomic DNA (D), and overlay picture (E).) The gRNAs were complexed with Cas9 before being added to PFA-fixed samples according to the protocol described herein. The pattern fits expected probing for these targets (see Guenatri M, Bailly D, Maison C, Almouzni G. Mouse centric and pericentric satellite repeats form distinct functional heterochromatin. J Cell Biol. 2004 Aug. 16; 166(4):493-505). Pictures were taken on a Zeiss Axio Observer Z1 equipped with a 63×/1.40 oil immersion objective, and LED light source and filters appropriate for each fluorescent channels. The following legend is associated with FIG. 1: A, Major satellites; B, Minor satellites; C, Telomeres; DAPI staining of DNA; E, overlay.

Example IV

FIG. 2A-2E are directed to a control experiment for FIG. 1A-1E. Commonly used FISH oligonucleotides targeting the mouse Major satellite repeat (Cy5), Minor satellite repeat (Alexa-488), and Telomere (Cy3), where used using the same Cas9 probing protocol used in FIG. 1A-1E. Except for DAPI staining of DNA (D), other fluorescent signals were more diffuse than pictures captured in FIG. 1A-1E, and had to be highly contrasted on the microscope. (FIG. 2 legend: Major satellites (A), Minor satellites (B), Telomeres (C), DAPI staining of genomic DNA (D), and overlay picture (E).) The lack of denaturation prevented these FISH oligos from hybridizing to their targets, which also aggregated outside the nucleus. Pictures were taken on a Zeiss Axio Observer Z1 equipped with a 63×/1.40 oil immersion objective, and LED light source and filters appropriate for each fluorescent channels. The following legend is associated with FIG. 1: A, Major satellites; B, Minor satellites; C, Telomeres; DAPI staining of DNA; E, overlay.

Example V

Figure 3:
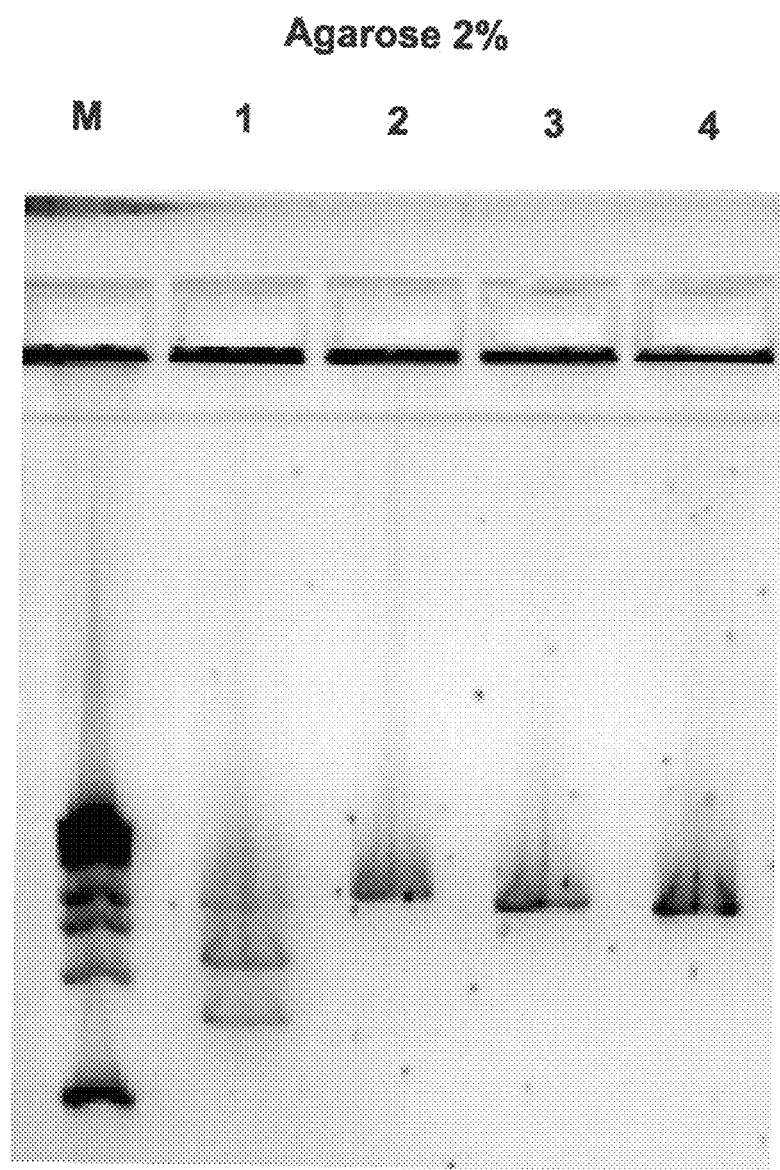
FIG. 3 presents an agarose gel of gRNA/Cas9 cleavage and gel shift assay.

FIG. 3 is directed to a Cas9-gRNA gel shift and cleavage assay showing that native Cas9 binding and cleavage activities are independent and depend on the presence or absence of magnesium ions. Reactions were prepared as follow: 2 pmol of nuclease active Cas9 (NEB), 2 pmol of synthesized Grna (targeting Lambda DNA at position L22116), and 0.2 pmol of a 2 kb PCR amplified DNA fragment (from Lambda DNA L21333-L23332), were mixed and incubated at 37° C. for 1 h in the presence of 5 Mm $MgCl_2$ (lane 1) or absence of magnesium (lane 2). Lane 1 shows secondary cleavage products in presence of magnesium, while lane 2 shows absence of cleavage product, but a small upward shift caused by the complex still being bound to it. Lane 3 and Lane 4 were performed under similar conditions as lanes 1 and 2 respectively, except that the Cas9 protein was omitted from the reaction. No cleavage and no shift are observed for lanes 3 and 4.

Example VI

Figure 4A:
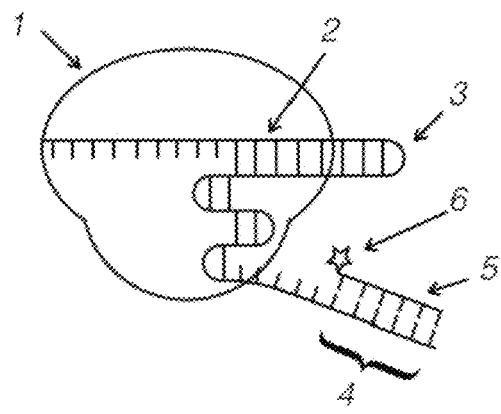
Figure 4B:
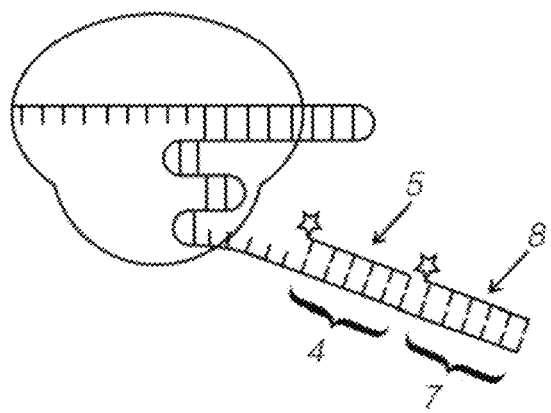
Figure 4C:
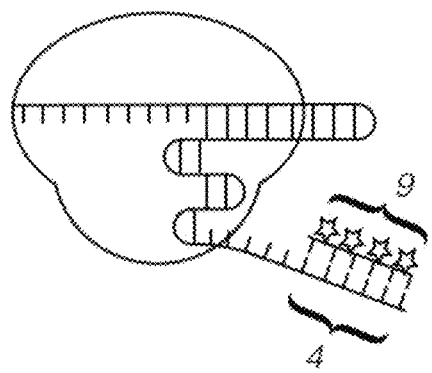
Figure 4D:
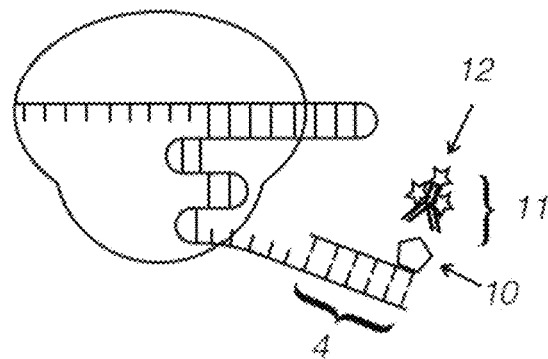

FIGS. 4A-4L are directed to examples of gRNA tail barcode and probing. FIG. 4A describes a Cas9 protein (1) and complexed gRNA (2) with projecting tetraloop (3) and projecting gRNA tail bearing a barcode (4). The barcode is detected by a hybridizing probe (5) bearing a detectable moiety, or label (6). FIG. 4B shows that the gRNA tail can be encoded by more than one barcode. In FIG. 4B, two barcodes are depicted (4 and 7), which can be detected by their respective hybridizing probes (5 and 8) bearing a detectable moiety, or label (6). In FIG. 4C, the hybridizing probe can bear multiple detectable moieties, or labels (9) in order to amplify the signal. In FIG. 4D, the detectable moiety might not be directly detectable (10) and can necessitate the use of secondary detectable agent (11), which has specific affinity for the detectable moiety. This secondary agent bears detectable moieties or labels (12) for the detection or to amplify the signal being detected. FIGS. 4E to 4I describe a way to probe the gRNA tail via rolling circle amplification. FIG. 4E describes a Cas9 protein (1) and complexed gRNA (2) with protruding tetraloop (3) and gRNA tail bearing a barcode (4). The barcode is detected by a circular hybridizing probe (13), with affinity for the barcode in one region of the probe and a labeled-probe hybridizing target site in another region (14). FIG. 4F depicts that the circular probe (13) can serve as a template for a rolling circle amplification polymerase (15) to extend the gRNA tail (16). FIG. 4G depicts that the rolling circle amplification creates a localized amplified hybridizing probe (17) with a multiply of closely localized labeled-probe hybridizing target sites (18). FIG. 4H depicts that the labeled-probe hybridizing target sites can be made detectable by the addition of detectable probes (19), resulting a signal amplified gRNA tail probe (20). FIG. 4I depicts a rolling circle amplified probe (20) similar to FIG. 4H, which is generated and labeled (21) without having the circular probe hybridized to the gRNA barcode, thereby avoiding rolling circle amplification and labeling steps on the gRNA itself. This off-gRNA generated probe can hybridize via region (5) to the barcode region of the gRNA tail as in FIG. 4A (4). FIGS. 4J to 4L describe ways to probe the gRNA tail via nucleic acid self-assembly. FIG. 4J depicts linear assembly of nucleic acid probes to each other in a sequential way. The first fragment composed of barcode hybridizing region (5), the assembly region (21) and a label (6) is first hybridized to the gRNA tail barcode (FIG. 4A, 4). A mixture of labeled assembly fragments (22 and 23), which are partially complementary to 21 or 22 or 23 are added and will self assemble, for as long as there are partially complementary fragments present in the reaction. Only a portion of the structure is depicted here. This is similar to previously described hybridization chain reaction (HCR). See Dirks R M, Pierce N A. Triggered amplification by hybridization chain reaction. Proc Natl Acad Sci USA. 2004 Oct. 26; 101(43):15275-8). FIG. 4K depicts the self assembly of a hyper-branched nucleic acid probe dendrimer structure. The first fragment composed of barcode hybridizing region (5), the assembly region (24) and a label (6) is first hybridized to the gRNA tail barcode (FIG. 4A, 4). A mixture of labeled assembly fragments (24, 25, and 26), which are partially complementary to 24 or 25 or 26 are added and will self assemble into a hyper-branched structure, for as long as there are partially complementary fragments present in the reaction. Only a portion of the structure is depicted here. This kind of nucleic acid dendrimers have been described previously. See Li Y, Tseng Y D, Kwon S Y, D'Espaux L, Bunch J S, McEuen P L, Luo D. Controlled assembly of dendrimer-like DNA. Nat Mater. 2004 January; 3(1):38-42). FIG. 4L depicts an assembly of branches of nucleic acid probes to linearly amplify the signal. The first fragment composed of barcode hybridizing region (5), the assembly region (27) is first hybridized to the gRNA tail barcode (FIG. 4A, 4). A mixture of labeled assembly fragments (29 and 30), which are partially complementary to 27 or 29 or 30 are added and can self assemble. A detectable probe (28) can hybridize to a portion of the assembly fragments (27) and (30), for as long as there are partially complementary fragments present in the reaction. Only a portion of the structure is depicted here. This is similar to previously described branched DNA (bDNA). See Collins M L, Irvine B, Tyner D, Fine E, Zayati C, Chang C, Horn T, Ahle D, Detmer J, Shen L P, Kolberg J, Bushnell S, Urdea M S, Ho D D. A branched DNA signal amplification assay for quantification of nucleic acid targets below 100 molecules/ml. Nucleic Acids Res. 1997 Aug. 1; 25(15):2979-84).

It is understood that the detectable moieties (e.g. 6, 9, 10, 12) can provide several means of detection, such as fluorescent, chemiluminescent or chromogenic, or resonant. It is understood that the hybridizing probes (e.g. 5, 8, 9, 14) can be made of various nucleic acid components, such as DNA, RNA, modified DNA, modified RNA.

Example VII

Figure 5B:
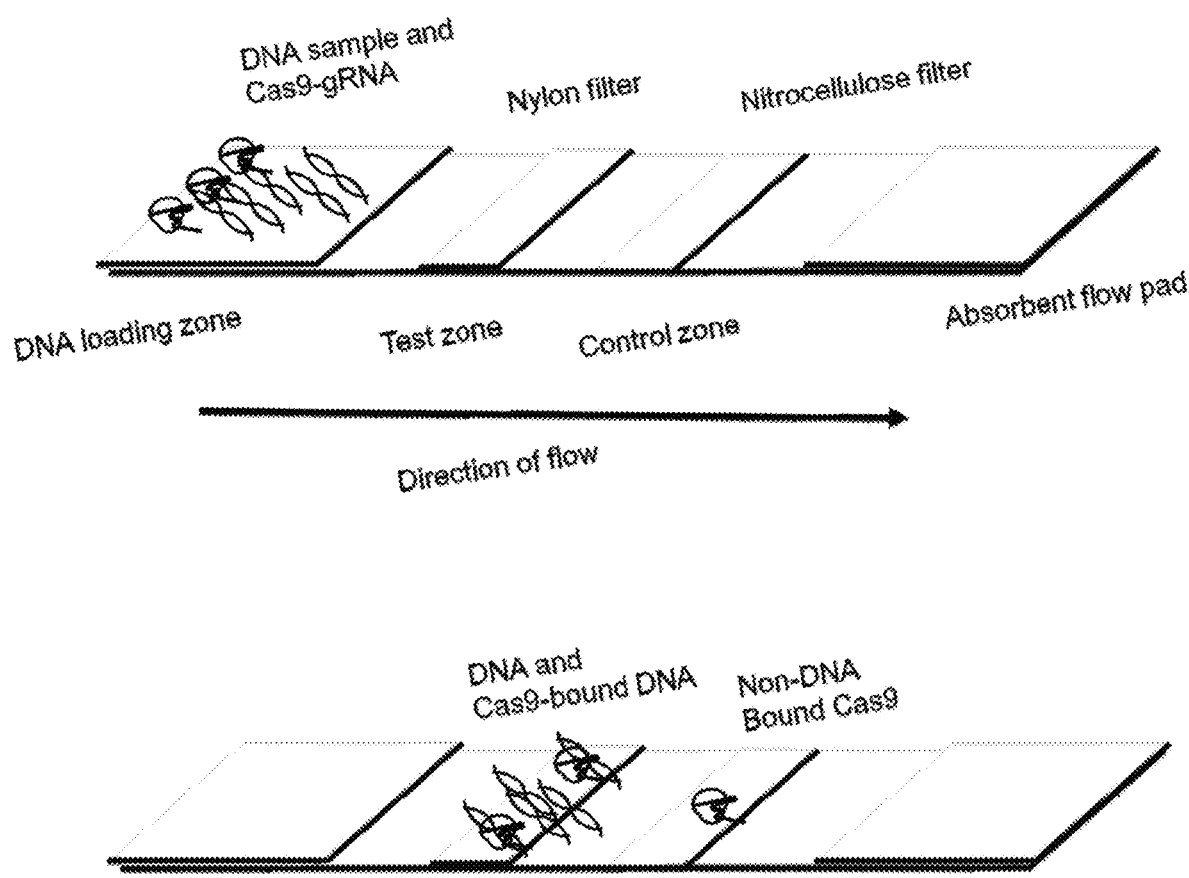

FIG. 5A is directed to a Cas9-gRNA complex being attached to a surface of a lateral flow test system. A population of DNA being investigated is loaded on the system and lateral flow displaces it to the Test Zone where the target-specific Cas9-gRNA binds to specific DNA. The rest of the DNA keeps flowing through the end of the assay and is capture by the Control Zone, while the target DNA stay bound to the Cas9-gRNA complex at the Test Zone. DNA detection can be performed via nucleic acid stains, or hybridization of a detectable probe to the DNA, or via covalent attachment of a detectable probe to the DNA, or by enzymatic amplification of the DNA (e.g. isothermal amplification) in the presence of specific or universal oligonucleotide primers bearing detectable moieties. Detectable moieties often used in a lateral flow assay include gold or silver nanoparticles. Other moieties such as biotin, digoxigenin, dinitrophenyl, fluorescein are commonly used in combination with secondary detection agents (e.g. gold or silver coated antibodies specific to biotin, digoxigenin, dinitrophenyl or fluorescein). FIG. 5B is directed to a lateral flow system using two materials with different properties for retaining DNA or proteins, such as hydrophobicity or charges. By example, a nitrocellulose membrane retains proteins more favorably that DNA, while a nylon membrane binds DNA over proteins. Upon loading the population of DNA to be investigated, the Cas9-gRNA complex binds the target DNA. Cas9 bound to DNA is retained by the DNA retention membrane at the Test Zone, while unbound Cas9 would pass through and bind to the protein retention membrane at the Control Zone. Detection is performed to detect the Cas9-gRNA complex with DNA. The gRNA is probed in ways described herein. Alternatively, the Cas9 protein itself can carry moieties (e.g. gold nanoparticles, silver nanoparticles, biotin, digoxigenin, dinitrophenyl, fluorescein). FIG. 5C is directed to a lateral flow system where the population of DNA to be investigated is first captured on the surface of the Test Zone via molecular interactions (e.g. charge, hydrophobicity, covalent interaction, or affinity interaction such as biotin-streptavidin). The Cas9-gRNA is then bound to the surface-captured target DNA at the Test Zone. Remaining unreacted Cas9-gRNA passes through and is captured at the Control Zone. Detection is to be performed to detect the Cas9-gRNA complex with DNA. The gRNA is probed in ways described herein. Alternatively, the Cas9 protein itself could carry moieties (e.g. gold nanoparticles, silver nanoparticles, biotin, digoxigenin, dinitrophenyl, fluorescein).

Example VIII

Probing Target DNA Using a Guide RNA/Cas9 Complex

Guide RNAs were designed, prepared, expressed and purified in vitro. Single stranded DNA (ssDNA) oligonucleotides are synthesized (IDT or CustomArray chip). These oligos contain a T7 transcription start site for in vitro RNA synthesis, and an extension to form the 3'end tail to be used for probing. T7 RNA synthesis is performed, RNA is purified.

According to one aspect, the extended sequence or tail is designed to minimize steric hindrance, have low complexity and low free energy to achieve super resolution imaging using DNA-PAINT (which can achieve 2.7 nm resolution, which is 8 DNA bases, so below the 20 bp footprint of Cas9). Designed guide RNA has 20 different PAINT docking sites, which are 9 mer long and contain a different arrangement of A, T and C bases (not G), while the PAINT probes are the complementary sequence plus a fluorophore.

By washing away the probes and loading new probes between imaging, 20 probes per fluorophores can be accomplished, i.e. 20 different gRNAs can be imaged per fluorophore. Accordingly, 4 fluorophores are able to discriminate between 80 gRNAs.

One embodiment of a guide RNA structure is (5' to 3') gRNA-UUUUU-PAINTdock. The guide RNA sequence is the minimal length of the single guide RNA commonly used with SpCas9.

For high-resolution imaging, the extended sequence or tail is designed to minimize steric hindrance, have low complexity and low free energy. However, with high-resolution imaging, a longer annealing region is used. The structure of the extended sequence or tail can serve as barcode that can be probed with sequence specific oligos, or a padlock probe followed by rolling circle amplification.

SpCas9 was expressed in *E. coli*. Gibson's isothermal assembly is used to assemble and clone a Cas9 coding gene in a plasmid suitable for expression in *E. coli*. After induction, the cells are lysed and the protein is purified.

Target DNA was obtained by lysing cells with no further preparation. Accordingly, a sample includes a mixture of DNA from chromosomal and extra-chromosomal origin (e.g. plasmids).

Cas9 is mixed with gRNAs and added to the DNA sample for a time sufficient for the Cas9, gRNA and target nucleic acid to form a complex (about 15 minutes) after which are added the detection probes. Imaging data is then acquired (seconds to minutes).

For nanopore detection, Cas9-gRNA complexes bind at designed interval on a dsDNA fragment. The DNA is then translocated through or in proximity to the nanopore (or nanogap electrodes). The change in electrical current is measured: dsDNA will run at a certain current, while the complex bound to the DNA will partially block the current that we can record as a current spike. By analyzing those spike events over time, the position of the Cas9/gRNA on the target DNA can be inferred and compared to a predicted position based on guide RNA design.

Using the above methods, multiple targets can be detected at once to gain information on the nature of the DNA target, such as repeat regions of centromeres, identity of chromosomes linked to those repeats, identification of drug resistant genes (contained in a bacterial genome or a plasmid), identification of mobile elements (e.g. transposons, drug resistant cassettes), specific alleles for disease related genes (e.g. oncogene, autoimmune, neurodegenerative), etc.

Example IX

Probing Target DNA Using a Guide RNA/Cas9 Complex

Human genomic DNA (Novagen) was diluted to about 0.2 ng/ul in 0.5M MES buffer pH 5.5 and subjected to molecular combing on a vinyl silane coated substrate (Genomic Vision, Paris) according to Michalet et al (Dynamic Molecular Combing, Science 1999). Briefly, this involved dipping a vinyl silane coated cover glass into the DNA containing solution and then pulling it out at a fixed speed, akin to a Langmuir Blodgett set-up. This served to stretch the DNA onto the substrate by a "receding meniscus" mechanism. When the DNA had completely lifted out of the solution, it was UV crosslinklinked at 10,000 microJoules per square centimeter. This resulted in a large amount of DNA unidirectionally aligned on a surface. If care is taken in the preparation of the DNA, megabase lengths of DNA can be visualized using a DNA stain such as YOYO-1.

The genomic DNA stretched on the substrate was wetted with buffer, then a pre-formed (by preincubation for 10 min at 37 degrees) gRNA/cas9 (NEB) complex was added to the substrate and allowed to react for 1 hour. Excess complex was then washed away. The guide RNA was designed to have a portion complementary to a centromere sequence and the 3' end of guide was designed to have a tail nucleic acid sequence complementary to a probe sequence. One of skill will readily understand that guide RNA can be designed to any desired genomic sequence. A sequence including the guide RNA and the tail sequence, a promoter and a termination signal sequence (IDT) was used in an in vitro transcription system to synthesize the guide RNA with the tail sequence complementary to a probe sequence from the template. The guide RNA with the tail sequence complementary to a probe sequence was purified using a Zymo clean/concentrator. The transcribed RNA was then incubated with the Cas9 as described above before adding to the stretched DNA.

The slide was then treated with BLOCKAID (Invitrogen). A 16 nt DNA probe with complementarity to the tail on the gRNA sequence was then reacted with the complex under non-stringent conditions (4×SSC, 50% Formamide, Blockaid). The probe that was labeled at both ends with Atto 657N dye (custom synthesis order from Invitrogen). The hybridization reaction was left at 4 degrees C. overnight. The slide was then washed to remove excess dye and imaged on a TIRF microscope.

Because the DNA target remained double stranded, it could be stained with YOYO-1 dye before or after imaging of the Atto647N. The label on the guide RNA was detected by using a red laser and appropriate filters and the DNA stain was detected by using a blue laser and appropriate filters. Imaging was done by wide-field TIRF microscopy.

FIG. 6A is an image showing the result of centromere specific guide RNA (gRNA)/Cas9 complexes (dots) bound to double stranded human genomic DNA (line) elongated or pre-stretched on a surface. FIG. 6B is a superresolution image of the binding of gRNA/Cas9 (dots) to human centromeric DNA (gray).

As shown in FIG. 6A, the probe targeted centromeric DNA which at a rough estimate, comprises ~1% of the genome. A number of fields of view were examined and frequently fields were seen with dots of probe labeling correlated along a line, as shown in FIG. 6A. The DNA stain showed that the slide had many stretched DNA molecules that did not show labels correlating along a line, thereby demonstrating that the methods described herein can identify a particular target nucleic acid within a sample including a plurality of nucleic acids using a detectable gRNA/Cas9 complex.

The CRISPR/CAS9 buffer included 20 mM HEPES, 100 mM NaCl, 5 mM $MgCl_2$, 0.1 mM EDTA and was at a pH 6.5@25° C. The hybridization buffer included 200 ul "neat" formamide, 20 ul 10% SDS, 120 ul blockaid, 40 ul of 20×ssc and 20 ul water. The Cas9 used was Cas9 Nuclease, S. pyogenes (NEB) in a 25-30 nM final concentration. The labelled oligo (IDT) concentration used was ~800 nM.

Figure 6C:
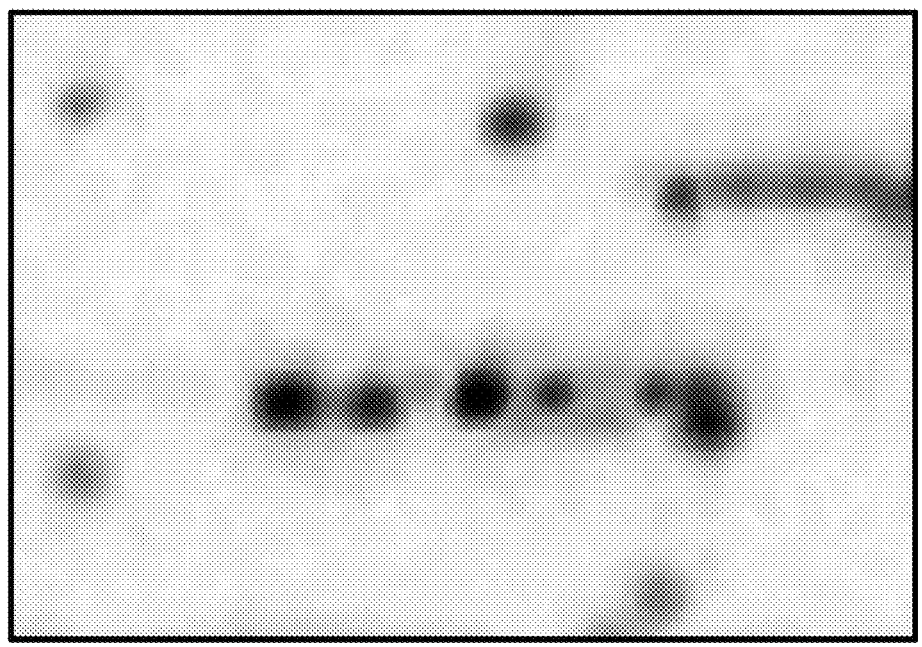

FIG. 6C is directed to a Cas9 binding assay in vitro. Full length Lambda DNA (~48 kb) is probed by Cas9 alone or complexed with CRISPR-gRNAs and stretched on a vinyl silane-functionalized glass surface. Cas9 was then labeled by a phycoerythrin-conjugated antibody (dark) and the DNA by YOYO-1 (light). Images where acquired on a Leica DM1600 with a 100×/1.47 oil objective in TIRF mode.

Example X

FIG. 7 is directed to a Locational Red-Green-Blue (RGB) barcoding system applied to the BRCA1 gene locus. Large rearrangements within the BRCA1 and BRCA2 genes are important markers for breast and ovarian cancers susceptibility in both women and men. The rearrangements can inform on the risk of developing the cancer, and the appropriate treatment. [Judkins T, Rosenthal E, Arnell C, Burbidge L A, Geary W, Barrus T, Schoenberger J, Trost J, Wenstrup R J, Roa B B. Clinical significance of large rearrangements in BRCA1 and BRCA2. Cancer. 2012 Nov. 1; 118(21):5210-6.; Liede A, Karlan B Y, Narod S A. Cancer risks for male carriers of germline mutations in BRCA1 or BRCA2: a review of the literature. J Clin Oncol. 2004 Feb. 15; 22(4):735-42.] The spectrum of these large rearrangement is quite extensive, and Sanger sequencing of PCR amplified DNA is typically used to characterized these rearrangements. Our gRNA/Cas9 probing strategy labels the full length of each BRCA gene locus at high density (approximately one probed site per 100 bp), using a specific color pattern along the locus (Table 3, Locational Code). For any regions rearranged within its locus, the color pattern will change, allowing the identification of these large rearrangements. Our approach provides a simpler alternative to sequencing. Our approach is also used to detect other similar rearrangements in other cancers, such as acute myeloid leukemia, developmental diseases, such as Bushy syndrome, and neurodevelopmental diseases, such as autism. Another category of rearrangement that is amenable to this approach include the VDJ recombination of immune cell receptors.

Example XI

FIG. 8 is directed to DNA Origami barcodes applied to specific locations targeted by gRNA/cas9 complex. Each barcode is unique to the location the gRNA is targeting. The BRCA1 and BRCA2 genes are susceptible the genomic rearrangements of varied magnitudes, including smaller insertions and deletions, which only Sanger sequencing can detect. Our gRNA/Cas9 probing strategy labels the full length of each BRCA gene locus at high density (approximately one probed site per 100 bp), using a barcode unique to each gRNA/Cas9 target site. This barcode takes the form of a fluorescent origami barcode as previously described [Lin C, Jungmann R, Leifer A M, Li C, Levner D, Church G M, Shih W M, Yin P. Submicrometre geometrically encoded fluorescent barcodes self-assembled from DNA. Nat Chem. 2012 October; 4(10):832-9.] By decoding each barcode (Table 3, Origami Code), we identify each gRNA/Cas9 and its location on the locus, which provides information about insertions, deletions and regions rearranged within its locus. This level of resolution can be taken into consideration by the clinician when deciding the proper cancer treatment. Our approach provides an alternative to sequencing. Our approach is also used to detect other similar rearrangements in other cancers, developmental diseases, and neurodevelopmental diseases. Another category of rearrangement that is amenable to this approach include the VDJ recombination of immune cell receptors.

Example XII

FIGS. 9A-9B are directed to polymerase extension from a gRNA/Cas9 nick. FIG. 9A depicts a top strand of the target DNA cleaved by gRNA and the D10A mutant of Cas9. FIG. 9B depicts the bottom strand of the target DNA cleaved by gRNA and the H840A mutant of Cas9. The curved arrow shows the direction of primer extension from the nicks. The primer extension can be used to label the targeted region or to initiate sequencing of the targeted region. Our gRNA/Cas9 nick and sequencing approach allows for the precise targeted localization of the sequencing start site on the genome. Briefly, gRNA/Cas9 nickase makes a nick in the DNA strand at a targeted location of interest. The gRNA/Cas9 is then displaced by one of several methods, such as detergent, denaturants, or temperature. A DNA polymerase with strand displacement activity, and labeled dNTP, are then added, thereby extending the DNA from the nick site. A large number of genomic regions of interest are amenable to this gRNA/Cas9 nick initiation method. Repeat regions, such as centromeric DNA are inherently hard to sequence and align due to their great number of short repeats. Genomic rearrangements often contain smaller mutations. Additionally, many genomic rearrangements are poorly characterized and the location of the rearrangement or fusion is not known.

Example XIII

FIG. 10 is a diagram of the output provided when using CHOPCHOP to find PAM sites. CHOCHOP is one of many online tool used algorithm to find and score gRNA/Cas9 targets and off-targets on a given locus [Tessa G. Montague; Jose M. Cruz; James A. Gagnon; George M. Church; Eivind Valen. (2014). CHOPCHOP: a CRISPR/Cas9 and TALEN web tool for genome editing. Nucleic Acids Res. 42. W401-W407]. This diagram represents the graphical output of a search for target on Her2 exons. The small triangles represent the gRNA/Cas9 target site on Her2 exon. The list of target sequences can be extracted, curated to keep only the target with no or with a low number of off-targets, and then used to design gRNAs. This tool is used to find gRNA/Cas9 targets for other locus. Other tools can be used for finding targets on both introns and exons, or outside the locus.

Example XIV

FIG. 11 is directed to assembly of a DNA template for in vitro transcription of guide RNA, using high fidelity Polymerase Chain Reaction (PCR). This strategy relies on 2 universal oligonucleotides: Fwd-T7-gRNA, a forward PCR primer which also include a portion of the T7 RNA polymerase recognition motif for in vitro transcription; and gRNA.split60 the gRNA scaffold. Additionally, there are 2 specific oligonucleotides: Sp.gRNA.split60, the sequence specific for the target of interest; and Rev-B1-gRNA.18, a reverse PCR primer which also include a barcoded handle for multiplex strand detection. The suggested melting temperature (Tm) is also provided. This design is cost efficient, minimizes amplification errors, and is amenable to small scale or large scale oligonucleotide. Once amplified, the DNA templates can be re-amplified by PCR to generate and perpetuate the templates, which is more cost effective than de novo synthesis. The PCR assembly takes less than an hour. Following PCR, gRNA are synthesized by in vitro transcription (IVT) by adding a T7 RNA polymerase mix to the template DNA.

Example XV

Figure 12:
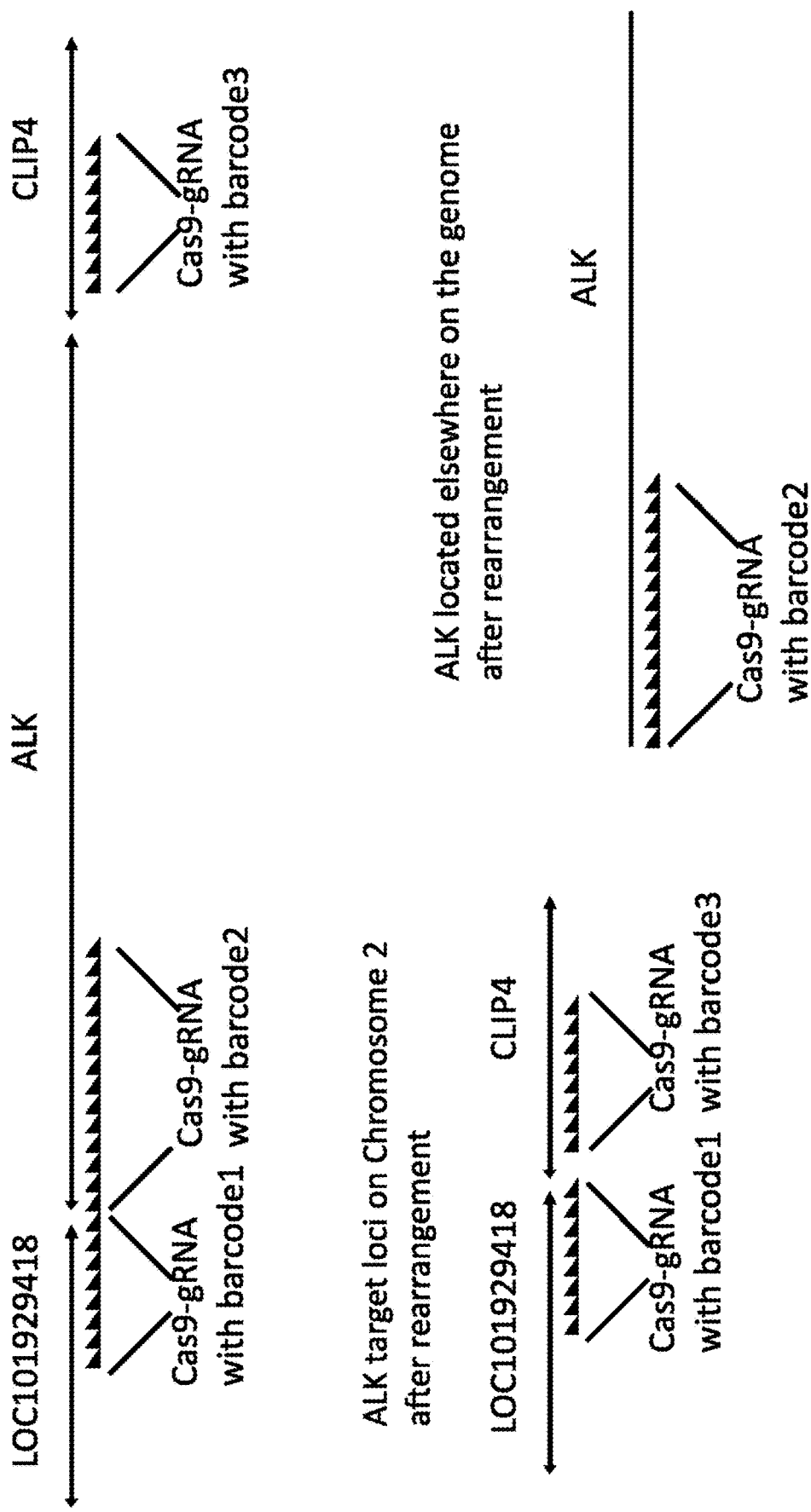
FIG. 12 presents a diagram for identifying genomic fusions using gRNA/Cas9 probing.

FIG. 12 is a schematic of Cas9-gRNA targeting of ALK translocations. The figure shows that when the two fused regions are known, the occurrence of the fusion can be detected by using gRNA/Cas9 bearing specific barcodes. The ALK locus is susceptible to both intra-chromosomal and inter-chromosomal rearrangements and inversions. There are 7 such rearrangements known with adverse clinical outcomes [Solomon B, Varella-Garcia M, Camidge D R. ALK gene rearrangements: a new therapeutic target in a molecularly defined subset of non-small cell lung cancer. J Thorac Oncol. 2009 December; 4(12):1450-4.]. Our gRNA/Cas9 probing strategy labels specific locus regions at high density (approximately one probed site per 100 bp), using a color associated to each locus. This strategy is useful to detect gene fusion and inversion. When the two labeled loci are adjacent, their respective labels are detected as co-localized signal. In case of a rearrangement, the two signals are not co-localized anymore, and are quite distant. In case of an inversion, the signals are not co-localized, but are still in the same vicinity. For added confidence, a third locus is labeled, which provides a different co-localization combination in case of gene fusion (due to ALK inter-chromosomal rearrangement), or in case of ALK inversion. Detection of such ALK defects is important in identifying several cancers, such as anaplastic large-cell lymphoma (ALK-NPM1 fusion), adenocarcinoma of the lung (ALK-EML4 fusion and inversion), and certain pediatric neuroblastoma. Treatments exist for certain ALK rearrangements. Several other diseases are characterized by gene fusions and are amenable to our approach. Some examples of gene fusion targets include ABL1-BCR, AML1-RUNX1T1, AML1-ETV6, BCL-2-IGH, BCL-2-MLT, C-Myc-IGH, COL1A1-PDGFB, CycD1-IGH, ETV6-TRKC, ETV6-JAK, FLI1-EWS, PAX8-PPARG, PML-NR1B1, TCR-RBTN2, SS18-SSX.

The invention claimed is:

1. A method of sequencing a target sequence of a target double-stranded nucleic acid comprising
   (a) contacting the target double-stranded nucleic acid with a guide RNA sequence having a portion complementary to the target sequence of the target double-stranded nucleic acid and a Cas9 protein,
   wherein the guide RNA and the Cas9 protein co-localize to the target sequence of the target double-stranded nucleic acid to form a complex, and
   wherein the Cas9 protein is a Cas9 nickase which nicks a strand of the target double-stranded nucleic acid and wherein primer extension is initiated from the nick to incorporate nucleotides to form a growing chain, with the complementary strand serving as a template; and
   (b) detecting the nucleotides incorporated into the growing chain, thereby sequencing the target sequence of the target double-stranded nucleic acid.

2. The method of claim 1 wherein the sequencing comprises detecting the incorporation of individual nucleotides into the growing chain.

3. The method of claim 2 where the nucleotides are fluorescently labeled.

4. The method of claim 2 wherein the nucleotides A, C, G, T are differentially labeled and are provided in solution during the incorporation of the nucleotides into the growing chain.

5. The method according to claim 2 wherein the nucleotides are reversible terminators and stepwise sequencing by synthesis is conducted.

6. The method of claim 2 where the nucleotides are labeled at a terminal phosphate and real-time sequencing is conducted.

7. The method of claim 1 wherein the target double-stranded nucleic acid is analyzed as a linear string.

8. The method of claim 1 wherein the target double-stranded nucleic acid is analyzed as a linear string that is substantially stretched out.

9. The method of claim 1 wherein primer extension from the nick is initiated from multiple sites on a target double-stranded nucleic acid linear string.

10. The method of claim 1 wherein a plurality of target sequences of a plurality of target double-stranded nucleic acids are sequenced in parallel.

11. The method of claim 1 wherein the target double-stranded nucleic acid is a genomic DNA molecule, and wherein one or more regions of the genomic DNA molecule are sequenced.

12. The method of claim 1 wherein the gRNA/Cas9 complex is removed after nicking.

13. The method of claim 1 wherein the target double-stranded nucleic acid is analysed in a cell in situ.

14. The method of claim 13 wherein the cell is fixed before analysis.

15. The method of claim 13 wherein RNA molecules within the cell are removed before analysis.

16. The method of claim 1 wherein the Cas9 nickase comprises an inactive RuvC-like domain.

17. The method of claim 1 wherein the Cas9 nickase comprises an inactive HNH domain.

18. The method of claim 1 wherein the Cas9 nickase is a D10A nicking mutant.

19. The method of claim 1 wherein the Cas9 nickase is an H840A nicking mutant.

* * * * *

SEQUENCE LISTING

<160> NUMBER OF SEQ ID NOS: 146

<210> SEQ ID NO 1
<211> LENGTH: 16
<212> TYPE: DNA
<213> ORGANISM: Artificial
<220> FEATURE:
<223> OTHER INFORMATION: initiating sequence
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (12)..(16)
<223> OTHER INFORMATION: n is a, c, g, or t

<400> SEQUENCE: 1
nnnnnnnnng gnnnnn                                                       16

<210> SEQ ID NO 2
<211> LENGTH: 16
<212> TYPE: DNA
<213> ORGANISM: Artificial
<220> FEATURE:
<223> OTHER INFORMATION: initiating sequence
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (12)..(16)
<223> OTHER INFORMATION: n is a, c, g, or t

<400> SEQUENCE: 2
nnnnnnnnnc cnnnnn                                                       16

<210> SEQ ID NO 3
<211> LENGTH: 24
<212> TYPE: DNA
<213> ORGANISM: Artificial
<220> FEATURE:
<223> OTHER INFORMATION: guide RNA

<400> SEQUENCE: 3
gaaattaata cgactcacta tagg                                              24

<210> SEQ ID NO 4
<211> LENGTH: 60
<212> TYPE: DNA
<213> ORGANISM: Artificial
<220> FEATURE:
<223> OTHER INFORMATION: guide RNA
<220> FEATURE:
<221> NAME/KEY: misc_feature
<222> LOCATION: (21)..(38)
<223> OTHER INFORMATION: n is a, c, g, or t

<400> SEQUENCE: 4
ttaatacgac tcactatagg nnnnnnnnnn nnnnnnnngt tttagagcta gaaatagcaa        60

<210> SEQ ID NO 5
<211> LENGTH: 81
<212> TYPE: DNA
<213> ORGANISM: Artificial
<220> FEATURE:
<223> OTHER INFORMATION: guide RNA

<400> SEQUENCE: 5

-continued

```
gttttagagc tagaaatagc aagttaaaat aaggctagtc cgttatcaac ttgaaaaagt    60
ggcaccgagt cggtgctttt t                                              81
```

<210> SEQ ID NO 6
<211> LENGTH: 28
<212> TYPE: DNA
<213> ORGANISM: Artificial
<220> FEATURE:
<223> OTHER INFORMATION: guide RNA

<400> SEQUENCE: 6

```
accgagtcgg tgctttttta tacatcta                                       28
```

<210> SEQ ID NO 7
<211> LENGTH: 1368
<212> TYPE: PRT
<213> ORGANISM: Streptococcus pyogenes

<400> SEQUENCE: 7

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285
```

```
Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
```

```
            705                 710                 715                 720
His Glu His Ile Ala Asn Leu Ala Gly Ser Pro Ala Ile Lys Lys Gly
                    725                 730                 735
Ile Leu Gln Thr Val Lys Val Val Asp Glu Leu Val Lys Val Met Gly
                    740                 745                 750
Arg His Lys Pro Glu Asn Ile Val Ile Glu Met Ala Arg Glu Asn Gln
                    755                 760                 765
Thr Thr Gln Lys Gly Gln Lys Asn Ser Arg Glu Arg Met Lys Arg Ile
            770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                    805                 810                 815
Gln Asn Gly Arg Asp Met Tyr Val Asp Gln Glu Leu Asp Ile Asn Arg
                    820                 825                 830
Leu Ser Asp Tyr Asp Val Asp His Ile Val Pro Gln Ser Phe Leu Lys
                    835                 840                 845
Asp Asp Ser Ile Asp Asn Lys Val Leu Thr Arg Ser Asp Lys Asn Arg
850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                    885                 890                 895
Phe Asp Asn Leu Thr Lys Ala Glu Arg Gly Gly Leu Ser Glu Leu Asp
                    900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
            930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                    965                 970                 975
Glu Ile Asn Asn Tyr His His Ala His Asp Ala Tyr Leu Asn Ala Val
                    980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
```

Lys Lys Tyr Gly Gly Phe Asp Ser Pro Thr Val Ala Tyr Ser Val
1130                1135                1140

Leu Val Val Ala Lys Val Glu Lys Gly Lys Ser Lys Lys Leu Lys
     1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
     1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
     1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
     1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
     1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
     1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
     1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
     1355                1360                1365

<210> SEQ ID NO 8
<211> LENGTH: 130
<212> TYPE: DNA
<213> ORGANISM: Artificial
<220> FEATURE:
<223> OTHER INFORMATION: Guide RNA

<400> SEQUENCE: 8
gacgccuucg uuggaaacgu uuagagcua gaaauagcaa guuaaaauaa ggcuaguccg      60
uuaucaacuu gaaaaagugg caccgagucg gugcuuuuut cctctaccac ctacatcact   120
tatacatcta                                                          130

<210> SEQ ID NO 9
<211> LENGTH: 31
<212> TYPE: DNA
<213> ORGANISM: Artificial
<220> FEATURE:
<223> OTHER INFORMATION: DNA probe

<400> SEQUENCE: 9
tagatgtata agtgatgtag gtggtagagg a                                   31

<210> SEQ ID NO 10

```
<211> LENGTH: 27
<212> TYPE: DNA
<213> ORGANISM: Artificial
<220> FEATURE:
<223> OTHER INFORMATION: DNA Paint imager probe

<400> SEQUENCE: 10
tagatgtata aaaaaattta ataaggt                                          27

<210> SEQ ID NO 11
<211> LENGTH: 16
<212> TYPE: DNA
<213> ORGANISM: Artificial
<220> FEATURE:
<223> OTHER INFORMATION: DNA PAINT imager probe

<400> SEQUENCE: 11
tagatgtata aaaaaa                                                      16

<210> SEQ ID NO 12
<211> LENGTH: 22
<212> TYPE: DNA
<213> ORGANISM: Artificial
<220> FEATURE:
<223> OTHER INFORMATION: PAM motif
<220> FEATURE:
<221> NAME/KEY: misc_feature
<222> LOCATION: (3)..(20)
<223> OTHER INFORMATION: n is a, c, g, or t

<400> SEQUENCE: 12
ggnnnnnnnn nnnnnnnnnn gg                                               22

<210> SEQ ID NO 13
<211> LENGTH: 23
<212> TYPE: DNA
<213> ORGANISM: Artificial
<220> FEATURE:
<223> OTHER INFORMATION: Target sequence for Her2

<400> SEQUENCE: 13
gggcgaggag gagcccccag cgg                                              23

<210> SEQ ID NO 14
<211> LENGTH: 23
<212> TYPE: DNA
<213> ORGANISM: Artificial
<220> FEATURE:
<223> OTHER INFORMATION: Her2 target sequence

<400> SEQUENCE: 14
ggtggcggag catgtccagg tgg                                              23

<210> SEQ ID NO 15
<211> LENGTH: 23
<212> TYPE: DNA
<213> ORGANISM: Artificial
<220> FEATURE:
<223> OTHER INFORMATION: Her2 target sequence

<400> SEQUENCE: 15
ggtgggtctc gggactggca ggg                                              23

<210> SEQ ID NO 16
<211> LENGTH: 23
<212> TYPE: DNA
<213> ORGANISM: Artificial
```

```
<220> FEATURE:
<223> OTHER INFORMATION: Her2 target squence

<400> SEQUENCE: 16
ggcagccctg gtagaggtgg cgg                                           23

<210> SEQ ID NO 17
<211> LENGTH: 23
<212> TYPE: DNA
<213> ORGANISM: Artificial
<220> FEATURE:
<223> OTHER INFORMATION: Her2 target sequence

<400> SEQUENCE: 17
ggaggcccct gtgacagggg tgg                                           23

<210> SEQ ID NO 18
<211> LENGTH: 23
<212> TYPE: DNA
<213> ORGANISM: Artificial
<220> FEATURE:
<223> OTHER INFORMATION: Her2 target sequence

<400> SEQUENCE: 18
gggcctcccc aggaggcctg cgg                                           23

<210> SEQ ID NO 19
<211> LENGTH: 23
<212> TYPE: DNA
<213> ORGANISM: Artificial
<220> FEATURE:
<223> OTHER INFORMATION: Her2 target sequence

<400> SEQUENCE: 19
ggcctcccca ggaggcctgc ggg                                           23

<210> SEQ ID NO 20
<211> LENGTH: 23
<212> TYPE: DNA
<213> ORGANISM: Artificial
<220> FEATURE:
<223> OTHER INFORMATION: Her2 target sequence

<400> SEQUENCE: 20
ggtggctgtg cccgctgcaa ggg                                           23

<210> SEQ ID NO 21
<211> LENGTH: 23
<212> TYPE: DNA
<213> ORGANISM: Artificial
<220> FEATURE:
<223> OTHER INFORMATION: Her2 target sequence

<400> SEQUENCE: 21
gggcagtggc cccttgcagc ggg                                           23

<210> SEQ ID NO 22
<211> LENGTH: 23
<212> TYPE: DNA
<213> ORGANISM: Artificial
<220> FEATURE:
<223> OTHER INFORMATION: Her2 target sequence

<400> SEQUENCE: 22
gggacaggca gtcacacagc tgg                                           23
```

<210> SEQ ID NO 23
<211> LENGTH: 23
<212> TYPE: DNA
<213> ORGANISM: Artificial
<220> FEATURE:
<223> OTHER INFORMATION: Her2 target sequence

<400> SEQUENCE: 23
ggttgtgcag ggggcagacg agg                                              23

<210> SEQ ID NO 24
<211> LENGTH: 23
<212> TYPE: DNA
<213> ORGANISM: Artificial
<220> FEATURE:
<223> OTHER INFORMATION: Her2 target sequence

<400> SEQUENCE: 24
gggcatggag cacttgcgag agg                                              23

<210> SEQ ID NO 25
<211> LENGTH: 23
<212> TYPE: DNA
<213> ORGANISM: Artificial
<220> FEATURE:
<223> OTHER INFORMATION: Her2 target sequence

<400> SEQUENCE: 25
ggagcacttg cgagaggtga ggg                                              23

<210> SEQ ID NO 26
<211> LENGTH: 23
<212> TYPE: DNA
<213> ORGANISM: Artificial
<220> FEATURE:
<223> OTHER INFORMATION: Her2 target sequence

<400> SEQUENCE: 26
ggagctgctc tggctggagc ggg                                              23

<210> SEQ ID NO 27
<211> LENGTH: 23
<212> TYPE: DNA
<213> ORGANISM: Artificial
<220> FEATURE:
<223> OTHER INFORMATION: Her2 target sequence

<400> SEQUENCE: 27
ggaagacgct gaggtcaggc agg                                              23

<210> SEQ ID NO 28
<211> LENGTH: 23
<212> TYPE: DNA
<213> ORGANISM: Artificial
<220> FEATURE:
<223> OTHER INFORMATION: Her2 target sequence

<400> SEQUENCE: 28
ggtgggtgtt atggtggatg agg                                              23

<210> SEQ ID NO 29
<211> LENGTH: 23
<212> TYPE: DNA
<213> ORGANISM: Artificial
<220> FEATURE:
<223> OTHER INFORMATION: Her2 target sequence

```
<400> SEQUENCE: 29
ggctggggct gcgctcactg agg                                              23

<210> SEQ ID NO 30
<211> LENGTH: 23
<212> TYPE: DNA
<213> ORGANISM: Artificial
<220> FEATURE:
<223> OTHER INFORMATION: Her2 target sequence

<400> SEQUENCE: 30
ggtgcgggtt ccgaaagagc tgg                                              23

<210> SEQ ID NO 31
<211> LENGTH: 23
<212> TYPE: DNA
<213> ORGANISM: Artificial
<220> FEATURE:
<223> OTHER INFORMATION: Her2 target sequence

<400> SEQUENCE: 31
ggctgggcat cagctggctg ggg                                              23

<210> SEQ ID NO 32
<211> LENGTH: 23
<212> TYPE: DNA
<213> ORGANISM: Artificial
<220> FEATURE:
<223> OTHER INFORMATION: Her2 target sequence

<400> SEQUENCE: 32
gggctgggca tcagctggct ggg                                              23

<210> SEQ ID NO 33
<211> LENGTH: 23
<212> TYPE: DNA
<213> ORGANISM: Artificial
<220> FEATURE:
<223> OTHER INFORMATION: Her2 target sequence

<400> SEQUENCE: 33
ggaggaatgc cgagtactgc agg                                              23

<210> SEQ ID NO 34
<211> LENGTH: 23
<212> TYPE: DNA
<213> ORGANISM: Artificial
<220> FEATURE:
<223> OTHER INFORMATION: Her2 target sequence

<400> SEQUENCE: 34
ggcattcctc cacgcactcc tgg                                              23

<210> SEQ ID NO 35
<211> LENGTH: 23
<212> TYPE: DNA
<213> ORGANISM: Artificial
<220> FEATURE:
<223> OTHER INFORMATION: Her2 target sequence

<400> SEQUENCE: 35
ggctgacact cagggtggca cgg                                              23

<210> SEQ ID NO 36
```

```
<211> LENGTH: 23
<212> TYPE: DNA
<213> ORGANISM: Artificial
<220> FEATURE:
<223> OTHER INFORMATION: Her2 target sequence

<400> SEQUENCE: 36
ggtcaggttt cacaccgctg ggg                                              23

<210> SEQ ID NO 37
<211> LENGTH: 23
<212> TYPE: DNA
<213> ORGANISM: Artificial
<220> FEATURE:
<223> OTHER INFORMATION: Her2 target sequence

<400> SEQUENCE: 37
gggcagcggg ccacgcagaa ggg                                              23

<210> SEQ ID NO 38
<211> LENGTH: 23
<212> TYPE: DNA
<213> ORGANISM: Artificial
<220> FEATURE:
<223> OTHER INFORMATION: Her2 target sequence

<400> SEQUENCE: 38
ggggcagcgg gccacgcaga agg                                              23

<210> SEQ ID NO 39
<211> LENGTH: 23
<212> TYPE: DNA
<213> ORGANISM: Artificial
<220> FEATURE:
<223> OTHER INFORMATION: Her2 target sequence

<400> SEQUENCE: 39
ggttggcatt ctgctggtcg tgg                                              23

<210> SEQ ID NO 40
<211> LENGTH: 23
<212> TYPE: DNA
<213> ORGANISM: Artificial
<220> FEATURE:
<223> OTHER INFORMATION: Her2 target sequence

<400> SEQUENCE: 40
ggagaatgtg aaaattccag tgg                                              23

<210> SEQ ID NO 41
<211> LENGTH: 23
<212> TYPE: DNA
<213> ORGANISM: Artificial
<220> FEATURE:
<223> OTHER INFORMATION: Her2 target sequence

<400> SEQUENCE: 41
gggcatctgc ctgacatcca cgg                                              23

<210> SEQ ID NO 42
<211> LENGTH: 23
<212> TYPE: DNA
<213> ORGANISM: Artificial
<220> FEATURE:
<223> OTHER INFORMATION: Her2 target sequence

<400> SEQUENCE: 42
```
ggatgtgcgg ctcgtacaca ggg                                                   23

<210> SEQ ID NO 43
<211> LENGTH: 23
<212> TYPE: DNA
<213> ORGANISM: Artificial
<220> FEATURE:
<223> OTHER INFORMATION: Her2 target sequence

<400> SEQUENCE: 43
ggtgaaccgc cggcggagaa tgg                                                   23

<210> SEQ ID NO 44
<211> LENGTH: 23
<212> TYPE: DNA
<213> ORGANISM: Artificial
<220> FEATURE:
<223> OTHER INFORMATION: Her2 target sequence

<400> SEQUENCE: 44
ggtcagggat ctcccgggct ggg                                                   23

<210> SEQ ID NO 45
<211> LENGTH: 23
<212> TYPE: DNA
<213> ORGANISM: Artificial
<220> FEATURE:
<223> OTHER INFORMATION: Her2 target sequence

<400> SEQUENCE: 45
ggatgaccac aaagcgctgg ggg                                                   23

<210> SEQ ID NO 46
<211> LENGTH: 23
<212> TYPE: DNA
<213> ORGANISM: Artificial
<220> FEATURE:
<223> OTHER INFORMATION: Her2 target sequence

<400> SEQUENCE: 46
ggatgattga ctctgaatgt cgg                                                   23

<210> SEQ ID NO 47
<211> LENGTH: 23
<212> TYPE: DNA
<213> ORGANISM: Artificial
<220> FEATURE:
<223> OTHER INFORMATION: Her2 target sequence

<400> SEQUENCE: 47
ggtgtctgaa ttctcccgca tgg                                                   23

<210> SEQ ID NO 48
<211> LENGTH: 23
<212> TYPE: DNA
<213> ORGANISM: Artificial
<220> FEATURE:
<223> OTHER INFORMATION: Her2 target sequence

<400> SEQUENCE: 48
ggacagaaga agccctgctg ggg                                                   23

<210> SEQ ID NO 49
<211> LENGTH: 23
<212> TYPE: DNA

```
<213> ORGANISM: Artificial
<220> FEATURE:
<223> OTHER INFORMATION: Her2 target sequence

<400> SEQUENCE: 49
gggggacctg gtggatgctg agg                                           23

<210> SEQ ID NO 50
<211> LENGTH: 23
<212> TYPE: DNA
<213> ORGANISM: Artificial
<220> FEATURE:
<223> OTHER INFORMATION: Her2 target sequence

<400> SEQUENCE: 50
ggacgatgac atgggggacc tgg                                           23

<210> SEQ ID NO 51
<211> LENGTH: 23
<212> TYPE: DNA
<213> ORGANISM: Artificial
<220> FEATURE:
<223> OTHER INFORMATION: Her2 target sequence

<400> SEQUENCE: 51
ggtggatgct gaggagtatc tgg                                           23

<210> SEQ ID NO 52
<211> LENGTH: 23
<212> TYPE: DNA
<213> ORGANISM: Artificial
<220> FEATURE:
<223> OTHER INFORMATION: Her2 target sequence

<400> SEQUENCE: 52
ggcaccgcag ctcatctacc agg                                           23

<210> SEQ ID NO 53
<211> LENGTH: 23
<212> TYPE: DNA
<213> ORGANISM: Artificial
<220> FEATURE:
<223> OTHER INFORMATION: Her2 target sequence

<400> SEQUENCE: 53
ggagtatctg gtaccccagc agg                                           23

<210> SEQ ID NO 54
<211> LENGTH: 23
<212> TYPE: DNA
<213> ORGANISM: Artificial
<220> FEATURE:
<223> OTHER INFORMATION: Her2 target sequence

<400> SEQUENCE: 54
ggaccatgcc cccagcgccc ggg                                           23

<210> SEQ ID NO 55
<211> LENGTH: 23
<212> TYPE: DNA
<213> ORGANISM: Artificial
<220> FEATURE:
<223> OTHER INFORMATION: Her2 target sequence

<400> SEQUENCE: 55
gggtgccagt ggagacctgg ggg                                           23
```

<210> SEQ ID NO 56
<211> LENGTH: 23
<212> TYPE: DNA
<213> ORGANISM: Artificial
<220> FEATURE:
<223> OTHER INFORMATION: Her2 target sequence

<400> SEQUENCE: 56
ggcggtgggg acctgacact agg                                          23

<210> SEQ ID NO 57
<211> LENGTH: 23
<212> TYPE: DNA
<213> ORGANISM: Artificial
<220> FEATURE:
<223> OTHER INFORMATION: Her2 target sequence

<400> SEQUENCE: 57
ggggaggctt tgcagcccct tgg                                          23

<210> SEQ ID NO 58
<211> LENGTH: 23
<212> TYPE: DNA
<213> ORGANISM: Artificial
<220> FEATURE:
<223> OTHER INFORMATION: Her2 target sequence

<400> SEQUENCE: 58
ggtcctggtc ccagtaatag agg                                          23

<210> SEQ ID NO 59
<211> LENGTH: 23
<212> TYPE: DNA
<213> ORGANISM: Artificial
<220> FEATURE:
<223> OTHER INFORMATION: Her2 target sequence

<400> SEQUENCE: 59
gggaccagga cccaccagag cgg                                          23

<210> SEQ ID NO 60
<211> LENGTH: 23
<212> TYPE: DNA
<213> ORGANISM: Artificial
<220> FEATURE:
<223> OTHER INFORMATION: Her2 target sequence

<400> SEQUENCE: 60
ggtgtccctt tgaaggtgct ggg                                          23

<210> SEQ ID NO 61
<211> LENGTH: 23
<212> TYPE: DNA
<213> ORGANISM: Artificial
<220> FEATURE:
<223> OTHER INFORMATION: Her2 target sequence

<400> SEQUENCE: 61
gggggctggg gccgaacatc tgg                                          23

<210> SEQ ID NO 62
<211> LENGTH: 23
<212> TYPE: DNA
<213> ORGANISM: Artificial
<220> FEATURE:

<223> OTHER INFORMATION: Her2 target sequence

<400> SEQUENCE: 62
ggcccaagac tctctcccca ggg                                              23

<210> SEQ ID NO 63
<211> LENGTH: 12
<212> TYPE: DNA
<213> ORGANISM: Artificial
<220> FEATURE:
<223> OTHER INFORMATION: barcode B1

<400> SEQUENCE: 63
cgtcgattac ca                                                          12

<210> SEQ ID NO 64
<211> LENGTH: 12
<212> TYPE: DNA
<213> ORGANISM: Artificial
<220> FEATURE:
<223> OTHER INFORMATION: barcode B2

<400> SEQUENCE: 64
ccatactcgt cg                                                          12

<210> SEQ ID NO 65
<211> LENGTH: 12
<212> TYPE: DNA
<213> ORGANISM: Artificial
<220> FEATURE:
<223> OTHER INFORMATION: barcode B3

<400> SEQUENCE: 65
tcgatagtac gt                                                          12

<210> SEQ ID NO 66
<211> LENGTH: 12
<212> TYPE: DNA
<213> ORGANISM: Artificial
<220> FEATURE:
<223> OTHER INFORMATION: barcode B4

<400> SEQUENCE: 66
cgtactgaac ga                                                          12

<210> SEQ ID NO 67
<211> LENGTH: 12
<212> TYPE: DNA
<213> ORGANISM: Artificial
<220> FEATURE:
<223> OTHER INFORMATION: barcode B5

<400> SEQUENCE: 67
cgaagtacta cg                                                          12

<210> SEQ ID NO 68
<211> LENGTH: 12
<212> TYPE: DNA
<213> ORGANISM: Artificial
<220> FEATURE:
<223> OTHER INFORMATION: barcode B6

<400> SEQUENCE: 68
tcgttacgac ca                                                          12

```
<210> SEQ ID NO 69
<211> LENGTH: 12
<212> TYPE: DNA
<213> ORGANISM: Artificial
<220> FEATURE:
<223> OTHER INFORMATION: barcode B7

<400> SEQUENCE: 69
ccagacgaat cg                                                           12

<210> SEQ ID NO 70
<211> LENGTH: 12
<212> TYPE: DNA
<213> ORGANISM: Artificial
<220> FEATURE:
<223> OTHER INFORMATION: barcode B8

<400> SEQUENCE: 70
tcgaatagtc gt                                                           12

<210> SEQ ID NO 71
<211> LENGTH: 12
<212> TYPE: DNA
<213> ORGANISM: Artificial
<220> FEATURE:
<223> OTHER INFORMATION: barcode B9

<400> SEQUENCE: 71
cgtaactaac ga                                                           12

<210> SEQ ID NO 72
<211> LENGTH: 12
<212> TYPE: DNA
<213> ORGANISM: Artificial
<220> FEATURE:
<223> OTHER INFORMATION: barcode B10

<400> SEQUENCE: 72
cgaacaatcg ta                                                           12

<210> SEQ ID NO 73
<211> LENGTH: 23
<212> TYPE: DNA
<213> ORGANISM: Artificial
<220> FEATURE:
<223> OTHER INFORMATION: CEN17.1 target

<400> SEQUENCE: 73
gagcgctttc aggcctgtgg tgg                                               23

<210> SEQ ID NO 74
<211> LENGTH: 23
<212> TYPE: DNA
<213> ORGANISM: Artificial
<220> FEATURE:
<223> OTHER INFORMATION: CEN17.2 target

<400> SEQUENCE: 74
gagggctttg aggcctgtgg tgg                                               23

<210> SEQ ID NO 75
<211> LENGTH: 23
<212> TYPE: DNA
<213> ORGANISM: Artificial
<220> FEATURE:
<223> OTHER INFORMATION: target sequence
```

<400> SEQUENCE: 75
gagggctttg tggtttgtgg tgg                                           23

<210> SEQ ID NO 76
<211> LENGTH: 23
<212> TYPE: DNA
<213> ORGANISM: Artificial
<220> FEATURE:
<223> OTHER INFORMATION: target sequence

<400> SEQUENCE: 76
ggaatctgca agtggatatg tgg                                           23

<210> SEQ ID NO 77
<211> LENGTH: 23
<212> TYPE: DNA
<213> ORGANISM: Artificial
<220> FEATURE:
<223> OTHER INFORMATION: target sequence

<400> SEQUENCE: 77
gtgttgaaac tctcttttg tgg                                            23

<210> SEQ ID NO 78
<211> LENGTH: 23
<212> TYPE: DNA
<213> ORGANISM: Artificial
<220> FEATURE:
<223> OTHER INFORMATION: target sequence

<400> SEQUENCE: 78
gtttccaatc actctttgtg tgg                                           23

<210> SEQ ID NO 79
<211> LENGTH: 23
<212> TYPE: DNA
<213> ORGANISM: Artificial
<220> FEATURE:
<223> OTHER INFORMATION: target sequence

<400> SEQUENCE: 79
gtttggaaac actcttgttg tgg                                           23

<210> SEQ ID NO 80
<211> LENGTH: 23
<212> TYPE: DNA
<213> ORGANISM: Artificial
<220> FEATURE:
<223> OTHER INFORMATION: target sequence

<400> SEQUENCE: 80
gttttgaaac tctctttctg tgg                                           23

<210> SEQ ID NO 81
<211> LENGTH: 22
<212> TYPE: DNA
<213> ORGANISM: Artificial
<220> FEATURE:
<223> OTHER INFORMATION: target sequence

<400> SEQUENCE: 81
acactgctct atccatagga gg                                            22

<210> SEQ ID NO 82
<211> LENGTH: 22

```
<212> TYPE: DNA
<213> ORGANISM: Artificial
<220> FEATURE:
<223> OTHER INFORMATION: target sequence

<400> SEQUENCE: 82
agatatttgg accgctctga gg                                              22

<210> SEQ ID NO 83
<211> LENGTH: 22
<212> TYPE: DNA
<213> ORGANISM: Artificial
<220> FEATURE:
<223> OTHER INFORMATION: target sequence

<400> SEQUENCE: 83
agcgctttca ggcctgtggt gg                                              22

<210> SEQ ID NO 84
<211> LENGTH: 22
<212> TYPE: DNA
<213> ORGANISM: ARTIFICIAL
<220> FEATURE:
<223> OTHER INFORMATION: target sequence

<400> SEQUENCE: 84
aggaatgttc aactctgtga gg                                              22

<210> SEQ ID NO 85
<211> LENGTH: 22
<212> TYPE: DNA
<213> ORGANISM: ARTIFICIAL
<220> FEATURE:
<223> OTHER INFORMATION: target sequence

<400> SEQUENCE: 85
agggctttga ggcctgtggt gg                                              22

<210> SEQ ID NO 86
<211> LENGTH: 22
<212> TYPE: DNA
<213> ORGANISM: ARTIFICIAL
<220> FEATURE:
<223> OTHER INFORMATION: target sequence

<400> SEQUENCE: 86
agggctttgt ggtttgtggt gg                                              22

<210> SEQ ID NO 87
<211> LENGTH: 22
<212> TYPE: DNA
<213> ORGANISM: ARTIFICIAL
<220> FEATURE:
<223> OTHER INFORMATION: target sequence

<400> SEQUENCE: 87
catcacagag aagcttctga gg                                              22

<210> SEQ ID NO 88
<211> LENGTH: 22
<212> TYPE: DNA
<213> ORGANISM: ARTIFICIAL
<220> FEATURE:
<223> OTHER INFORMATION: target sequence

<400> SEQUENCE: 88
```
ctgcattcaa ctcacagtgt gg                                              22

<210> SEQ ID NO 89
<211> LENGTH: 22
<212> TYPE: DNA
<213> ORGANISM: ARTIFICIAL
<220> FEATURE:
<223> OTHER INFORMATION: target sequence

<400> SEQUENCE: 89
gaaaggaaag ttcaactcgg gg                                              22

<210> SEQ ID NO 90
<211> LENGTH: 22
<212> TYPE: DNA
<213> ORGANISM: ARTIFICIAL
<220> FEATURE:
<223> OTHER INFORMATION: target sequence

<400> SEQUENCE: 90
gaatctgcaa gtggatatgt gg                                              22

<210> SEQ ID NO 91
<211> LENGTH: 22
<212> TYPE: DNA
<213> ORGANISM: ARTIFICIAL
<220> FEATURE:
<223> OTHER INFORMATION: target sequence

<400> SEQUENCE: 91
gaatgcaaac atcacgaaga gg                                              22

<210> SEQ ID NO 92
<211> LENGTH: 22
<212> TYPE: DNA
<213> ORGANISM: ARTIFICIAL
<220> FEATURE:
<223> OTHER INFORMATION: target sequence

<400> SEQUENCE: 92
gcatatttgg acctctttga gg                                              22

<210> SEQ ID NO 93
<211> LENGTH: 22
<212> TYPE: DNA
<213> ORGANISM: ARTIFICIAL
<220> FEATURE:
<223> OTHER INFORMATION: target sequence

<400> SEQUENCE: 93
gcttctgttt agttctgtgc gg                                              22

<210> SEQ ID NO 94
<211> LENGTH: 22
<212> TYPE: DNA
<213> ORGANISM: ARTIFICIAL
<220> FEATURE:
<223> OTHER INFORMATION: target sequence

<400> SEQUENCE: 94
gcttctgttt agttctgtgc gg                                              22

<210> SEQ ID NO 95
<211> LENGTH: 22
<212> TYPE: DNA
<213> ORGANISM: ARTIFICIAL

```
<220> FEATURE:
<223> OTHER INFORMATION: target sequence

<400> SEQUENCE: 95
ggacatttgg agggctttga gg                                              22

<210> SEQ ID NO 96
<211> LENGTH: 22
<212> TYPE: DNA
<213> ORGANISM: ARTIFICIAL
<220> FEATURE:
<223> OTHER INFORMATION: target sequence

<400> SEQUENCE: 96
ggacgtttgg agggctttgt gg                                              22

<210> SEQ ID NO 97
<211> LENGTH: 22
<212> TYPE: DNA
<213> ORGANISM: ARTIFICIAL
<220> FEATURE:
<223> OTHER INFORMATION: target sequence

<400> SEQUENCE: 97
ggagatttgg agcgctttga gg                                              22

<210> SEQ ID NO 98
<211> LENGTH: 22
<212> TYPE: DNA
<213> ORGANISM: ARTIFICIAL
<220> FEATURE:
<223> OTHER INFORMATION: target sequence

<400> SEQUENCE: 98
ggatatttag gcctctctga gg                                              22

<210> SEQ ID NO 99
<211> LENGTH: 22
<212> TYPE: DNA
<213> ORGANISM: ARTIFICIAL
<220> FEATURE:
<223> OTHER INFORMATION: target sequence

<400> SEQUENCE: 99
ggatatttgg accactctgt gg                                              22

<210> SEQ ID NO 100
<211> LENGTH: 22
<212> TYPE: DNA
<213> ORGANISM: ARTIFICIAL
<220> FEATURE:
<223> OTHER INFORMATION: target sequence

<400> SEQUENCE: 100
ggatatttgg acctctctga gg                                              22

<210> SEQ ID NO 101
<211> LENGTH: 22
<212> TYPE: DNA
<213> ORGANISM: ARTIFICIAL
<220> FEATURE:
<223> OTHER INFORMATION: target sequence

<400> SEQUENCE: 101
gggatcattg cactctttga gg                                              22
```

<210> SEQ ID NO 102
<211> LENGTH: 22
<212> TYPE: DNA
<213> ORGANISM: ARTIFICIAL
<220> FEATURE:
<223> OTHER INFORMATION: target sequence

<400> SEQUENCE: 102
tactaccata ggcctaaagc gg                                    22

<210> SEQ ID NO 103
<211> LENGTH: 22
<212> TYPE: DNA
<213> ORGANISM: ARTIFICIAL
<220> FEATURE:
<223> OTHER INFORMATION: target sequence

<400> SEQUENCE: 103
tatttgtaga atgtgcaagt gg                                    22

<210> SEQ ID NO 104
<211> LENGTH: 22
<212> TYPE: DNA
<213> ORGANISM: ARTIFICIAL
<220> FEATURE:
<223> OTHER INFORMATION: target sequence

<400> SEQUENCE: 104
tccaaagaca tcttcggaga gg                                    22

<210> SEQ ID NO 105
<211> LENGTH: 22
<212> TYPE: DNA
<213> ORGANISM: ARTIFICIAL
<220> FEATURE:
<223> OTHER INFORMATION: target sequence

<400> SEQUENCE: 105
tccaacgaaa tcctcagaga gg                                    22

<210> SEQ ID NO 106
<211> LENGTH: 22
<212> TYPE: DNA
<213> ORGANISM: ARTIFICIAL
<220> FEATURE:
<223> OTHER INFORMATION: target sequence

<400> SEQUENCE: 106
tccaacgaaa tcctcagaga gg                                    22

<210> SEQ ID NO 107
<211> LENGTH: 22
<212> TYPE: DNA
<213> ORGANISM: ARTIFICIAL
<220> FEATURE:
<223> OTHER INFORMATION: target sequence

<400> SEQUENCE: 107
tccaacgaaa tcctcagagc gg                                    22

<210> SEQ ID NO 108
<211> LENGTH: 22
<212> TYPE: DNA
<213> ORGANISM: ARTIFICIAL
<220> FEATURE:
<223> OTHER INFORMATION: target sequence

```
<400> SEQUENCE: 108
tccaacgaaa tcttcaaaga gg                                            22

<210> SEQ ID NO 109
<211> LENGTH: 22
<212> TYPE: DNA
<213> ORGANISM: ARTIFICIAL
<220> FEATURE:
<223> OTHER INFORMATION: target sequence

<400> SEQUENCE: 109
tccaacgaaa tgctcagaga gg                                            22

<210> SEQ ID NO 110
<211> LENGTH: 22
<212> TYPE: DNA
<213> ORGANISM: ARTIFICIAL
<220> FEATURE:
<223> OTHER INFORMATION: target sequence

<400> SEQUENCE: 110
tcgaacgaag gacacagagt gg                                            22

<210> SEQ ID NO 111
<211> LENGTH: 22
<212> TYPE: DNA
<213> ORGANISM: ARTIFICIAL
<220> FEATURE:
<223> OTHER INFORMATION: target sequence

<400> SEQUENCE: 111
tcgaacgaag gccacagagt gg                                            22

<210> SEQ ID NO 112
<211> LENGTH: 22
<212> TYPE: DNA
<213> ORGANISM: ARTIFICIAL
<220> FEATURE:
<223> OTHER INFORMATION: target sequence

<400> SEQUENCE: 112
tctgcaagtg gacatttgga gg                                            22

<210> SEQ ID NO 113
<211> LENGTH: 22
<212> TYPE: DNA
<213> ORGANISM: ARTIFICIAL
<220> FEATURE:
<223> OTHER INFORMATION: target sequence

<400> SEQUENCE: 113
tctgcaagtg gacgtttgga gg                                            22

<210> SEQ ID NO 114
<211> LENGTH: 22
<212> TYPE: DNA
<213> ORGANISM: ARTIFICIAL
<220> FEATURE:
<223> OTHER INFORMATION: target sequence

<400> SEQUENCE: 114
tggagcgctt tcaggcctgt gg                                            22

<210> SEQ ID NO 115
```

```
<211> LENGTH: 22
<212> TYPE: DNA
<213> ORGANISM: ARTIFICIAL
<220> FEATURE:
<223> OTHER INFORMATION: target sequence

<400> SEQUENCE: 115
tggagggctt tgaggcctgt gg                                                   22

<210> SEQ ID NO 116
<211> LENGTH: 22
<212> TYPE: DNA
<213> ORGANISM: ARTIFICIAL
<220> FEATURE:
<223> OTHER INFORMATION: target sequence

<400> SEQUENCE: 116
tggagggctt tgtggtttgt gg                                                   22

<210> SEQ ID NO 117
<211> LENGTH: 22
<212> TYPE: DNA
<213> ORGANISM: ARTIFICIAL
<220> FEATURE:
<223> OTHER INFORMATION: target sequence

<400> SEQUENCE: 117
tgttgaaact ctcttttgt gg                                                    22

<210> SEQ ID NO 118
<211> LENGTH: 22
<212> TYPE: DNA
<213> ORGANISM: ARTIFICIAL
<220> FEATURE:
<223> OTHER INFORMATION: target sequence

<400> SEQUENCE: 118
ttgttgtgga atgtgcaagt gg                                                   22

<210> SEQ ID NO 119
<211> LENGTH: 22
<212> TYPE: DNA
<213> ORGANISM: ARTIFICIAL
<220> FEATURE:
<223> OTHER INFORMATION: target sequence

<400> SEQUENCE: 119
tttccaatca ctctttgtgt gg                                                   22

<210> SEQ ID NO 120
<211> LENGTH: 22
<212> TYPE: DNA
<213> ORGANISM: ARTIFICIAL
<220> FEATURE:
<223> OTHER INFORMATION: target sequence

<400> SEQUENCE: 120
tttctgtggc atctgcaagg gg                                                   22

<210> SEQ ID NO 121
<211> LENGTH: 22
<212> TYPE: DNA
<213> ORGANISM: ARTIFICIAL
<220> FEATURE:
<223> OTHER INFORMATION: target sequence

<400> SEQUENCE: 121
```
tttggaaaca ctcttgttgt gg                                              22

<210> SEQ ID NO 122
<211> LENGTH: 22
<212> TYPE: DNA
<213> ORGANISM: ARTIFICIAL
<220> FEATURE:
<223> OTHER INFORMATION: target sequence

<400> SEQUENCE: 122
tttgtgtaga atctgcaagt gg                                              22

<210> SEQ ID NO 123
<211> LENGTH: 22
<212> TYPE: DNA
<213> ORGANISM: ARTIFICIAL
<220> FEATURE:
<223> OTHER INFORMATION: target sequence

<400> SEQUENCE: 123
tttgtgtgga atctgcaagt gg                                              22

<210> SEQ ID NO 124
<211> LENGTH: 22
<212> TYPE: DNA
<213> ORGANISM: ARTIFICIAL
<220> FEATURE:
<223> OTHER INFORMATION: target sequence

<400> SEQUENCE: 124
ttttcgtagt gtctacaagt gg                                              22

<210> SEQ ID NO 125
<211> LENGTH: 22
<212> TYPE: DNA
<213> ORGANISM: ARTIFICIAL
<220> FEATURE:
<223> OTHER INFORMATION: target sequence

<400> SEQUENCE: 125
ttttgaaact ctctttctgt gg                                              22

<210> SEQ ID NO 126
<211> LENGTH: 22
<212> TYPE: DNA
<213> ORGANISM: ARTIFICIAL
<220> FEATURE:
<223> OTHER INFORMATION: target sequence

<400> SEQUENCE: 126
tttttccaga atctgcaagt gg                                              22

<210> SEQ ID NO 127
<211> LENGTH: 22
<212> TYPE: DNA
<213> ORGANISM: ARTIFICIAL
<220> FEATURE:
<223> OTHER INFORMATION: target sequence

<400> SEQUENCE: 127
tttttctaga atctgcaagt gg                                              22

<210> SEQ ID NO 128
<211> LENGTH: 22
<212> TYPE: DNA

```
<213> ORGANISM: ARTIFICIAL
<220> FEATURE:
<223> OTHER INFORMATION: target sequence

<400> SEQUENCE: 128
tttttgcagg atctacaagt gg                                            22

<210> SEQ ID NO 129
<211> LENGTH: 22
<212> TYPE: DNA
<213> ORGANISM: ARTIFICIAL
<220> FEATURE:
<223> OTHER INFORMATION: target sequence

<400> SEQUENCE: 129
tttttgtaca atctacaagt gg                                            22

<210> SEQ ID NO 130
<211> LENGTH: 22
<212> TYPE: DNA
<213> ORGANISM: ARTIFICIAL
<220> FEATURE:
<223> OTHER INFORMATION: target sequence

<400> SEQUENCE: 130
tttttgtaga aactgcaagg gg                                            22

<210> SEQ ID NO 131
<211> LENGTH: 22
<212> TYPE: DNA
<213> ORGANISM: ARTIFICIAL
<220> FEATURE:
<223> OTHER INFORMATION: target sequence

<400> SEQUENCE: 131
tttttgtaga aactgcaagt gg                                            22

<210> SEQ ID NO 132
<211> LENGTH: 22
<212> TYPE: DNA
<213> ORGANISM: ARTIFICIAL
<220> FEATURE:
<223> OTHER INFORMATION: target sequence

<400> SEQUENCE: 132
tttttgtagg atctgcaagt gg                                            22

<210> SEQ ID NO 133
<211> LENGTH: 22
<212> TYPE: DNA
<213> ORGANISM: ARTIFICIAL
<220> FEATURE:
<223> OTHER INFORMATION: target sequence

<400> SEQUENCE: 133
tttttgtgga atctgcaagt gg                                            22

<210> SEQ ID NO 134
<211> LENGTH: 20
<212> TYPE: DNA
<213> ORGANISM: ARTIFICIAL
<220> FEATURE:
<223> OTHER INFORMATION: guide RNA TARGET SEQUENCE

<400> SEQUENCE: 134
gagggctttg aggcctgtgg                                               20
```

<210> SEQ ID NO 135
<211> LENGTH: 20
<212> TYPE: DNA
<213> ORGANISM: ARTIFICIAL
<220> FEATURE:
<223> OTHER INFORMATION: guide RNA TARGET SEQUENCE

<400> SEQUENCE: 135
gtgttgaaac tctcttttg                                            20

<210> SEQ ID NO 136
<211> LENGTH: 20
<212> TYPE: DNA
<213> ORGANISM: ARTIFICIAL
<220> FEATURE:
<223> OTHER INFORMATION: guide RNA TARGET SEQUENCE

<400> SEQUENCE: 136
gacactgctc tatccatagg                                           20

<210> SEQ ID NO 137
<211> LENGTH: 20
<212> TYPE: DNA
<213> ORGANISM: ARTIFICIAL
<220> FEATURE:
<223> OTHER INFORMATION: guide RNA TARGET SEQUENCE

<400> SEQUENCE: 137
gagggctttg aggcctgtgg                                           20

<210> SEQ ID NO 138
<211> LENGTH: 20
<212> TYPE: DNA
<213> ORGANISM: ARTIFICIAL
<220> FEATURE:
<223> OTHER INFORMATION: guide RNA TARGET SEQUENCE

<400> SEQUENCE: 138
ggaatctgca agtggatatg                                           20

<210> SEQ ID NO 139
<211> LENGTH: 20
<212> TYPE: DNA
<213> ORGANISM: ARTIFICIAL
<220> FEATURE:
<223> OTHER INFORMATION: guide RNA TARGET SEQUENCE

<400> SEQUENCE: 139
ggcatatttg gacctctttg                                           20

<210> SEQ ID NO 140
<211> LENGTH: 20
<212> TYPE: DNA
<213> ORGANISM: ARTIFICIAL
<220> FEATURE:
<223> OTHER INFORMATION: guide RNA TARGET SEQUENCE

<400> SEQUENCE: 140
gtactaccat aggcctaaag                                           20

<210> SEQ ID NO 141
<211> LENGTH: 20
<212> TYPE: DNA
<213> ORGANISM: ARTIFICIAL
<220> FEATURE:

```
<223> OTHER INFORMATION: guide RNA TARGET SEQUENCE

<400> SEQUENCE: 141
gtccaacgaa atcctcagag                                              20

<210> SEQ ID NO 142
<211> LENGTH: 20
<212> TYPE: DNA
<213> ORGANISM: ARTIFICIAL
<220> FEATURE:
<223> OTHER INFORMATION: guide RNA TARGET SEQUENCE

<400> SEQUENCE: 142
gtctgcaagt ggacatttgg                                              20

<210> SEQ ID NO 143
<211> LENGTH: 20
<212> TYPE: DNA
<213> ORGANISM: ARTIFICIAL
<220> FEATURE:
<223> OTHER INFORMATION: guide RNA TARGET SEQUENCE

<400> SEQUENCE: 143
gttgttgtgg aatgtgcaag                                              20

<210> SEQ ID NO 144
<211> LENGTH: 20
<212> TYPE: DNA
<213> ORGANISM: ARTIFICIAL
<220> FEATURE:
<223> OTHER INFORMATION: guide RNA TARGET SEQUENCE

<400> SEQUENCE: 144
gtttgtgtag aatctgcaag                                              20

<210> SEQ ID NO 145
<211> LENGTH: 23
<212> TYPE: DNA
<213> ORGANISM: ARTIFICIAL
<220> FEATURE:
<223> OTHER INFORMATION: guide RNA TARGET

<400> SEQUENCE: 145
tctgacgtcc atcatctctg cgg                                          23

<210> SEQ ID NO 146
<211> LENGTH: 23
<212> TYPE: DNA
<213> ORGANISM: ARTIFICIAL
<220> FEATURE:
<223> OTHER INFORMATION: guide RNA TARGET

<400> SEQUENCE: 146
gccaaccacc gcagagatga tgg                                          23
```